(12) United States Patent
Schulz et al.

(10) Patent No.: US 9,365,830 B2
(45) Date of Patent: Jun. 14, 2016

(54) AGENTS AND METHODS FOR INHIBITING HUMAN PLURIPOTENT STEM CELL GROWTH

(75) Inventors: Thomas Schulz, Athens, GA (US); Allan Robins, Athens, GA (US)

(73) Assignee: VIACYTE, INC., San Diego, CA (US)

( * ) Notice: Subject to any disclaimer, the term of this patent is extended or adjusted under 35 U.S.C. 154(b) by 0 days.

(21) Appl. No.: 13/992,931

(22) PCT Filed: Dec. 8, 2010

(86) PCT No.: PCT/US2010/059586
§ 371 (c)(1),
(2), (4) Date: Jun. 10, 2013

(87) PCT Pub. No.: WO2012/078153
PCT Pub. Date: Jun. 14, 2012

(65) Prior Publication Data
US 2013/0280802 A1    Oct. 24, 2013

(51) Int. Cl.
*C12N 5/071* (2010.01)
*C12N 5/074* (2010.01)
*C12N 5/0735* (2010.01)
*G01N 33/50* (2006.01)

(52) U.S. Cl.
CPC ............ *C12N 5/0696* (2013.01); *C12N 5/0606* (2013.01); *G01N 33/5073* (2013.01); *C12N 2501/999* (2013.01); *C12N 2503/02* (2013.01)

(58) Field of Classification Search
CPC .......................... C12N 5/0606; C12N 5/0609
See application file for complete search history.

(56) References Cited

U.S. PATENT DOCUMENTS

2012/0295346 A1*  11/2012  Levin ........................... 435/366

FOREIGN PATENT DOCUMENTS

WO          0027995          5/2000

OTHER PUBLICATIONS

Miao et al. (J. Biol. Chem. 2001; 276: 32204-32213).*
Santa Cruz Biotechnology, Chelerythrine Chloride (CAS 3895-92-9) (accessed Feb. 4, 2015).*
Caffeic acid (Wikipedia, assessed Feb. 4, 2015).*
Riekstina et al. (Stem Cell Rev and Rep. 2009; 5:378-386).*
Shoreibah, et al., "Anti-human embryonic stem cell monoclonal antibody Hesca-2 binds to a glycan epitope commonly found on carcinomas," Stem Cell Dev 20:515-25(2011).
Tan, et al., "mAb 84, a cytotoxic antibody that kills undifferentiated human embryonic stem cells via oncosi," Stem Cells 27:1792-1801(2009).
Choo, et al., "Selection against undifferentiated human embryonic stem cells by a cytotoxic antibody recognizing podocalyxin-Like protein-1," Stem Cells 26:1454-1463 (2008).
Bieberich, et al., "Selective Apoptosis of Pluripotent Mouse and Human Stem Cells by Novel Ceramide Analogues Prevents Teratoma Formation and Enriches for Neural Precursors in ES Cell—Derived Neural Transplants," Journal Cell Biol 167:723-734(2004).

* cited by examiner

*Primary Examiner* — Scott Long
(74) *Attorney, Agent, or Firm* — The Law Office of Jane K. Babin, Professional Corporation; Jane K. Babin

(57) ABSTRACT

The present invention relates to compositions and methods for inhibiting or suppressing undifferentiated or pluripotent stem cell growth and proliferation in a differentiated or differentiating cell population or culture.

19 Claims, 24 Drawing Sheets

FIG. 6A SOX1
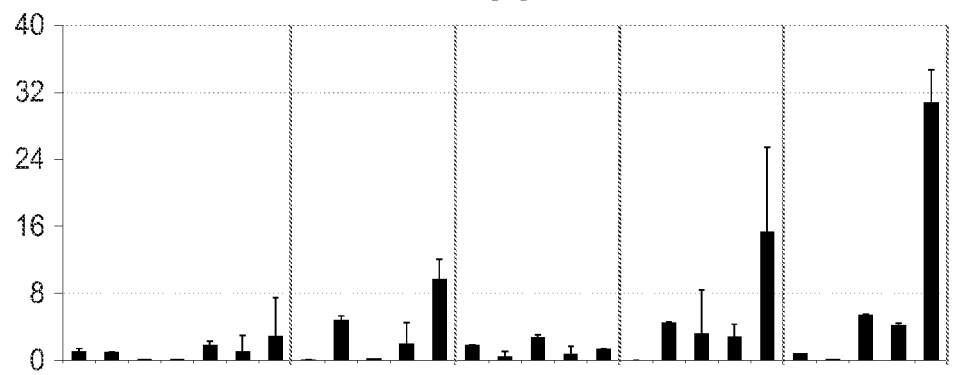
FIG. 6B ZIC1
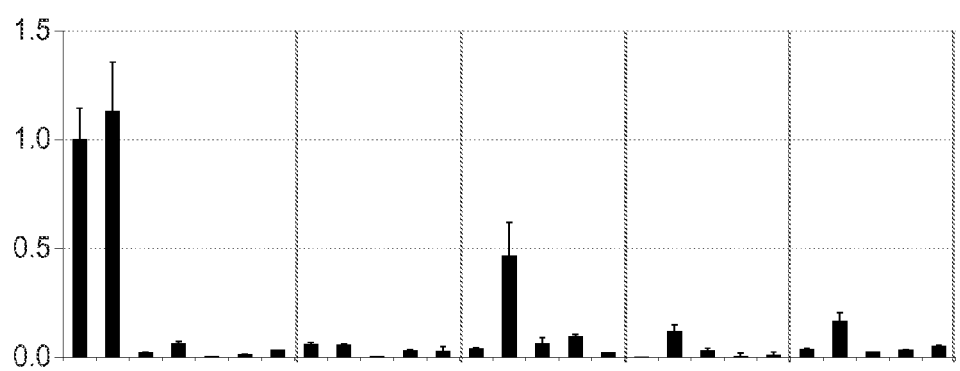
FIG. 6C PAX6
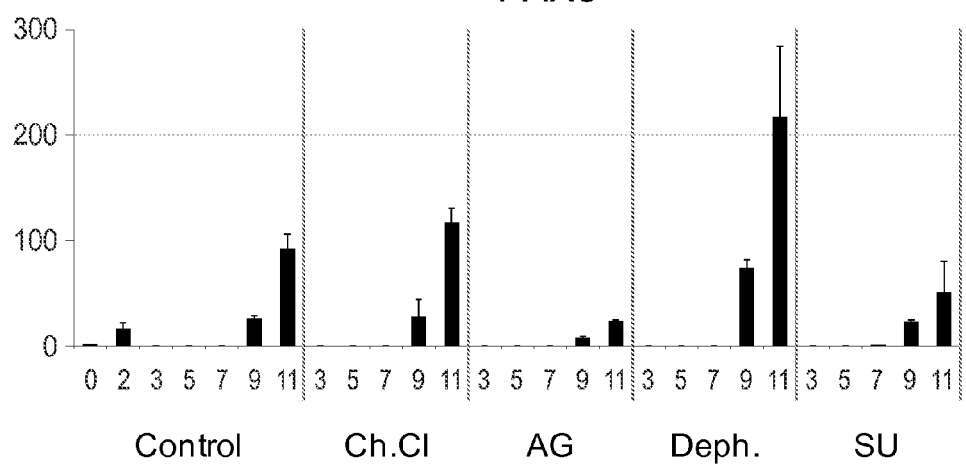

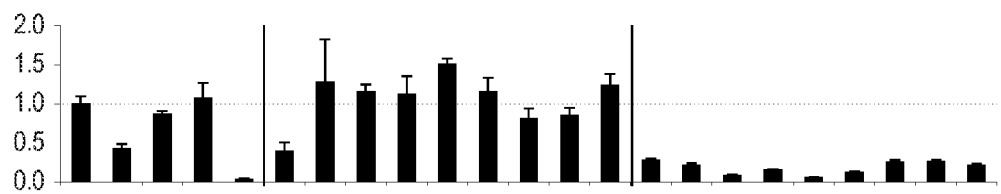
FIG. 9A  OCT4
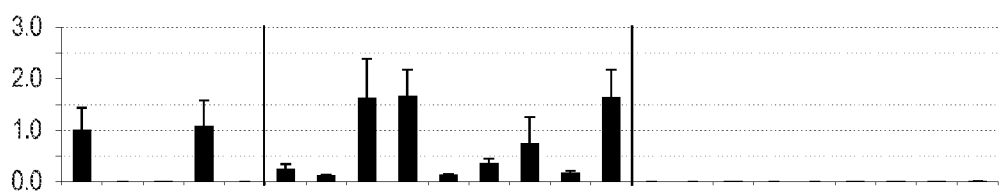
FIG. 9B  SOX17
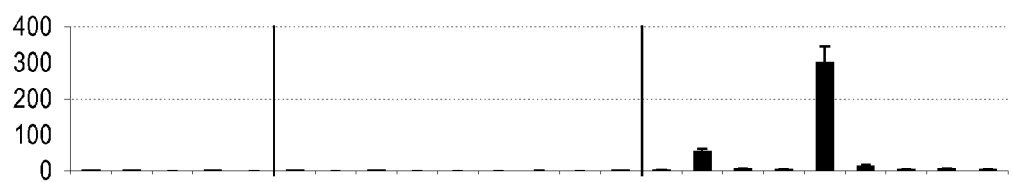
FIG. 9C  PAX6
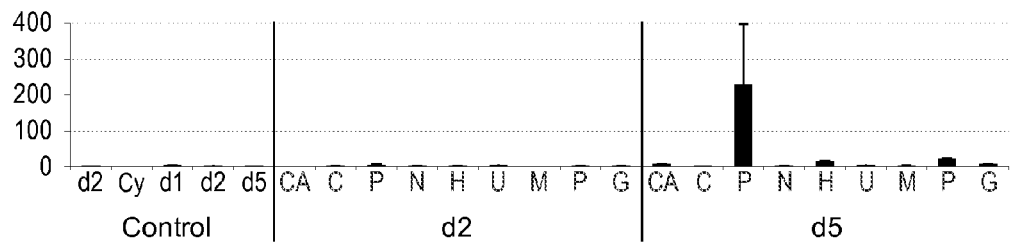
FIG. 9D  CDX2

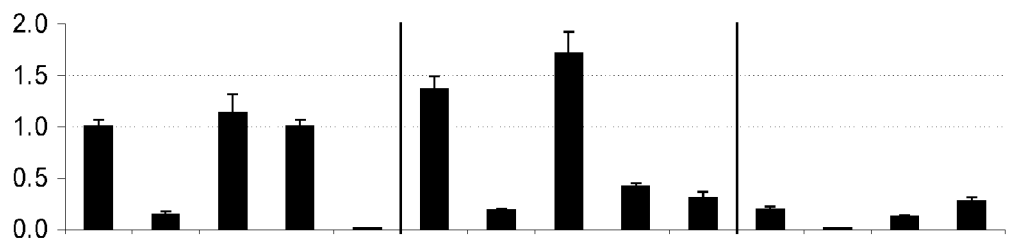
FIG. 9E  OCT4
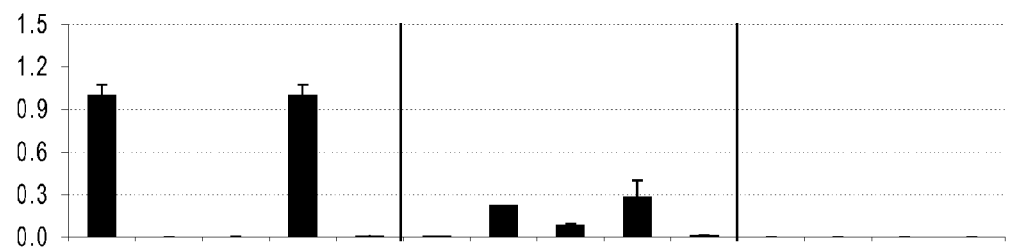
FIG. 9F  SOX17
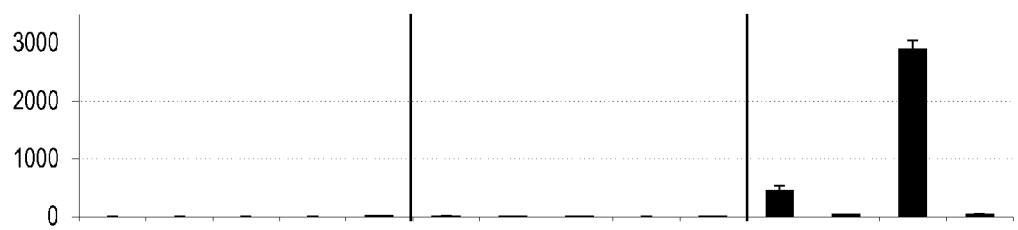
FIG. 9G  PAX6
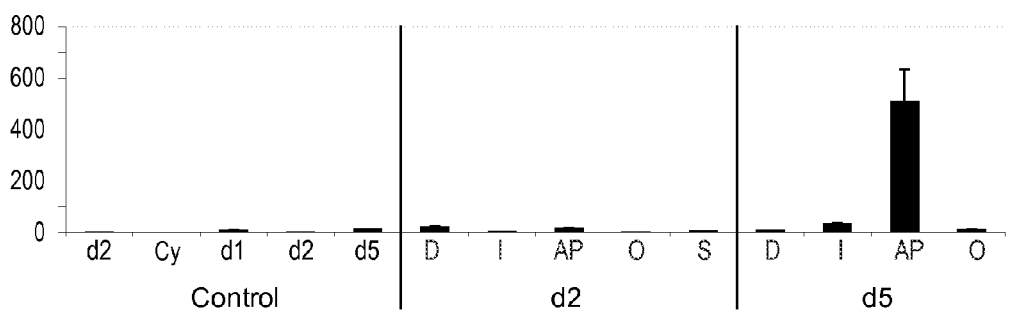
FIG. 9H  CDX2

FIG. 10E PAX4
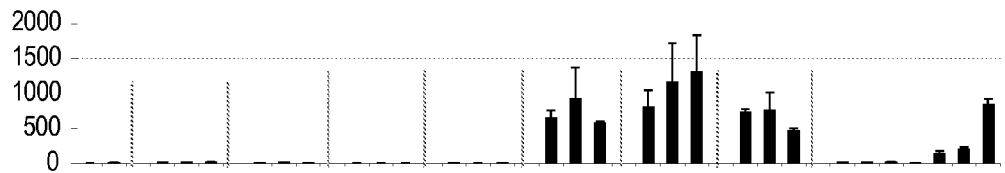
FIG. 10F NGN3
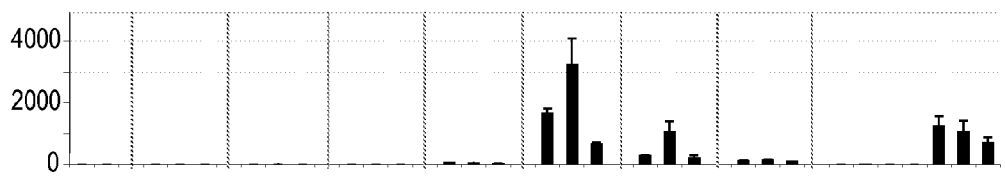
FIG. 10G NKX2.2
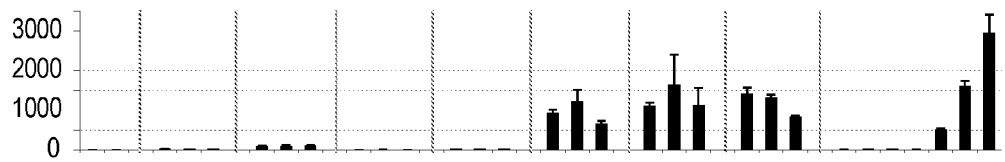
FIG. 10H NKX6.1
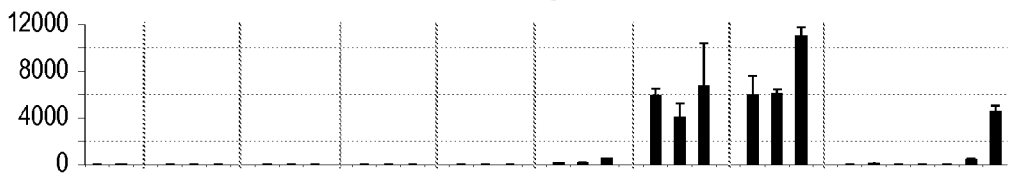
FIG. 10I PTFIA
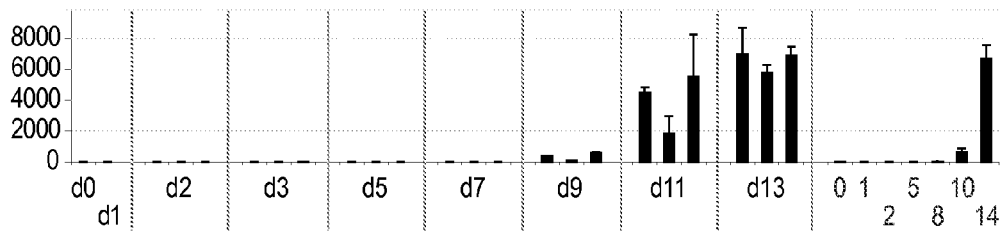

| | Actions | EC50 Matrigel | EC50 SolhSerum | Structure |
|---|---|---|---|---|
| Chelerythrine Chloride | • PKC inhibitor<br>• MAPK activator | 1.2 μM | 1.4 μM | 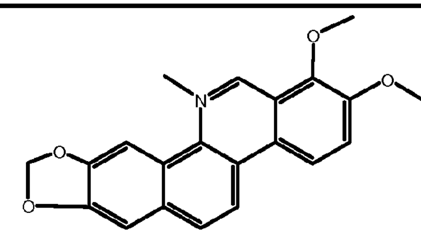 |
| Caffeic Acid | • Antioxidant | 0.17 μM | 0.1 μM | 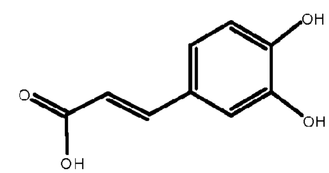 |
| Ivermectin | • Activator of glutamate-gated chloride channels | 0.15 μM | 0.17 μM | 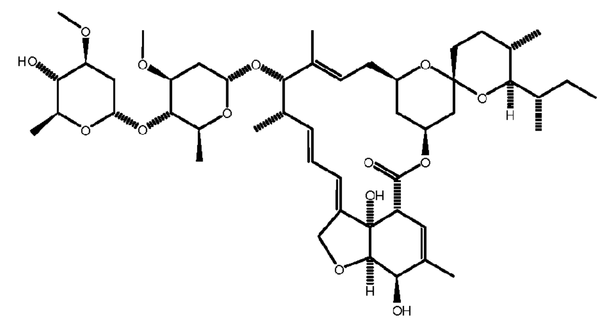 |

FIG. 11

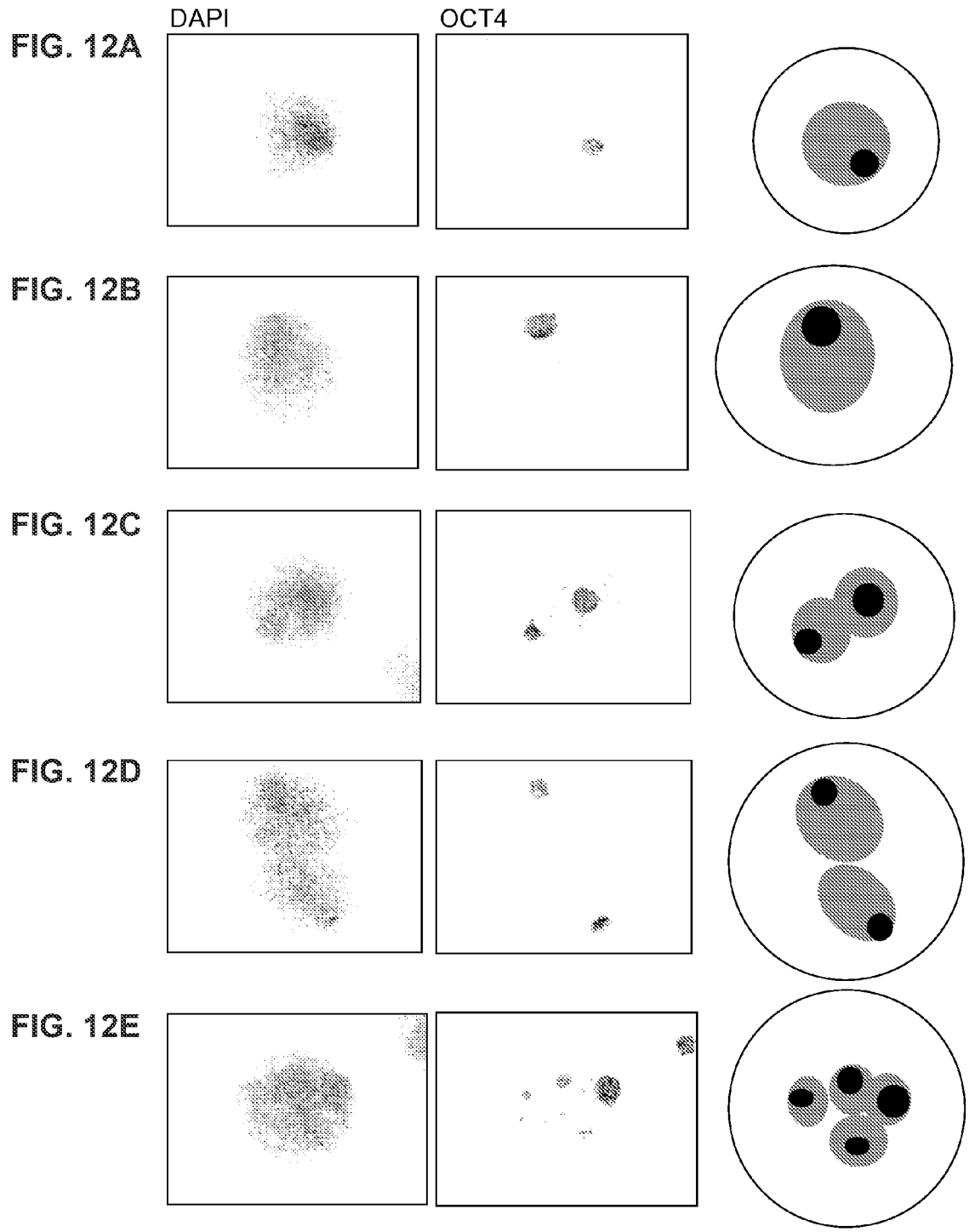

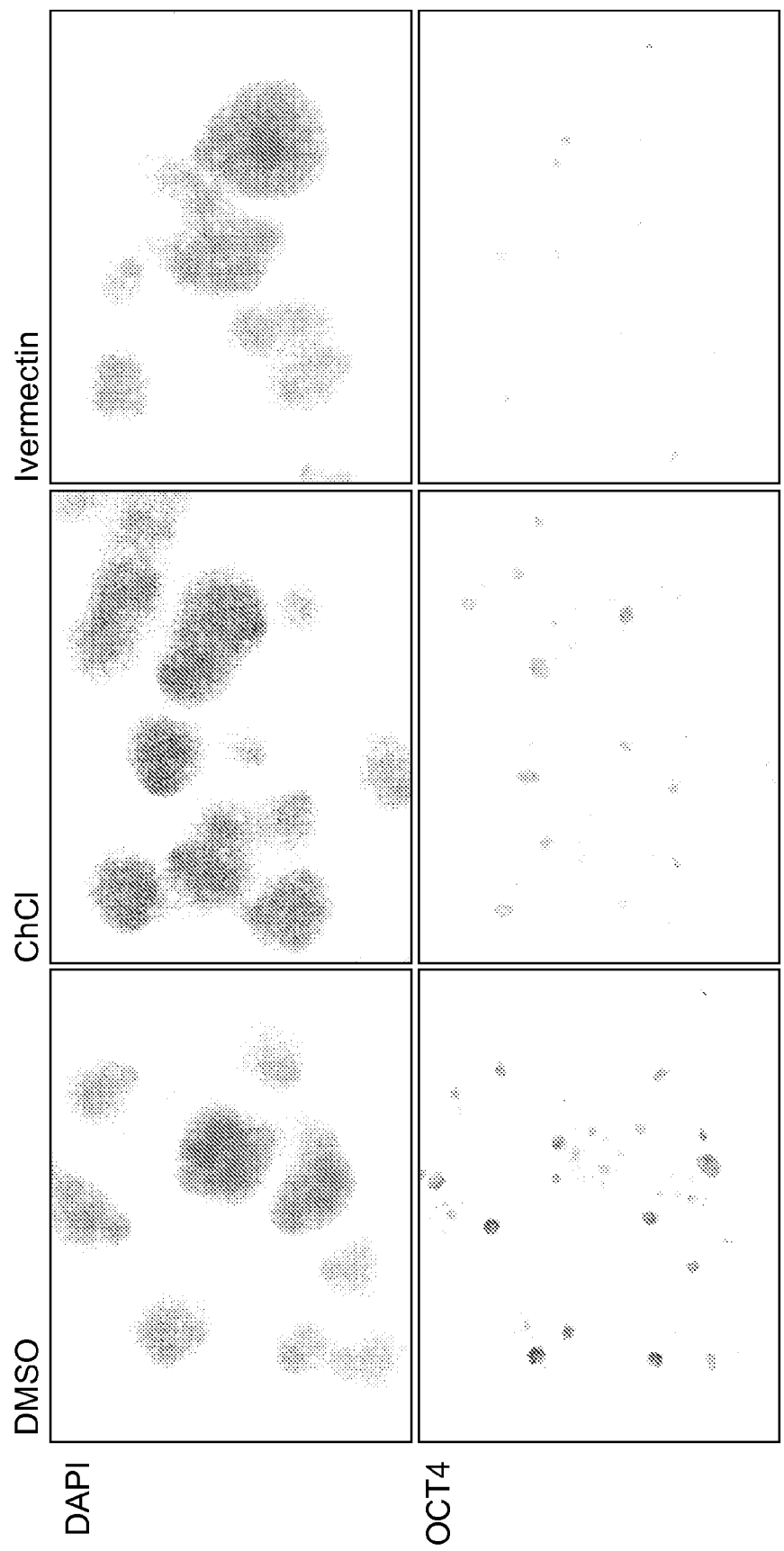

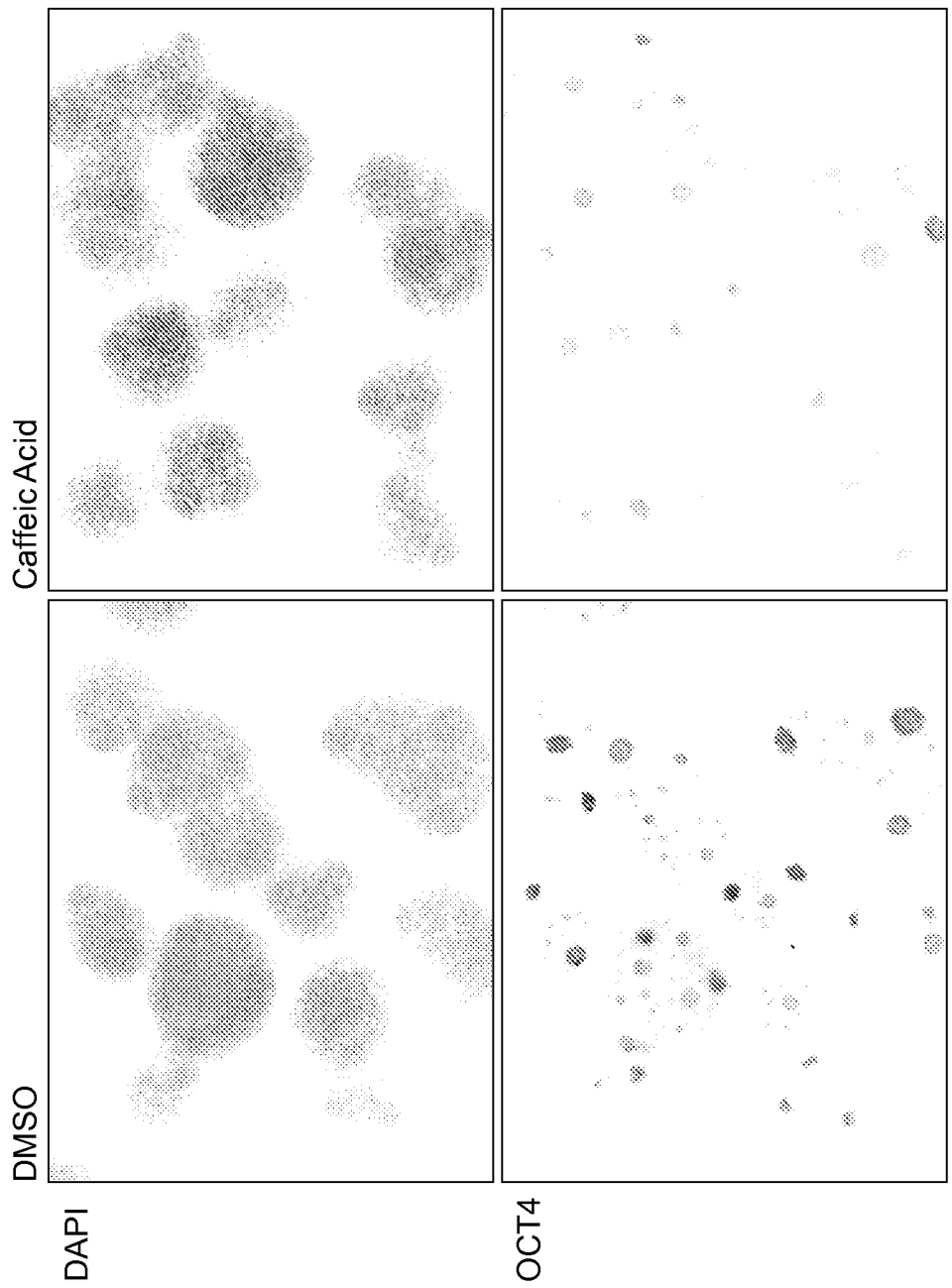

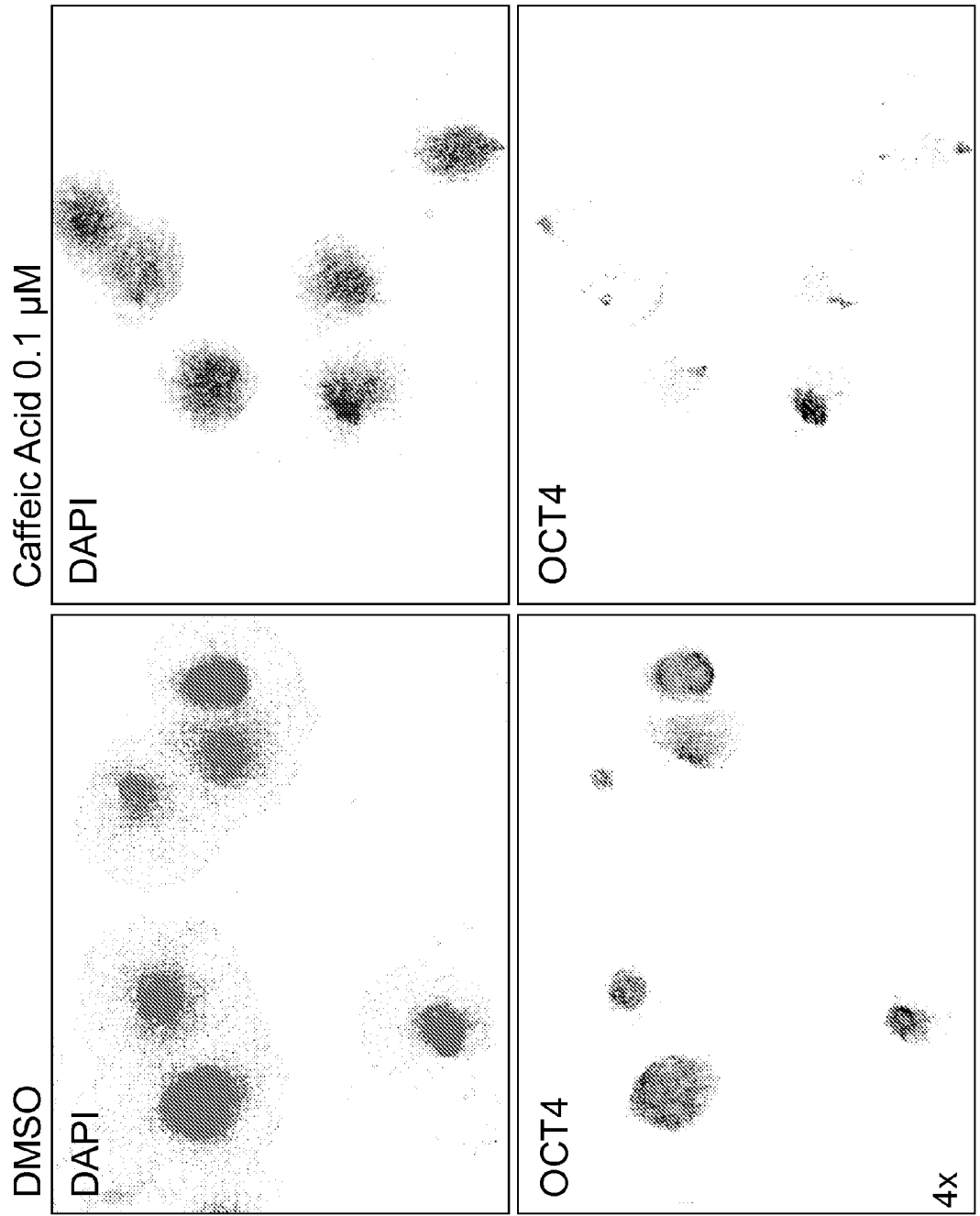

DMSO      Chelerythrine 10 μM
24 hr
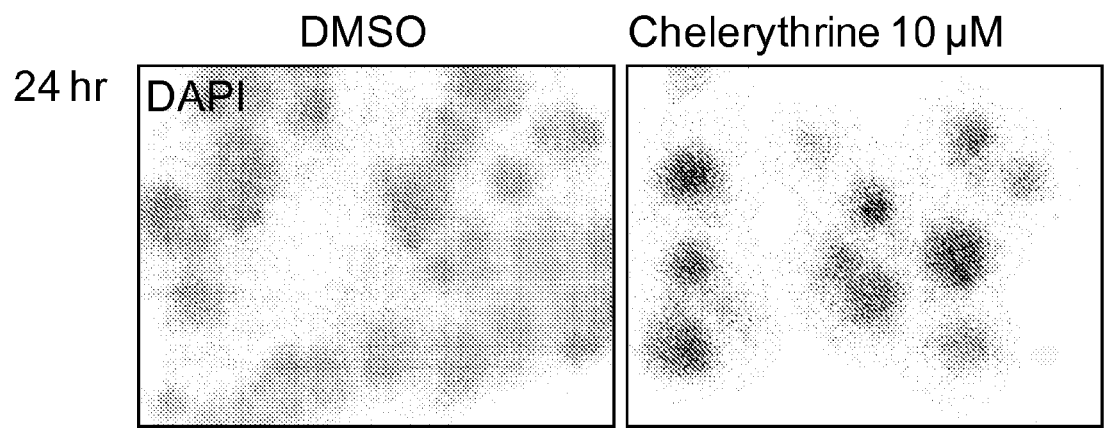
FIG. 15A      FIG. 15B
72 hr
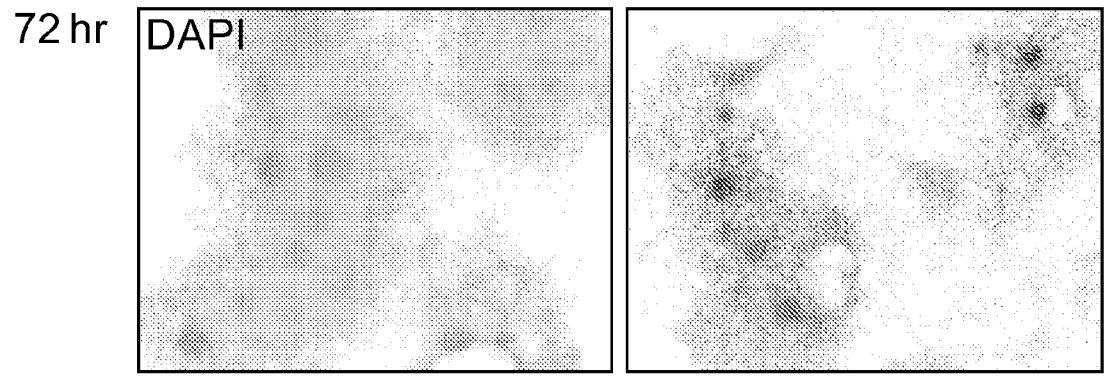
FIG. 15C      FIG. 15D

SEQUENCE LISTING

```
<160> NUMBER OF SEQ ID NOS: 46

<210> SEQ ID NO 1
<211> LENGTH: 21
<212> TYPE: DNA
<213> ORGANISM: Artificial Sequence
<220> FEATURE:
<223> OTHER INFORMATION: Synthetic Primer

<400> SEQUENCE: 1
aagaggccat caagcagatc a                                                 21

<210> SEQ ID NO 2
<211> LENGTH: 17
<212> TYPE: DNA
```

```
<213> ORGANISM: Artificial Sequence
<220> FEATURE:
<223> OTHER INFORMATION: Synthetic Primer

<400> SEQUENCE: 2
caggaggcgc atccaca                                                   17

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
ctggcctgta ccctcatca                                                 20

<210> SEQ ID NO 4
<211> LENGTH: 21
<212> TYPE: DNA
<213> ORGANISM: Artificial Sequence
<220> FEATURE:
<223> OTHER INFORMATION: Synthetic Primer

<400> SEQUENCE: 4
cttcccgtct tgtccaaca a                                               21

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer

<400> SEQUENCE: 5
aagtctacca aagctcacgc g                                              21

<210> SEQ ID NO 6
<211> LENGTH: 15
<212> TYPE: DNA
<213> ORGANISM: Artificial Sequence
<220> FEATURE:
<223> OTHER INFORMATION: Synthetic Primer

<400> SEQUENCE: 6
gtaggcgccg cctgc                                                     15

<210> SEQ ID NO 7
<211> LENGTH: 24
<212> TYPE: DNA
<213> ORGANISM: Artificial Sequence
<220> FEATURE:
<223> OTHER INFORMATION: Synthetic Primer

<400> SEQUENCE: 7
gctcatcgct ctctattctt ttgc                                           24

<210> SEQ ID NO 8
<211> LENGTH: 21
<212> TYPE: DNA
<213> ORGANISM: Artificial Sequence
<220> FEATURE:
<223> OTHER INFORMATION: Synthetic Primer

<400> SEQUENCE: 8
ggttgaggcg tcatcctttc t                                              21
```

<210> SEQ ID NO 9
<211> LENGTH: 18
<212> TYPE: DNA
<213> ORGANISM: Artificial Sequence
<220> FEATURE:
<223> OTHER INFORMATION: Synthetic Primer

<400> SEQUENCE: 9
gggagcggtg aagatgga                                                     18

<210> SEQ ID NO 10
<211> LENGTH: 22
<212> TYPE: DNA
<213> ORGANISM: Artificial Sequence
<220> FEATURE:
<223> OTHER INFORMATION: Synthetic Primer

<400> SEQUENCE: 10
tcatgttgct cacggaggag ta                                                22

<210> SEQ ID NO 11
<211> LENGTH: 24
<212> TYPE: DNA
<213> ORGANISM: Artificial Sequence
<220> FEATURE:
<223> OTHER INFORMATION: Synthetic Primer

<400> SEQUENCE: 11
aagcatttac tttgtggctg gatt                                              24

<210> SEQ ID NO 12
<211> LENGTH: 25
<212> TYPE: DNA
<213> ORGANISM: Artificial Sequence
<220> FEATURE:
<223> OTHER INFORMATION: Synthetic Primer

<400> SEQUENCE: 12
tgatctggat ttctcctctg tgtct                                             25

<210> SEQ ID NO 13
<211> LENGTH: 18
<212> TYPE: DNA
<213> ORGANISM: Artificial Sequence
<220> FEATURE:
<223> OTHER INFORMATION: Synthetic Primer

<400> SEQUENCE: 13
cgctccgctt agcagcat                                                     18

<210> SEQ ID NO 14
<211> LENGTH: 22
<212> TYPE: DNA
<213> ORGANISM: Artificial Sequence
<220> FEATURE:
<223> OTHER INFORMATION: Synthetic Primer

<400> SEQUENCE: 14
gtgttgcctc tatccttccc at                                                22

<210> SEQ ID NO 15
<211> LENGTH: 20
<212> TYPE: DNA
<213> ORGANISM: Artificial Sequence
<220> FEATURE:

<223> OTHER INFORMATION: Synthetic Primer

<400> SEQUENCE: 15
gaagaaggaa gccgtccaga                                                    20

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
gaccttcgag tgctgatccg                                                    20

<210> SEQ ID NO 17
<211> LENGTH: 18
<212> TYPE: DNA
<213> ORGANISM: Artificial Sequence
<220> FEATURE:
<223> OTHER INFORMATION: Synthetic Primer

<400> SEQUENCE: 17
ggcgcagcag aatccaga                                                      18

<210> SEQ ID NO 18
<211> LENGTH: 18
<212> TYPE: DNA
<213> ORGANISM: Artificial Sequence
<220> FEATURE:
<223> OTHER INFORMATION: Synthetic Primer

<400> SEQUENCE: 18
ccacgacttg cccagcat                                                      18

<210> SEQ ID NO 19
<211> LENGTH: 16
<212> TYPE: DNA
<213> ORGANISM: Artificial Sequence
<220> FEATURE:
<223> OTHER INFORMATION: Synthetic Primer

<400> SEQUENCE: 19
caccgcgggc atgatc                                                        16

<210> SEQ ID NO 20
<211> LENGTH: 19
<212> TYPE: DNA
<213> ORGANISM: Artificial Sequence
<220> FEATURE:
<223> OTHER INFORMATION: Synthetic Primer

<400> SEQUENCE: 20
acttccccag gaggttcga                                                     19

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer

<400> SEQUENCE: 21
ggccttcagt actccctgca                                                    20

```
<210> SEQ ID NO 22
<211> LENGTH: 21
<212> TYPE: DNA
<213> ORGANISM: Artificial Sequence
<220> FEATURE:
<223> OTHER INFORMATION: Synthetic Primer

<400> SEQUENCE: 22
gggacttgga gcttgagtcc t                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic Primer

<400> SEQUENCE: 23
gaaggtcatc atctgccatc g                                              21

<210> SEQ ID NO 24
<211> LENGTH: 19
<212> TYPE: DNA
<213> ORGANISM: Artificial Sequence
<220> FEATURE:
<223> OTHER INFORMATION: Synthetic Primer

<400> SEQUENCE: 24
ggccataatc agggtcgct                                                 19

<210> SEQ ID NO 25
<211> LENGTH: 20
<212> TYPE: DNA
<213> ORGANISM: Artificial Sequence
<220> FEATURE:
<223> OTHER INFORMATION: Synthetic Primer

<400> SEQUENCE: 25
ccccagactc cgtcagtttc                                                20

<210> SEQ ID NO 26
<211> LENGTH: 19
<212> TYPE: DNA
<213> ORGANISM: Artificial Sequence
<220> FEATURE:
<223> OTHER INFORMATION: Synthetic Primer

<400> SEQUENCE: 26
tccgtctggt tgggttcag                                                 19

<210> SEQ ID NO 27
<211> LENGTH: 23
<212> TYPE: DNA
<213> ORGANISM: Artificial Sequence
<220> FEATURE:
<223> OTHER INFORMATION: Synthetic Primer

<400> SEQUENCE: 27
ccagaaagga tgcctcataa agg                                            23

<210> SEQ ID NO 28
<211> LENGTH: 18
<212> TYPE: DNA
<213> ORGANISM: Artificial Sequence
<220> FEATURE:
<223> OTHER INFORMATION: Synthetic Primer
```

```
<400> SEQUENCE: 28
tctgcgcgcc cctagtta                                            18

<210> SEQ ID NO 29
<211> LENGTH: 19
<212> TYPE: DNA
<213> ORGANISM: Artificial Sequence
<220> FEATURE:
<223> OTHER INFORMATION: Synthetic Primer

<400> SEQUENCE: 29
tgggctcgag aaggatgtg                                           19

<210> SEQ ID NO 30
<211> LENGTH: 20
<212> TYPE: DNA
<213> ORGANISM: Artificial Sequence
<220> FEATURE:
<223> OTHER INFORMATION: Synthetic Primer

<400> SEQUENCE: 30
gcatagtcgc tgcttgatcg                                          20

<210> SEQ ID NO 31
<211> LENGTH: 20
<212> TYPE: DNA
<213> ORGANISM: Artificial Sequence
<220> FEATURE:
<223> OTHER INFORMATION: Synthetic Primer

<400> SEQUENCE: 31
ccgagtccag gatccaggta                                          20

<210> SEQ ID NO 32
<211> LENGTH: 19
<212> TYPE: DNA
<213> ORGANISM: Artificial Sequence
<220> FEATURE:
<223> OTHER INFORMATION: Synthetic Primer

<400> SEQUENCE: 32
ctctgacgcc gagacttgg                                           19

<210> SEQ ID NO 33
<211> LENGTH: 19
<212> TYPE: DNA
<213> ORGANISM: Artificial Sequence
<220> FEATURE:
<223> OTHER INFORMATION: Synthetic Primer

<400> SEQUENCE: 33
cctcttgcaa tgcggaaag                                           19

<210> SEQ ID NO 34
<211> LENGTH: 19
<212> TYPE: DNA
<213> ORGANISM: Artificial Sequence
<220> FEATURE:
<223> OTHER INFORMATION: Synthetic Primer

<400> SEQUENCE: 34
cgggaggaag gctctcact                                           19

<210> SEQ ID NO 35
<211> LENGTH: 23
```

```
<212> TYPE: DNA
<213> ORGANISM: Artificial Sequence
<220> FEATURE:
<223> OTHER INFORMATION: Synthetic Primer

<400> SEQUENCE: 35
gaggagaaag tggaggtctg gtt                                              23

<210> SEQ ID NO 36
<211> LENGTH: 21
<212> TYPE: DNA
<213> ORGANISM: Artificial Sequence
<220> FEATURE:
<223> OTHER INFORMATION: Synthetic Primer

<400> SEQUENCE: 36
ctctgatgag gaccgcttct g                                                21

<210> SEQ ID NO 37
<211> LENGTH: 21
<212> TYPE: DNA
<213> ORGANISM: Artificial Sequence
<220> FEATURE:
<223> OTHER INFORMATION: Synthetic Primer

<400> SEQUENCE: 37
acagtgccct tcagccagac t                                                21

<210> SEQ ID NO 38
<211> LENGTH: 25
<212> TYPE: DNA
<213> ORGANISM: Artificial Sequence
<220> FEATURE:
<223> OTHER INFORMATION: Synthetic Primer

<400> SEQUENCE: 38
acaactactt tttcacagcc ttcgt                                            25

<210> SEQ ID NO 39
<211> LENGTH: 23
<212> TYPE: DNA
<213> ORGANISM: Artificial Sequence
<220> FEATURE:
<223> OTHER INFORMATION: Synthetic Primer

<400> SEQUENCE: 39
gagaaaccca ctggagatga aca                                              23

<210> SEQ ID NO 40
<211> LENGTH: 23
<212> TYPE: DNA
<213> ORGANISM: Artificial Sequence
<220> FEATURE:
<223> OTHER INFORMATION: Synthetic Primer

<400> SEQUENCE: 40
ctcatggcaa agttcttcca gaa                                              23

<210> SEQ ID NO 41
<211> LENGTH: 19
<212> TYPE: DNA
<213> ORGANISM: Artificial Sequence
<220> FEATURE:
<223> OTHER INFORMATION: Synthetic Primer

<400> SEQUENCE: 41
```

-continued

```
atgcaccgct acgacatgg                                                19

<210> SEQ ID NO 42
<211> LENGTH: 21
<212> TYPE: DNA
<213> ORGANISM: Artificial Sequence
<220> FEATURE:
<223> OTHER INFORMATION: Synthetic Primer

<400> SEQUENCE: 42
ctcatgtagc cctgcgagtt g                                             21

<210> SEQ ID NO 43
<211> LENGTH: 20
<212> TYPE: DNA
<213> ORGANISM: Artificial Sequence
<220> FEATURE:
<223> OTHER INFORMATION: Synthetic Primer

<400> SEQUENCE: 43
ctggctgtgg caaggtcttc                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic Primer

<400> SEQUENCE: 44
cagccctcaa actcgcactt                                               20

<210> SEQ ID NO 45
<211> LENGTH: 18
<212> TYPE: DNA
<213> ORGANISM: Artificial Sequence
<220> FEATURE:
<223> OTHER INFORMATION: Synthetic Primer

<400> SEQUENCE: 45
atcgaggagc gccacaac                                                 18

<210> SEQ ID NO 46
<211> LENGTH: 19
<212> TYPE: DNA
<213> ORGANISM: Artificial Sequence
<220> FEATURE:
<223> OTHER INFORMATION: Synthetic Primer

<400> SEQUENCE: 46
tgctggatgg tgtcctggt                                                19
```

AGENTS AND METHODS FOR INHIBITING HUMAN PLURIPOTENT STEM CELL GROWTH

STATEMENT REGARDING FEDERALLY SPONSORED RESEARCH OR DEVELOPMENT

Part of the work performed during development of this invention utilized U.S. Government funds from National Institutes of Health Grant No. 1P01GM085354-01. The U.S. Government has certain rights in this invention.

RELATED APPLICATIONS

This application is a U.S. National Phase under 35 U.S.C. 371 and claims the benefit of priority of PCT/US10/59586, filed Dec. 8,2010, the entire disclosure of which is incorporated herein by reference.

FIELD OF THE INVENTION

The present invention relates to screening and identification of cytotoxic or inhibitory agents of pluripotent stem cells in vitro.

BACKGROUND OF THE INVENTION

A potential hurdle in developing cell replacement therapies using human embryonic stem cells (hESCs or hES cells) is that differentiation methods may not specify all hESCs homogeneously. Undifferentiated hESCs, partially differentiated or progenitor cells, or incorrectly specified cells may persist within differentiated cell populations. The presence of such cells may contribute to "off-target" biological effects upon implantation, the largest perceived issue being implant overgrowth or generation of teratomas. It is not clear if teratomas are caused solely by persistent hESCs, or if partially differentiated or progenitor cells also contribute to teratoma formation. Regardless, it will be important to demonstrate that transplantable cell populations are safe and do not contain teratoma-causing subpopulations.

It is possible to minimize unwanted subpopulations of cells, or purify desirable populations prior to transplantation or delivery, by depleting, isolating, killing or inhibiting undifferentiated cells using a variety of approaches that involve targeted agents such as small molecule organic compounds, cell surface markers or antibodies (Choo et al. Stem Cells 2008 2:1454-63). There is thus a need to identify agents and methods that can be used to eliminate potentially unsafe populations of otherwise transplantable cells.

SUMMARY OF THE INVENTION

The present invention provides methods for identifying inhibitors and cyotoxic agents by contacting a pluripotent stem cell (such as an ES cell or an iPS cell) with a candidate inhibitor or cyotoxic agent and observing that proliferation or viability of the pluripotent stem cell is inhibited. The selectivity of the inhibitor or cyotoxic agent can be determined by contacting a differentiated or differentiating cell with the candidate inhibitor or cyotoxic agent and observing that proliferation and viability of the differentiated or differentiating cell is not affected by the candidate inhibitor or cyotoxic agent. For example, the present invention describes various small molecule compounds capable of ablating uncommitted hESCs within differentiating populations. The compounds identified are candidates to include in the manufacturing and scale-up production of a cell therapy product, potentially eliminating undifferentiated cells, for example, pluripotent stem cells, thereby providing an improved measure of safety against teratoma formation.

The cells of the present invention can be any species, but in certain embodiments are primate cells, such as human cells.

Proliferation and viability can be determined by any method known in the art, but conveniently can be determined using an impedance assay. Alternatively, proliferation and viability of cells according to the present invention can be determined by alkaline phosphatase staining or by analyzing the cells for the presence of a marker.

Differentiating or differentiated cells of the invention are typically derived from pluripotent stem cells, and may include such cells as definitive endoderm cells, PDX1-negative foregut endoderm cells, PDX1-positive foregut endoderm cells, PDX1-positive pancreatic endoderm cells, endocrine progenitor cells and endocrine precursor cells.

Differentiating or differentiated cells can be analyzed in parallel, or can be present together with pluripotent stem cells, such as in a culture of cells, which can be a population of cells undergoing differentiation from pluripotent stem cells to more differentiated derivatives of the pluripotent stem cells. For example, the population of cells can include cells from a Stage 1, a Stage 2, a Stage 3, a Stage 4 and a Stage 5 differentiation of pluripotent stem cells to pancreatic endoderm-lineage cells.

In certain embodiments of the invention, the culture of cells is an adherent culture. In other embodiments, the culture of cells is a suspension culture, which can be a suspension of cell aggregates.

In one aspect, a stem cell-selective inhibitor or cyotoxic agent of the invention will have no effect on differentiation or differentiation potential of cells, and particularly on pluripotent stem cell and differentiating and differentiated derivatives thereof. The differentiation and differentiation potential can be determined by analyzing the cells for the presence of markers. Such markers can include those that identify pluripotent stem cells, such as OCT4, SSEA-1, SSEA-3, SSEA-4, TRA-1-60, TRA-1-81, Alkaline Phosphatase, NANOG and SOX2. Markers useful in the invention can also identify differentiating or differentiated cells, such as those that identify Stage 1 differentiations and definitive endoderm cells including SOX17, FOXA2/HNF3β, CER, MIXL1, EOMES, GSC and CXCR4; markers that identify Stage 2 differentiations and PDX1-negative foregut endoderm cells, such as SOX17, HNF1β, HNF1α, HNF4α and FOXA1; markers that identify Stage 3 differentiations or a PDX1-positive foregut endoderm cells, such as PDX1, HNF6, SOX9 and PROX1; markers that identify Stage 4 differentiations or PDX1-positive pancreatic endoderm progenitor cells, such as PDX1, NKX6.1, PTF1A, CPA and cMYC; and markers that identify Stage 5 differentiations, endocrine precursor cells and/or endocrine progenitor cells, such NGN3, PAX4, ARX and NKX2.2

In some aspects, cells may be monitored for undesirable differentiation (e.g., cells which are not derived from definitive endoderm cells or non-pancreatic type cells), for which the following markers and others known in the art may be used: AFP, CALCR, CMKOR1, CRIP1, FOXQ1, GATA4, GCG, CHGA, CPA, FGF17, GHRL, INS, MAFA, NFM, PAX3, PAX6, PP, PROX1, SOX1, SOX6, SOX7, SST, SYP, VWF and ZIC1.

These and other markers can be detected by any method known in the art, including, but not limited to Q-PCR, immunofluorescence, immunohistocheistry, cell sorting, ELISA, Northern blotting and Western blotting, multi-plex digital gene expression technology that relies on hybridization based capture and detection technologies.

In some embodiments, it may be advantageous to culture samples of cells treated with a candidate inhibitor or cytotoxic agent under conditions that support pluripotent stem cell expansion, prior to analyzing for the presence of a marker. In this way, the detection of pluripotent stem cells can be enhanced or amplified.

It is also contemplated that screening methods of the invention can include analysis of the effects of candidate inhibitor or cyotoxic agents at various time points. For example, a cell or cell culture can be contacted with a candidate inhibitor or cytotoxic agent at a first time point and an effect of the inhibitor or cytotoxic agent detected at a subsequent second time point. Where the cell or cell culture is a population of cells undergoing differentiation, the first time point can be, for example, Stage 1 differentiation and the second time point can be during Stage 2, Stage 3, Stage 4 or Stage 5 differentiation.

The present invention also provides methods for reducing the number or percentage of pluripotent stem cells in a population of cells by contacting the pluripotent stem cell population with a pluripotent stem cell-selective inhibitor or cytoxic agent. In certain embodiments, the pluripotent stem cell-selective inhibitor or cytoxic agent is selected from caffeic acid, Ivermectin, chelerythrine chloride and combinations thereof. Typically, the cells will be contacted in a cell culture medium containing an effective amount of the stem cell-selective inhibitor or cytoxic agent, such as at least about 1 μM caffeic acid, at least about 1 μM Ivermectin, or at least 5 μM chelerythrine chloride.

The invention contemplates that such methods will be particularly useful for reducing the number or percentage of pluripotent stem cells in populations of differentiating or differentiated cells, such as those populations derived from pluripotent stem cells.

In certain embodiments, the pluripotent stem cells are differentiated to endoderm lineage cells, such as pancreatic lineage cells, and then treated with a pluripotent stem cell-selective inhibitor or cytoxic agent of the invention to reduce undifferentiated pluripotent stem cells in the final differentiation, or during the differentiation process. Such differentiating and differentiated cells include definitive endoderm cells, PDX1-negative foregut endoderm cells, PDX1-positive foregut endoderm cells, PDX1-positive pancreatic endoderm progenitor cells, endocrine progenitor cells and endocrine precursor cells.

Advantageously, the methods of the invention are equally applicable to both small-scale culture (e.g. up to about $10^5$ cells), such as in 96-well and 6-well plates, and larger plates or flasks, such as 60 mm$^2$, 100 mm$^2$, 150 mm$^2$ culture vessels, T25 flasks, T75 flasks, T175 flasks, Triple flasks, and smaller cell factories such as 2, 5 or 10 stack cell factories as well as large-scale culture of at least about $1 \times 10^9$ cells, such as in spinner flasks, bioreactor vessels and other vessels such as 40 stack cell factories that will be well known to the skilled artisan. One skilled in the art will appreciate that the terms "small-scale" and "large-scale" are not limiting and that for any study, the number of cells and therefore the volume capacity of the culture vessel will depend on the nature of the studies.

Thus, the present invention also provides methods for differentiating a population of pluripotent stem cells by contacting the population of pluripotent stem cells with at least one differentiating condition, to produce a differentiated population of cells, where at least some of the cells are differentiating and at least some of the cells are not differentiating (e.g. remain pluripotent); and then treating the differentiated population of cells with a pluripotent stem cell-specific inhibitor or cytoxic agent. According to such methods, the pluripotent stem cell-selective inhibitor or cytoxic agent is one that, at a pluripotent stem cell inhibitory or cytoxic effective dose, has no effect on the differentiation or differentiation potential of the of pluripotent stem cells or differentiated derivatives thereof and at the same time has no effect on the viability or proliferation of the differentiating or differentiated derivates.

Moreover, the methods of the invention can be used with differentiation protocols that involve sequentially contacting pluripotent stem cells with two or more differentiating conditions, such as the sequential differentiation of pluripotent stem cells to pancreatic endocrine cells through Stage 1 (definitive endoderm), Stage 2 (PDX1-negative foregut endoderm), Stage 3 (PDX1-positive foregut endoderm), Stage 4 (PDX1-positive pancreatic endoderm progenitor), or Stage 5 (endocrine progenitors and endocrine precursors). Differentiating conditions useful for this type of diffenation series include culture medium, compounds, and growth factors, such as differentiating cell culture media containing, aTGFβ superfamily member; a Wnt family member; a Wnt pathway activator; a ROCK inhibitor; an FGF family member; a hedgehog pathway inhibitor; a TGFβ superfamily inhibitor; a retinoid; a retinoic acid analog; an EGF family member; and/or a gamma secretase inhibitor. Also included are conditions such as reducing or eliminating serum; reducing or eliminating insulin and insulin-like growth factors; reducing or eliminating TGFβ superfamily growth factor signaling; reducing or eliminating gamma secretase activity; reducing or eliminating hedgehog pathway signalling; activating TGFβ superfamily growth factor signaling; activating FGF family growth factor signalling; activating EGF family growth factor signalling; activating a Wnt pathway; and activating a retinoic acid receptor family member. These conditions can be readily accomplished with the methods of the present invention.

Also provided by the present invention are compositions that include pluripotent stem cells and differentiating derivative and/or differentiated derivatives and one or more pluripotent stem cell-selective inhibitor or cytoxic agent described herein. Typically, the compositions will be differentiations in which the inhibition or removal of pluripotent stem cells is required, such as where the cells will be used for implantation into a subject.

BRIEF DESCRIPTION OF THE DRAWINGS

FIG. 1 is a collection of graphs showing Q-PCR gene expression data obtained for various markers, which demonstrate that Q-PCR can be used as a measure of the relative abundance of cell types in mixed cell populations.

FIGS. 3A and 3B) or definitive endoderm cells (DE; FIGS. 3C and 3D) in the presences of seven LOPAC1280™ compounds that caused a reduction or drop in cellular impedance, indicating cytotoxicity in hESC cultures but not differentiating definitive endoderm.

(FIG. 5J), NGN3 (FIG. 5K), NKX6.1 (FIG. 5L) and PAX4 (FIG. 5M) with treatment of candidate selective cytotoxic agents from the LOPAC1280™ sublibrary (Table 4) to suspension aggregate cell cultures at Stages 1-4. Expression levels are normalized to the average expression levels of housekeeping genes. The graphs depict fold regulation compared to hESC sample. Ch.Cl=chelerythrine chloride; Deph.=dephostatin; AG=AG 490; SU=SU6656.

FIGS. 6A-6F are bar graphs showing the relative gene expression levels of markers of non-pancreatic lineage cells: SOX1 (FIG. 6A; e.g., at least observed in extraembryonic and neural cellss), ZIC1 (FIG. 6B; e.g., at least observed in early neural cells), PAX6 (FIG. 6C; e.g., at least observed in neural ectoderm cells), SOX7 (FIG. 6D; e.g., at least observed in extraembryonic cells), AFP (FIG. 6E; e.g., at least observed in liver cell and extraembryonic cells) and CDX2 (FIG. 6F; e.g., at least observed in extraembryonic cells) in compound-treated differentiations. Chelerythrine chloride (Ch. Cl) and dephostatin (Deph.) do not promote differentiation of non-pancreatic lineage cells, or "off-target" cells, whereas tyrphostin AG 490 (AG) and SU6656 (SU) appeared to produce elevated expression of AFP and CDX2, respectively, which are markers uncharacteristic of pancreatic cells and are not typically expressed in pancreatic lineages.

FIGS. 9A-9H are bar graphs showing the relative gene expression levels of OCT4 (FIGS. 9A and 9E), SOX17 (FIGS. 9B and 9F), PAX6 (FIGS. 9C and 9G) and CDX2 (FIGS. 9D and 9H) with treatment of candidate selective cytotoxic agents from the LOPAC1280™ sublibrary (Table 4) to suspension aggregate cell cultures at Stage 1. The cultures were differentiated to the end of Stage 2. The expression levels are normalized to the average expression levels of a day 2 sample from a previously qualified Stage 1 differentiation (left panels). The graphs depict fold regulation compared to the day 2 sample. Cy=CyT49 hESC line; CA=Caffeic Acid; C=Calmidazolium; P=Pyrocatechol; N=Napthycidine; H=Hydroxyanilide; U=U-73343; M=MG624; P=Pentamidine; G=Guinacrine; D=Dopieridone; I=Ivermectin; AP=Amm. Pyrrolidinine; O=Oleoyldopamine; S=SKF96365.

FIGS. 10A-10I are bar graphs showing the relative gene expression levels of OCT4 (FIG. 10A), MIXL (FIG. 10B), HNF1B (FIG. 10C), HNF4A (FIG. 10D), PAX4 (FIG. 10E), NGN3 (FIG. 10F), NKX2.2 (FIG. 10G), NKX6.1 (FIG. 10H), and PTF1A (FIG. 10I) after treatment of suspension aggregate cell cultures at Stages 1 with DMSO (Control), 0.1 μM Caffeic acid or 0.17 μM Ivermectin agents. Untreated control samples were collected at d0 and d1 (left panel). Treated samples were collected at d2, d3, d5, d7, d9, d11, and d13. The columns for each day of the treated samples are (from left to right): DMSO, Caffeic acid, and Ivermectin. The cultures were differentiated to the end of Stage 4. The results from an untreated, pancreatic endoderm differentiation are shown on the right, with samples collected on days 0, 1, 2, 5, 8, 10 and 14.

FIG. 11 is a table showing the names, actions and structures of the three compounds from LOPAC1280™ library that were cytotoxic to hESCs but did not affect cell viability of differentiated cells.

FIGS. 12A-12E are images of post-Stage 1 suspension aggregates plated in adherent culture in hESC medium and stained with nuclear stain DAPI (left panels) and OCT4 (middle panels). The OCT4-positive clusters are shown in the right panels as filled-in dark clusters either in smaller primary or larger secondary clusters.

FIGS. 13A-13E. are images showing the depletion of OCT4-positive cells in Stage1 suspension aggregate cultures treated with chelerythrine chloride (ChCl; FIG. 13B), Ivermectin (FIG. 13C), and Caffeic Acid (FIG. 13E) as compared to control cells treated with DMSO (FIGS. 13A and 13D) from Stage 1.

FIGS. 14A-14B are images showing the depletion of OCT4-positive cells in Stage1 suspension aggregate cultures of BG02 hES cell line treated with Caffeic Acid (FIG. 14B) as compared to control, DMSO treated cultures (FIG. A).

FIGS. 15A-15D are images showing the depletion of OCT4-positive cells in Stage1 suspension aggregate cultures using chelerythrine chloride from day 1 to 2 of Stage 1. Aggregates were plated in adherent culture in hESC medium for either 24 (top) or 72 hours (bottom) before staining.

DETAILED DESCRIPTION

Figure 1A:
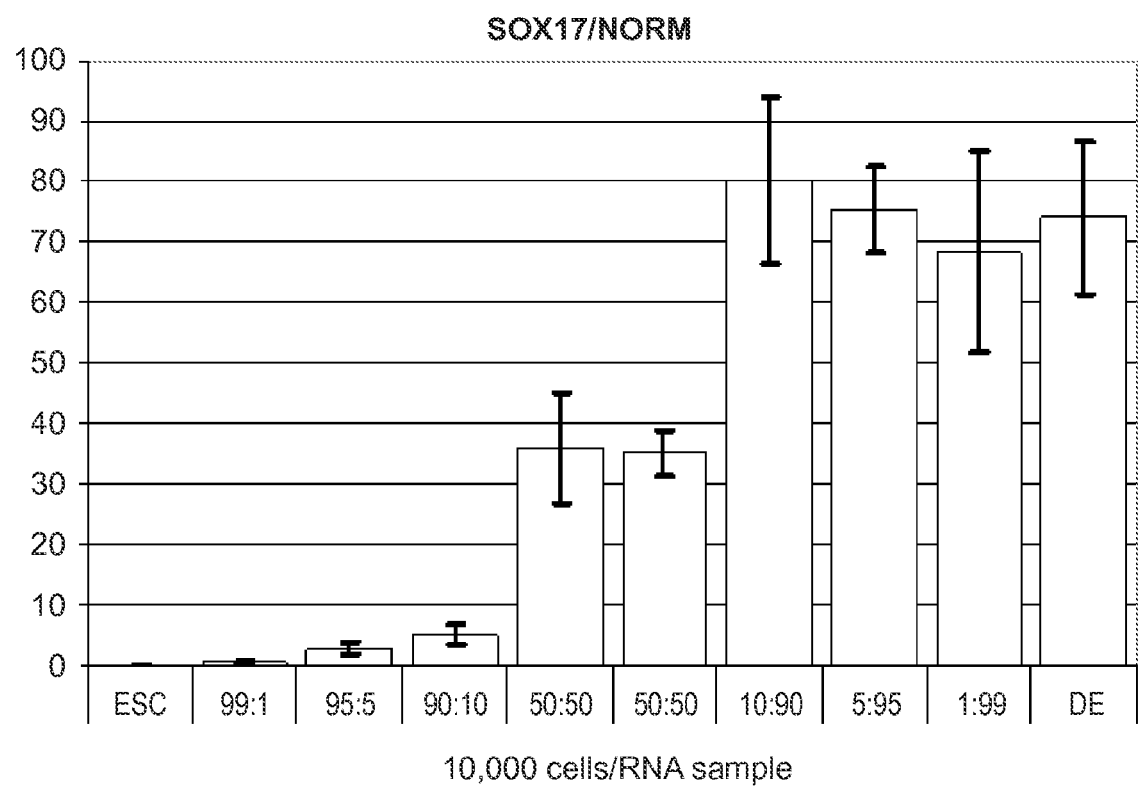
FIG. 1A shows SOX17 gene expression in 100% hESCs (far left column) and from 100% definitive cells (DE; far right column) The columns in between the 100% hESCs and the 100% DE show SOX17 gene expression from known dilution mixtures (or ratios) of hESCs:DE cells, 99:1 hESCs:DE cells ($2^{nd}$ column from the left), 95:5 hESCs:DE cells ($3^{rd}$ column from the left) and 90:10 hESCs:DE cells ($4^{th}$ column from the left).

The present invention may be understood more readily by reference to the following detailed description of the invention and the Examples included herein. However, before the present compositions and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. See Sambrook et al. (1989) Molecular Cloning, 2nd Ed, Cold Spring Harbor Laboratory, Plainview, N.Y.; Maniatis et al., (1982) Molecular Cloning, Cold Spring Harbor Laboratory, Plainview, N.Y.; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif & Wensink, 1982 Practical Methods in Molecular Biology; Glover (Ed.) 1985 DNA Cloning Vol. I and II, IRL Press, Oxford, UK; Hames & Higgins (Eds.) 1985 Nucleic Acid Hybridization, IRL Press, Oxford, UK; and Setlow & Hollaender 1979 Genetic Engineering: Principles and Methods, Vols. 1-4, Plenum Press, NY. Lastly, abbreviations and nomenclature, where employed, are deemed standard in the field and commonly used in professional journals such as those cited herein.

Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th Ed., Berlin: Springer-Verlag; and in Current Protocols in Molecular Biology, Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell, two cells, or a plurality of cells.

Also, for the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

"About" or "approximately" as used herein means that a number referred to as "about" or "approximately" comprises the recited number plus or minus 1-10% of that recited number. For example, about 50 nucleotides can mean 45-55 nucleotides or as few as 49-51 nucleotides depending on the situation. Whenever it appears herein, a numerical range, such as "45-55", refers to each integer in the given range; e.g., "45-55%" means that the percentage can be 45%, 46%, etc., up to and including 55%. Where a range described herein includes decimal values, such as "1.2% to 10.5%", the range refers to each decimal value of the smallest increment indicated in the given range; e.g. "1.2% to 10.5%" means that the percentage can be 1.2%, 1.3%, 1.4%, 1.5%, etc. up to and including 10.5%; while "1.20% to 10.50%" means that the percentage can be 1.20%, 1.21%, 1.22%, 1.23%, etc. up to and including 10.50%.

As used herein, "single cell suspension" or equivalents expressions, refers to a mixture of a fluid and a cell, or more typically a plurality of cells, that are separated from each other (i.e. not aggregated), which can be prepared by any available mechanical, biological or chemical means. Single cell suspensions described herein are typically preparations of viable hES cells or hES-derived cells suspended in a physiological solution, such as a basal salt solution, saline, cell culture media, or the like. Several methods exist for dissociating cell clusters to form single cell suspensions from primary tissues, adherent cells in culture, and cell aggregates, including but not limited to, methods that dissociate cells by physical force (mechanical dissociation such as cell scraping, trituration through a narrow bore pipette, fine needle aspiration, vortex disaggregation and forced filtration through a fine nylon or stainless steel mesh), with enzymes (i.e. enzymatic dissociation using trypsin, collagenase, Accutase™ and the like), or combinations thereof. Further, methods and culture media conditions capable of supporting growth and viability of single-cell suspensions of hES cells are useful for expansion, cell sorting, and defined seeding for multi-well plate assays and enable automatization of culture procedures and clonal expansion. Thus, one embodiment of the invention provides methods for generating a stable single-cell enzymatic dissociation hES cells or hES-derived cell culture system capable of supporting long-term maintenance and efficient expansion of undifferentiated, pluripotent hES cell or differentiated hES cells.

As used herein, the term "contacting" (i.e., contacting a cell e.g., a differentiable cell, with a compound) is intended to include incubating the compound and the cell together in vitro (e.g., adding the compound to cells in culture). The term "contacting" is not intended to include the in vivo exposure of cells to a defined cell culture medium comprising components, compounds, growth factors and the like (e.g. a neurotransmitter, an ErbB3 ligand, a member of the TGF-β family, etc.), or such components compounds, growth factors and the like as they occur naturally in a subject (i.e., exposure that may occur as a result of a natural physiological process). For example, a step of contacting a cell with a defined cell medium that contains a neurotransmitter, an ErbB3 ligand, and a member of the TGF-β family, can be conducted in any suitable manner, but will be understood to expose the cell to contact with the aforementioned components. For example, the cells may be contacted by incubating (culturing) the cells with the component(s) in adherent culture or in suspension culture. It is understood that the cells contacted with the components in defined medium can be further treated with a cell differentiation environment to stabilize the cells, or to differentiate the cells.

"Support" as used herein in the context of cell culture, refers to media compositions, specific components thereof and culture conditions that are sufficient for the desired growth, viability, pluripotency and/or other characteristics of the cell culture. Thus, a defined medium that supports undifferentiated expansion of hES cells is one in which the cells will grow without differentiation when the hES cells are cultured therein without additional factors, compounds, additives or the like. A compound or factor that supports the expansion of hES cells is one that, when added to the media conditions described, will allow the hES cells to grow.

As used herein, "defined cell culture media," "defined culture media," and "defined media" are used interchangeably to refer to aqueous compositions containing specific proportions, amounts or activities of inorganic and organic components (including biological and bioactive components) that can faithfully be reproduced with substantially similar properties. Defined media may contain proteins, preferably recombinant proteins, provided they can be prepared or purified without significant lot-to-lot or batch-to-batch variability Animal sera are inherently undefined and variable, and therefore defined media does not include serum. However, individual, highly purified serum or other proteins, factors and the like may be included in defined media in an amount or proportion based on mass, molar equivalents or activity (e.g. measurable biological activity).

As used herein, the term "differentiate" refers to the production of a cell type that is more specialized than the cell type from which it is derived. The term therefore encompasses cell types that are partially and terminally differentiated. Differentiated cells derived from hES cells are generally referred to as "hES-derived cells," "hES-derived cell aggregate cultures," "hES-derived single cell suspensions," "hES-derived cell adherent cultures" and the like.

As used herein, the term "substantially" refers to a great extent or degree. For example, "substantially similar" in context can be used to describe a method which is to a great extent or degree similar to another method. However, as used herein, by the term "substantially free", (e.g., "substantially free" or "substantially free from contaminants," or "substantially free of serum" or "substantially free of insulin or insulin like growth factor" or equivalent expressions), it is meant that the solution, media, supplement, excipient or the like, is at least 80%, at least 85%, at least 90%, at least 95%, at least 99% or at least about 100% free of serum, contaminants, insulin or insulin like growth factor. In one embodiment of the invention, there is provided a defined culture medium that contains no serum, or is 100% serum-free, or is substantially free of serum. In contrast, a "substantially similar" composition, process, method, solution, media, supplement, excipient or the like, is at least 80%, at least 85%, at least 90%, at least 95%, or at least 99% similar to the reference composition, process, method, solution, media, supplement, excipient previously described herein, or in a previously described process or method incorporated herein by reference in its entirety.

In certain embodiments of the present invention, the term "enriched" refers to a cell culture that contains more than about 50%, 55%, 60%, 65%, 70%, 75%, 80%, 85%, 90%, or 95% of a desired cell lineage.

As used herein, the term "effective amount" or equivalents expressions, of an agent, such as a compound, refers to that amount of the agent that is sufficient in the presence of the remaining components and conditions to effect the desired result, such as inhibition of pluripotent stem cell growth. In certain aspects of the invention, for example, an effective amount of a compound or growth factor to stabilize a pluripotent stem cell culture is the amount that will result in stabilization of a pluripotent stem cell culture for e.g. greater than one day, one week, one month, two months, three months, four months, five months and/or six or greater months in the absence of a feeder cell and in the absence of serum or serum replacement. In other aspects of the invention, an "effective amount" or equivalents expressions, of an agent, such as a compound, can refer to that concentration of the compound that is sufficient in the presence of the remaining components to effect the stabilization of a pluripotent stem cell culture for greater than for greater than 5, 10, 15, 20, 25, 30 or 40 passages, in the absence of a feeder cell and in the absence of serum or serum replacement. Similarly, this concentration is readily determined by one of ordinary skill in the art.

As used herein, the term "agent" refers to any molecule, compound, and/or substance that produces an effect, such as a biological effect, preferably a desired effect. In certain embodiments, agents of the invention are cytotoxic to or inhibitory of the growth of pluripotent stem cells. In one aspect, cytotoxic or inhibitory agents of the invention are selectively cytotoxic or cytostatic toward pluripotent stem cells as compared to at least one other cells type, which may be a more differentiated cell than a pluripotent stem cell.

"Candidate cytotoxic or inhibitory agents" or "candidate agents" of the invention can be synthetic or naturally occurring, including but not limited to biologicals, biochemicals and chemicals that encompass numerous chemical classes, although frequently they are organic compounds. Often, the candidate agents are small molecule organic compounds, i.e., those having a molecular weight of more than about 50 Da yet less than about 2500 Da, typically less than about 2000 Da, frequently less than about 1500 Da, often less that about 1000 Da and typically about 800 Da or less, include functional chemical groups necessary for structural interactions with polypeptides and/or nucleic acids, and typically include at least an amine, carbonyl, hydroxyl or carboxyl group, typically at least two of the functional chemical groups and more often at least three of the functional chemical groups. The candidate agents can include cyclic carbon or heterocyclic structures and/or aromatic or polyaromatic structures substituted with one or more of the above-identified functional groups. Candidate agents also can be biomolecules such as nucleic acids, peptides, proteins, peptidomimetics, antibodies, ribozymes, RNAi constructs (including siRNA), antisense RNAs, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids, variants, analogs and the like are also contemplated.

Candidate agents are obtained from a wide variety of sources including libraries or collections of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be modified through conventional chemical, physical, and biochemical means. Further, known pharmacologically active agents may be subjected to directed or random chemical modifications such as acylation, alkylation, esterification, amidification, and other methods that will be well known in the art, to produce structural analogs of the agents.

As used herein, the term "express" refers to the transcription of a polynucleotide and/or translation of a polypeptide in a cell, such that levels of the molecule are measurably higher in a cell that expresses the molecule than they are in a cell that does not express the molecule. Methods to measure the expression of a molecule are well known to those of ordinary skill in the art, and include without limitation, Northern blotting, RT-PCR, in situ hybridization, Western blotting, and immunostaining.

As used herein when referring to a cell, cell line, cell culture or population of cells, the term "isolated" refers to being substantially separated from the natural source of the cells such that the cell, cell line, cell culture, or population of cells is capable of being cultured in vitro. In addition, the term "isolating" is used to refer to the physical separation of one or more cells out of a group of two or more cells, where the cells are selected based on a desired characteristic, such as cell morphology and/or the expression of a marker. Isolated cells according to the present invention may or may not be partially, substantially or completely purified from contaminants.

As used herein, "ligand" refers to a chemical that binds to a biological molecule, such as a receptor. As used herein, "agonist" refers to a ligand that binds to a receptor of a cell and triggers a response by the cell, while "antagonist" refers to a ligand that binds to a receptor and inhibits a response of a cell by blocking agonist binding.

A used herein, "standard cell density" refers to a concentration range of pluripotent stem cells typically known to be viable and capable of expansion in culture. For example, hES cells are typically plated at a density of about 30,000 to 60,000 cells/cm$^2$, depending on the growth cycle of the cells or cell line, and yielding about 150,000-350,000 cells/cm$^2$, for example about $2.5 \times 10^6$ to about $5 \times 10^7$ cells per 60 mm dish or about 19.6 cm$^2$. In contrast, "low cell density" refers to e.g. pluripotent stem cells plated at a cell density that is significantly less than the standard cell density. It is well known in the art that cells plated below a certain threshold density may experience a lag in cell division or may fail to survive passaging. Cultures of hES cells plated at about 30,000 or fewer cells per cm2 are considered to be of low cell density.

In certain embodiments, pluripotent stem cells are cultured in a defined medium described herein in the absence and/or presence of extracellular matrix proteins (ECM), e.g., MATRIGEL™. Pluripotent cells cultured in the absence of ECM may contain about 0.5 to 20% human serum (hS) or hS retentate fractions from a 300K and/or 100K MW cut-off spin column (Microcon, Millipore, Billerica, Mass.). hES cell aggregate suspensions can be produced by directly incubating hES cells into the media containing up to 20% hS, for example, 0.2%, 1%, 2%, 5%, 10%, 15%, 20% hS or hS retentate fractions overnight at 37° C. The plating efficiency for the stem cells in the hS or hS retentate fraction containing medium was comparable to that observed for hES cells cultured in DC-HALF as described in PCT/US2007/062755, or cultured in DC-HALF medium using MATRIGEL™ as an ECM, or other similar matrices. Methods for culturing hES cells in a defined media are described in U.S. Patent Publication No. 2009/0104696, Apr. 23, 2009, entitled METHODS AND COMPOSITIONS FOR FEEDER-FREE PLURIPOTENT STEM CELL MEDIA CONTAINING HUMAN SERUM, which is herein incorporated in its entirety by reference.

Still in other embodiments, pluripotent stem cells, either as a monolayer or as an aggregate suspension, are cultured in a medium substantially free of animal serum (e.g., mammalian fetal serum such as fetal bovine serum) and further in the absence of exogenously added fibroblast growth factor (FGF). Such methods are distinguishable from U.S. Pat. No. 7,005,252 to Thomson, which requires culturing hES cells in a medium without animal serum but containing exogenously added growth factors, including FGF.

As used herein, the term "differentiable cell" is used to describe a cell or population of cells that can differentiate into a mature cell, or a progenitor or precursor of a mature cell, or that can participate in the differentiation of cells, e.g., fuse with other cells, that can differentiate into a mature cell. The terms "Progenitor cell" and "lineage-restricted progenitor cell" are used interchangeably herein to refer to multipotent cells, oligopotent, and unipotent cells that are committed to differentiation along a particular pathway. For example, progenitor cells of the endoderm lineage may be capable of differentiating into a variety of endoderm cell types, but do not ordinarily develop into ectoderm, mesoderm or derivatives thereof. In one embodiment, pancreatic endoderm progenitor or epithelium as described herein are progenitor cells capable of further developing into different types of pancreatic hormone secreting cells such as insulin, somatistatin, glucagon, ghrelin, and pancreatic polypeptide secreting cells. Certain adult stem cells are types of progenitor cell.

The invention also contemplates differentiable cells from any source within an animal, provided the cells are differentiable as defined herein. For example, differentiable cells may be harvested from embryos, or any primordial germ layer therein, from placental or chorion tissue, or from more mature tissue such as those containing adult stem cells including, but not limited to adipose, bone marrow, nervous tissue, mammary tissue, liver tissue, pancreas, epithelial, respiratory, gonadal and muscle tissues. In specific embodiments, the differentiable cells are embryonic stem cells. In other specific embodiments, the differentiable cells are adult stem cells or dedifferentiated cells. In still other specific embodiments, the stem cells are placental- or chorionic-derived stem cells.

Of course, the invention contemplates using differentiable cells from any animal capable of generating differentiable cells. The animals from which the differentiable cells are harvested may be vertebrate or invertebrate, mammalian or non-mammalian, human or non-human. Examples of animal sources include, but are not limited to, primates, rodents, canines, felines, equines, bovines and porcines.

As used herein, the term "precursor cell" is a type of lineage restricted, partially differentiated, usually unipotent cell that has lost most or all of the stem cell multipotency. Precursor cells are typically capable of differentiating into only one, two or a few closely related final cell types type). The endocrine precursor cells described there, for example, are capable of differentiating into pancreatic hormone-expressing cells.

As used herein, "definitive endoderm" and "DE" are used interchangeably to refer to a multipotent endoderm lineage cell that can further differentiate into cells of the gut tube or organs derived from the gut tube. In accordance with certain embodiments, the definitive endoderm cells are mammalian cells, and in a preferred embodiment, the definitive endoderm cells are human cells. In some embodiments of the present invention, definitive endoderm cells express certain markers and/or fail to significantly express certain other markers. In some embodiments, one or more markers selected from SOX17, CXCR4, MIXL1, GATA4, HNF3beta, GSC, FGF17, VWF, CALCR, FOXQ1, CMKOR1, CRIP1 and CER are expressed in definitive endoderm cells. In other embodiments, one or more markers selected from OCT4, alpha-fetoprotein (AFP), Thrombomodulin (TM), SPARC, SOX7 and HNF4alpha are not significantly expressed in definitive endoderm cells. Definitive endoderm cell populations and methods of production thereof are also described in U.S. patent application Ser. No. 11/021,618, entitled DEFINITIVE ENDODERM, filed Dec. 23, 2004 (now U.S. Pat. No. 7,510,876) which is herein incorporated by reference in its entirety.

Still other embodiments of the present invention relate to cell cultures and cell aggregates termed "PDX1-negative foregut endoderm cells," foregut endoderm cells" or equivalents thereof. PDX1-negative foregut endoderm cells are multipotent and can give rise to various cells and tissues including but not limited to thymus, thyroid, parathyroid, lungs/bronchi, liver, pharynx, pharyngeal pouches, parts of the duodenum and Eustachian tube. In some embodiments, the foregut endoderm cells express increased levels of SOX17, HNF1-beta, HNF1alpha, FOXA1 as compared to non foregut endoderm cells e.g., definitive endoderm or PDX-positive endoderm which do not appreciably express these markers. PDX1-negative foregut endoderm cells also express low to undetectable levels of PDX1, AFP, SOX7 and SOX1. PDX1-negative foregut endoderm cell populations and methods of production thereof are also described in U.S. patent application Ser. No. 11/588,693, entitled PDX1-EXPRESSING DORSAL AND VENTRAL FOREGUT ENDODERM, filed Oct. 27, 2006 which is incorporated herein by reference in its entirety.

Other embodiments of the present invention relate to cell cultures of "PDX1-positive pancreatic foregut endoderm cells," or "PDX1-positive pre-pancreatic endoderm," or "PDX1-positive pre-pancreatic endoderm progenitors" or equivalents thereof. PDX1-positive pre-pancreatic endoderm cells are multipotent and can give rise to various cells and/or tissues including but not limited to stomach, intestine and pancreas. In some embodiments, the PDX1-positive pre-pancreatic endoderm cells express increased levels of PDX1, HNF6, SOX9 and PROX1 as compared to non pre-pancreatic endoderm cells which do not appreciably express these markers. PDX1-positive pre-pancreatic endoderm cells also express low to undetectable levels of NKX6.1, PTF1A, CPA, and cMYC.

Other embodiments of the present invention relate to cell cultures of "PDX1-positive pancreatic endoderm cells," or "PDX1-positive pancreatic endoderm progenitor cells," or "pancreatic progenitors" or "pancreatic epithelium" or "PE" or equivalents thereof. PDX1-positive pancreatic endoderm progenitor cells are multipotent and can give rise to various cells in the pancreas including but not limited to acinar, duct and endocrine cells. In some embodiments, PDX1-positive pancreatic progenitor cells express increased levels of PDX1 and NKX6.1 as compared to non pre-pancreatic endoderm cells which do not appreciably express these markers. PDX1-positive pancreatic progenitor cells also express low to undetectable levels of PTF1A, CPA, cMYC, NGN3, PAX4, ARX, NKX2.2, INS, GCG, GHRL, SST, and PP.

Alternatively, other embodiments of the present invention relate to cell cultures of "PDX1-positive pancreatic endoderm tip cells," or equivalents thereof. In some embodiments, the PDX1-positive pancreatic endoderm tip cells express increased levels of PDX1 and NKX6.1 similar to PDX1-positive pancreatic progenitor cells, but unlike PDX1-positive pancreatic progenitor cells, PDX1-positive pancreatic endoderm tip cells additionally express increased levels of PTF1A, CPA and cMYC. PDX1-positive pancreatic endoderm tip cells also express low to undetectable levels of NGN3, PAX4, ARX, NKX2.2, INS, GCG, GHRL, SST, and PP.

Yet, other embodiments of the present invention relate to cultures of "pancreatic endocrine precursor cells," "pancreatic endocrine progenitor cells" or equivalents thereof. Pancreatic endocrine progenitor cells are multipotent or unipotent and give rise to mature endocrine cells including alpha, beta, delta and pancreatic polypeptide (PP) cells. In some embodiments, the pancreatic endocrine progenitor cells express increased levels of NGN3, PAX4, ARX and NKX2.2 as compared to other non-endocrine progenitor cell types. Pancreatic progenitor cells also express low to undetectable levels of INS, GCG, GHRL, SST, and PP.

Still other embodiments of the present invention relate to cultures of "pancreatic endocrine cells," "pancreatic hormone secreting cells," "pancreatic islet hormone-expressing cell," or equivalents thereof, which refer to cells that have been derived from a pluripotent stem cell in vitro, e.g. alpha, beta, delta and/or PP cells or combinations thereof. These endocrine cells can be poly-hormonal or singly-hormonal, e.g. expressing insulin, glucagon, ghrelin, somatostatin and pancreatic polypeptide or combinations thereof. These endocrine cells can therefore express one or more pancreatic hormones, and have at least one or some of the functions of a human pancreatic islet cell. Pancreatic islet hormone-expressing cells can be mature or immature. Immature pancreatic islet hormone-expressing cells can be distinguished from mature pancreatic islet hormone-expressing cells based on the differential expression of certain markers, or based on their functional capabilities, e.g., glucose responsiveness in vitro or in vivo. Pancreatic endocrine cells also express low to undetectable levels of NGN3, PAX 4, ARX and NKX2.2.

Cell Types

In some embodiments, a "pluripotent (stem) cell" is used as the starting material for differentiation to endoderm-lineage, or more particularly, to pancreatic endoderm type cells. As used herein, "pluripotent," "pluripotency," "pluripotent cells" and equivalents expressions refer to cells that are capable of both proliferation and self-renewal in cell culture, and differentiation towards a variety of cell populations that include those that exhibit multipotent properties. For example, pluripotent ES cells can give rise to each of the three embryonic cell lineages and are generally considered capable of generating all the cell types of an embryo. Pluripotent cells, however, cannot generally give rise to extra-embryonic tissues such as the amnion, chorion, and other components of the placenta, and may not be capable of producing an entire organism, i.e. pluripotent cells are distinguishable from "totipotent" cells. Pluripotency can be demonstrated by providing evidence of stable developmental potential, to form derivatives of all three embryonic germ layers from the progeny of a single cell and to generate a teratoma after injection into an immunosuppressed mouse. Other indications of pluripotency include expression of genes known to be expressed in pluripotent cells and characteristic morphology, which is readily identifiable by the skilled artisan. The pluripotent cells of the present invention can be derived using any method known to those of skill in the art.

In certain embodiments, the pluripotent stem cells of the present invention used as starting materials for the methods described herein, are stem cells, including hES cells, human embryonic germ (EG) cells, human induced pluripotent stem (iPS) cells, or even parthenogenic cells and the like.

In certain embodiment, when pluripotent cells are utilized, the pluripotent cells have a normal karyotype, e.g., greater than 50%, 55%, 60%, 65%, 70%, 75%, 80%, 85%, 90% or greater than 95% of the pluripotent cell culture of metaphases examined will display a normal karyotype. As used herein, "normal karyotype" refers to the normal or wild type chromosome number, and/or gross morphology.

"Totipotent" as used herein, refers to the ability of a cell to develop into all types of cells, not just the three embryonic cell lineages, including extraembryonic tissues (e.g. placenta) and to give rise to an entire organism (e.g. a mouse or human).

"Self-renewal" refers to the ability of a stem cell to divide and form more stem cells with properties identical to the parent stem cell, thereby allowing the population of stem cells to be replenished indefinitely.

As used herein, "embryonic" refers to a range of developmental stages of an organism beginning with a single zygote and ending with a multicellular structure that no longer includes pluripotent or totipotent cells other than developed gametic cells. In addition to embryos derived by gamete fusion, the term "embryonic" refers to embryos derived by somatic cell nuclear transfer.

In another embodiment of the invention, pluripotent stem cells are not derived or are not immediately derived from embryos, for example, iPS cells are derived from a non-pluripotent cell, e.g., a multipotent cell or terminally differentiated cell, through a process known as "dedifferentiation" or "reprogramming." As used herein, "dedifferentiation" or "reprogramming" refers to the process by which a differentiated cell reverts to a less specialized precursor, progenitor or stem cell state.

Human pluripotent stem cells can also be defined or characterized by the presence of several transcription factors and cell surface proteins including transcription factors Oct4, Nanog, and Sox-2, which form the core regulatory complex ensuring the suppression of genes that lead to differentiation and the maintenance of pluripotency; and cell surface antigens, such as the glycolipids SSEA3, SSEA4 and the keratin sulfate antigens, Tra-1-60 and Tra-1-81.

As used herein, the phrases "induced pluripotent stem cells," "iPS cells," "iPSCs," "reprogrammed cells," or equivalents thereof, refer to a type of pluripotent stem cell artificially prepared from a non-pluripotent cell, typically an adult somatic cell, or differentiated cell, such as a fibroblast, a hematopoietic cell, a myocyte, a neuron, an epidermal cell, or the like. iPS cells can be generated from somatic cells by expressing certain genes or gene products, referred to as reprogramming factors, in the cells. See Takahashi et al. (2007) Cell 131:861-872; Wernig et al. (2007) Nature 448: 318-324; Park et al. (2008) Nature 451:141-146; U.S. Patent Pub. No. 2009/0047263, which are herein incorporated by reference in their entirety. More recently, iPS cells have been generated without the addition of exogenous nucleic acids. See e.g., Zhou et al., (2009) Cell Stem Cell. 4:381-4. Induced pluripotent stem cells are substantially similar to natural human pluripotent stem cells, such as hES cells, in many respects including the expression of certain stem cell genes and proteins, chromatin methylation patterns, doubling time, embryoid body formation, teratoma formation, viable chimera formation, and potency and differentiability. Human iPS cells provide a source of pluripotent stem cells without the associated use of embryos.

As used herein, "multipotency" or "multipotent cell" or equivalents thereof refers to a cell type that can give rise to a limited number of other particular cell types. That is, multipotent cells are committed to one or more embryonic cell fates, and thus, in contrast to pluripotent cells, cannot give rise to each of the three embryonic cell lineages or to extraembryonic cells. Multipotent somatic cells are more differentiated relative to pluripotent cells, but are not terminally differentiated. Pluripotent cells therefore have a higher potency than multipotent cells. For example, potency-determining factors that can reprogram somatic cells or be used to generate iPS cells include, but are not limited to, Oct-4, Sox2, FoxD3, UTF1, Stella, Rex 1, ZNF206, Sox15, Myb12, Lin28, Nanog, DPPA2, ESG1, Otx2 and/or combinations thereof.

One aspect of the present invention includes populations of pluripotent, progenitor or precursor cells that are capable of selectively, and in some aspects selectively reversibly, developing into different cellular lineages when cultured under appropriate conditions. As used herein, the term "population" refers to collection of more than one cell, typically a cell culture.

The term "cell lineage" refers to all of the stages of the development of a particular cell type, from the first cleavage division of an embryo to a completely mature cell (i.e. a specialized cell). However, cell lineage is not limited to cells that develop directly from an embryo, but can also include those that are differentiated e.g. from pluripotent stem cells along a particular line, such as a pancreatic endodermal line. Cells of Stages 1-5 described herein are are included in the pancreatic lineage.

As used herein, the terms "develop", "differentiate", "mature" or "produced from pluripotent cells," "derived from pluripotent cells," "differentiated from pluripotent cells" and equivalent expressions, refer to the production of a differentiated or more specialized cell type e.g. from pluripotent cells in vitro or in vivo, or in the case of endocrine cells matured from transplanted PDX1 pancreatic endoderm cells in vivo as described in PCT International Patent Publication No. WO 2008/013664, titled METHODS OF PRODUCING PANCREATIC HORMONES, which is herein incorporated by reference in its entirety. All refer to the progression of a cell from the stage at which it has the potential to differentiate into at least two different cell lineages, through specialization. and eventually terminal differentiation. Such terms can be used interchangeably for the purposes of the present application. The invention contemplates culture conditions that permit such differentiation to be reversible, such that pluripotency or at least the ability to differentiate into more than one cellular lineage can be selectively regained.

Cytotoxic and Inhibitory Agents of Pluripotent Cells

As used herein, the terms "cytotoxic agent," "inhibitory agent," "cytotoxic and/or inhibitory agent" and equivalent expressions, refer to an agent that kills, inhibits, suppresses, prevents or reduces the growth, proliferation and/or expansion of a cell. In one embodiment, the cytotoxic agent inhibits or prevents growth, proliferation and/or expansion of undifferentiated pluripotent stem cells either in a mixed, heterogeneous cell culture or in a substantially homogenous cell culture consisting of a relatively small percentage of pluripotent cells in the culture. The terms cytotoxic and/or inhibitory agent are not limited to a particular mechanism by which the agent functions physiologically, whether it represses or prevents another molecule from engaging in a reaction for example, or prevents or decreases the rate of a reaction, or decreases, limits, or blocks the action or function of another agent or molecules, e.g., an enzyme or organ. Cytotoxic or inhibitory agents contemplated herein are those that result in killing, preventing, blocking, stopping, reducing or slowing the growth, proliferation and/or expansion of pluripotent stem cells. The invention contemplates that agents that result in cell deterioration and/or death, as well as those that are "cytostatic" or prevent cells from dividing, and furthermore, those agents that reduce growth and/or cell division without completely blocking the same, are all encompassed by the term cytostatic and/or inhibitory agents. Without wishing to be bound by theory, the present invention contemplates that the distinction between cytotoxic, cytostatic and inhibitory can be inherent and/or irreversible, or can be proportional to the dose and may be reversible. Representative cytotoxic or inhibitory agents potentially include those described in the LOPAC1280™ library, preferably those described in Table 4, and even more preferably those agents described in Table 5.

For example, among the candidates for such an agent according to the invention is caffeic acid (3,4-dihydroxycinnamic acid) or caffeic acid phenethyl ester (CAPE), a structural relative of flavonoids. These have been shown to have antiviral, anti-inflammatory, and immunomodulatory properties and have been shown to inhibit the growth of various types of transformed cells. See Grunberger et al. (1988) Experientia 44:230-32; Burke et al. (1995) J. Med. Chem. 38:4171-78; Su et al. (1994) Cancer Res. 54:1865-70; Su et al. (1991) Moi, Carcinog. 4:231-42; Hlandon et al. (1980) Arzneim. Forsch. 30:1847-48; and Guarini et al. (1992) Cell. Mol. Biol. 38:513-27. Although the molecular basis for the many activities attributed to caffeic acid is not well defined, most of the activities inhibited by caffeic acid activate nuclear factor kappa B (NF-κB). See Natarajan et al. (1996) Proc. Natl. Acad. Sci. USA 93:9090-95.

Another selective inhibitory agent is ivermectin (22, 23-dihydroavermectin B1a+22,23-dihydroavermectin B1b), which is a lactone anthelmintic agent derived from avermectins, which are isolated from fermentation products of *Streptomyces avermitilis*. It is a broad-spectrum antiparasitic sold under brand names Stromectol® (U.S.A.), Mectizan® (Canada) and Ivexterm (Mexico). Reports have indicated that ivermectin binds to glutamate-activated chloride channels existing in nerve or muscle cells with a specific and high affinity, causing hyperpolarization of nerve or muscle cells by increasing permeability of chloride ions through the cell membrane.

Still another selective inhibitory agent is chelerythrine chloride, a selective inhibitor of group A and B protein kinase C (PKC) isoforms. It has been reported that apoptosis is the predominant mechanism of chelerythrine-induced cell killing in vitro. See Chmura et al. (2000) Clin. Cancer Res. February 2000 6:737. Preclinical findings by Chmura et al. (2000), suggest that chelerythrine or other similar compounds may be effective against certain human tumors that are otherwise resistant to standard therapeutic regimens. Chmura et al. (2000) demonstrate that treatment with chelerythrine resulted in minimal toxicity.

As used herein, the term "variant" includes homologs, analogs, orthologs, and paralogs, as well as synthetic and naturally occurring species, such as chimeric and fusion polypeptides. Variants of cytotoxic or inhibitory agents, particularly structural analogs, are within the scope of the present invention. In addition, a variant of a reference protein or polypeptide is a protein or polypeptide whose amino acid sequence is at least about 80% identical to the reference protein or polypeptide is encompassed by the term variant. In specific embodiments, the variant is at least about 85%, 90%, 95%, 95%, 97%, 98%, 99% or even 100% identical to the reference protein or polypeptide.

As used herein in the context of small molecule compounds, such as naturally-occurring neurotransmitters and synthetic ligands of neurotransmitter receptors, the term "analog" refers to compounds that share structural and/or functional similarity. Analogs include "structural analogs", which possess structural similarities; and "functional analogs" which are chemically different compounds displaying similar pharmacological properties. For example, it is contemplated that structural and functional analogs of the LOPAC1280™ compounds, or the preferred 176 candidates in Table 4, or the even more preferred 10 candidates in Table 5, or the most preferred candidates in FIG. 11F, are suitable for use in the methods of the present invention.

Culture Media

The compositions and methods of the invention include basal salt nutrient solutions. As used herein, "basal salt nutrient solution" refers to an aqueous solution of salts that provide cells with water and certain bulk inorganic ions essential for normal cell metabolism and maintain intra- and extracellular osmotic balance; carbohydrate as an energy source; and a buffering system to maintain the medium within the physiological pH range. Examples of basal salt nutrient solutions include, but are not limited to, Dulbecco's Modified Eagle's Medium (DMEM), Minimal Essential Medium (MEM), Basal Medium Eagle (BME), RPM1 1640, Ham's F-10, Ham's F-12, α-Minimal Essential Medium (aMEM), Glasgow's Minimal Essential Medium (G-MEM), Iscove's Modified Dulbecco's Medium, or a general purpose medium modified for use with pluripotent cells, such as X-VIVO™ (Lonza) hematopoeitic base media and mixtures thereof. In one particular embodiment, the basal salt nutrient solution is an approximately 50:50 (vol:vol) mixture of DMEM and Ham's F12.

Although a basal salt nutrient solution as described herein is employed to maintain cell growth and viability of pluripotent cells, in other embodiments of the invention, alternative pluripotent stem cell culture media may be used to maintain pluripotency or for differentiation of the pluripotent cells, including but not limited to KSR (Invitrogen), xeno-free KSR (Invitrogen), StemPro® hESC SFM (Life Technologies), mTeSR™1 (StemCell Technologies) and HES cellGRO (Millipore), DMEM and X Vivo™ (Lonza) based media, and the like.

It is contemplated that defined media of the invention can further comprise trace elements. Trace elements can be purchased commercially, for example, from Mediatech. Non-limiting examples of trace elements include but are not limited to salts and compounds comprising, aluminum, chlorine, sulfate, iron, cadmium, cobalt, chromium, germanium, sodium, potassium, calcium, phosphate and magnesium. Specific example of salts and compounds containing trace elements include but are not limited to, $AlCl_3$, $AgNO_3$, $Ba(C_2H_3O_2)_2$, $CdCl_2$, $CdSO_4$, $CoCl_2$, $CrCl_3$, $Cr_2(SO_4)_3$, $CuSO_4$, ferric citrate, $GeO_2$, KI, KBr, LI, molybdic acid, $MnSO_4$, $MnCl_2$, NaF, $Na_2SiO_3$, $NaVO_3$, $NH_4VO_3$, $(NH_4)_6Mo_7O_{24}$, $NiSO_4$, RbCl, selenium, $Na_2SeO_3$, $H_2SeO_3$, selenite•2Na, selenomethionone, $SnCl_2$, $ZnSO_4$, $ZrOCl_2$, and mixtures and further salts thereof. If selenium, selenite or selenomethionone is present, it is at a concentration of approximately 0.002 to approximately 0.02 mg/L. In addition, hydroxylapatite may also be present.

It is contemplated that amino acids can be added to defined media suitable for use in compositions and methods of the present invention. Non-limiting examples of such amino acids are Glycine, L-Alanine, L-Alanyl-L-Glutamine, L-Glutamine/Glutamax, L-Arginine hydrochloride, L-Asparagine-$H_2O$, L-Aspartic acid, L-Cysteine hydrochloride-$H_2O$, L-Cystine 2HCl, L-Glutamic Acid, L-Histidine hydrochloride-$H_2O$, L-Isoleucine, L-Leucine, L-Lysine hydrochloride, L-Methionine, L-Phenylalanine, L-Proline, L-Hydroxyproline, L-Serine, L-Threonine, L-Tryptophan, L-Tyrosine disodium salt dihydrate, and L-Valine. In certain embodiments, the amino acid is L-Isoleucine, L-Phenylalanine, L-Proline, L-Hydroxyproline, L-Valine, and mixtures thereof.

It is also contemplated that defined media can include ascorbic acid. When present, ascorbic acid is typically present at an initial concentration of approximately 1 mg/L to approximately 1000 mg/L, or from approximately 2 mg/L to approximately 500 mg/L, or from approximately 5 mg/L to approximately 100 mg/L, or from approximately 10 mg/L to approximately 100 mg/L or approximately at 50 mg/L.

In addition, the compositions and methods of the invention may also include other components such as serum albumin, transferrin, L-glutamine, lipids, antibiotics, β-mercaptoethanol, vitamins, minerals, ATP and similar components.

Examples of vitamins that may be present include but are not limited to vitamins A, $B_1$, $B_2$, $B_3$, B5, $B_6$, $B_7$, $B_9$, $B_{12}$, C, $D_1$, $D_2$, $D_3$, $D_4$, $D_5$, E, tocotrienols, $K_1$ and $K_2$. One of skill in the art can determine the optimal concentration of minerals, vitamins, ATP, lipids, essential fatty acids, etc., for use with a given cell culture. The concentration of supplements may, for example, be from about 0.001 µM to about 1 mM or more. Specific examples of concentrations at which the supplements may be provided include, but are not limited to about 0.005 µM, 0.01 µM, 0.05 µM, 0.1 µM, 0.5 µM, 1.0 µM, 2.0 µM, 2.5 µM, 3.0 µM 4.0 µM, 5.0 µM, 10 µM, 20 µM, 100 µM, etc. In one specific embodiment, the compositions and methods comprise vitamin $B_6$ and glutamine. In another specific embodiment, the compositions and methods comprise vitamin C and an iron supplement. In another specific embodiment, the compositions and methods comprise vitamin $K_1$ and vitamin A. In another specific embodiment, the compositions and methods comprise vitamin $D_3$ and ATP. In another specific embodiment, the compositions and methods comprise vitamin $B_{12}$ and transferrin. In another specific embodiment, the compositions and methods comprise tocotrienols and β-Mercaptoethanol. In another specific embodiment, the compositions and methods comprise glutamine and ATP. In another specific embodiment, the compositions and methods comprise an omega-3 fatty acid and glutamine. In another specific embodiment, the compositions and methods comprise an omega-6 fatty acid and vitamin $B_1$. In another specific embodiment, the compositions and methods comprise α-linolenic acid and $B_2$.

Certain compositions of the present invention are essentially animal serum-free. As used herein, "essentially" refers to compositions, formulations, methods and the like that are fundamentally or in effect the same as the quantity or quality stated, allowing for minor contaminants and/or insignificant changes. In general, essentially refers to at least about 95%, at least about 96%, at least about 97%, at least about 98%, at least about 99%, at least about 99.5%, or 100% the same. Thus, "essentially serum-free" refers to the absence of animal serum, e.g., fetal serum, or fundamentally or in effect the absence of animal serum in the solutions of the present invention. In certain embodiments, animal serum is not an essential ingredient of the compositions and methods of the present invention. Thus, the presence of non-human animal serum in an essentially animal serum-free compositions should only be attributable to impurities, e.g., from the starting materials or residual animal serum from the primary cell culture. For example, essentially animal serum-free medium or environment can contain less than 5, 4, 3, 2, 1 or 0.5% animal serum. In a specific embodiment of the present invention, the essentially animal serum-free composition does not contain animal serum or serum replacement, or only contains trace amounts of animal serum or serum replacement from the isolation of components of the animal serum or serum replacement that are added to the defined media.

A serum-free defined medium is further described in detail in U.S. application Ser. No. 11/838,054, entitled, COMPOSITIONS AND METHODS USEFUL FOR CULTURING DIFFERENTIABLE CELLS, and filed Aug. 13, 2007; and U.S. application Ser. No. 12/264,760, entitled, STEM CELL AGGREGATE SUSPENSION COMPOSITIONS AND METHODS OF DIFFERENTIATION THEREOF, and filed in Oct. 4, 2008, which are herein incorporated by reference in their entirety.

Insulin and Related Molecules

In one embodiment of the present invention, the compositions and methods are free of exogenous insulin and insulin substitutes. The phrase "exogenous insulin or insulin substitutes" is used herein to indicate insulin or insulin substitutes that is/are intentionally added to the compositions or methods of the present invention. Thus, in certain embodiments of the present invention, the methods and compositions are free of insulin or insulin substitutes that are intentionally supplied. The compositions or methods may, however, not necessarily be free of endogenous insulin. As used herein, "endogenous insulin" indicates that the cultured cells may be producing insulin of their own accord when cultured according to the methods of the present invention. Endogenous insulin may also be used to indicate residual impurities from the primary cell culture or impurities from the starting materials. In specific examples, the compositions and methods of the present contain less than 50, 45, 40, 35, 30, 25, 20, 15, 10, 9, 8, 7, 6, 5, 4, 3, 2, or 1 µg/mL of insulin.

As used herein, the term "insulin" refers to a protein, or variant or fragment thereof, which binds to the insulin receptor at normal physiological concentrations and can induce signaling through the insulin receptor. The term "insulin" encompasses a protein having the polypeptide sequence of native human insulin, or of another mammalian insulin, or of any homologs or variants of these sequences. Additionally, the term insulin encompasses polypeptide fragments (i.e. functional fragments) that are capable of binding to the insulin receptor to induce signaling through the insulin receptor. The term "insulin substitute" refers to any zinc containing compound that may be used in place of insulin to give substantially similar biological effects as insulin. Examples of insulin substitutes include, but are not limited to zinc chloride, zinc nitrate, zinc bromide, and zinc sulfate.

To be clear, insulin-like growth factors are not insulin substitutes or homologs of insulin, as contemplated in the present invention. Accordingly, in another specific embodiment, the compositions and methods of the present invention include the use of at least one insulin-like growth factor (IGF) or a variant or a functional fragment thereof. In other embodiments, the compositions and methods of the present invention are free or substantially free of any exogenous insulin-like growth factors (IGFs). In specific embodiments, the compositions and methods of the present invention contain less than 200, 150, 100, 75, 50, 25, 20, 15, 10, 9, 8, 7, 6, 5, 4, 3, 2, or 1 ng/mL of IGF-1.

As used herein, the term "activator of IGF-1R" refers to mitogens that play a pivotal role in regulating cell proliferation, differentiation, and apoptosis. The effects of an activator of IGF-1R are typically mediated through IGF-1R, although they can be mediated through other receptors. The IGF-1R is also involved in cell transformation induced by tumor virus proteins and oncogene products, and the interaction therebetween is regulated by a group of specific binding proteins (IGFBPs). In addition, a large group of IGFBP proteases hydrolyze IGFBPs, resulting in the release of bound IGFs that then regain the ability to interact with IGF-IR. For the purpose of this invention, the ligands, the receptors, the binding proteins, and the proteases are all considered to be activators of IGF-1R. In one embodiment, the activator of IGF-1R is IGF-1, or IGF-2. In a further embodiment, the activator of IGF-1R is an IGF-1 analog. Non-limiting examples of IGF-1 analogs include LongR3-IGF1, Des(1-3)IGF-1, [Arg$^3$]IGF-1, [Ala$^{31}$] IFG-1, Des(2,3)[Ala$^{31}$]IGF-1, [Leu$^{24}$] IGF1, Des(2,3) [Leu$^{24}$] IGF-1, [Leu$^{60}$]IGF-1, [Ala$^{31}$][Leu$^{60}$]IGF-1, [Leu$^{24}$] [Ala$^{31}$]IGF-1, and combinations thereof. In a further embodiment, the IFG-1 analog is LongR3-IGF1, which is a recombinant analog of human insulin growth factor-1. It is contemplated that LongR3-IGF1 is initially present at a concentration of approximately 1 ng/mL to approximately 1000 ng/mL, typically approximately 5 ng/mL to approximately 500 ng/mL, frequently approximately 50 ng/mL to approximately 500 ng/mL, often approximately 100 ng/mL to approximately 300 ng/mL, or most often at a concentration of approximately 100 ng/mL.

Growth Factors

In certain embodiments, the compositions and methods of the present invention include transforming growth factor beta (TGF-β) or a TGF-β family member or variants or functional fragments thereof or agents that are activators of a TGF receptor. As used herein, the term "member of the TGF-β family" or the like refers to growth factors that are generally characterized by one of skill in the art as belonging to the TGF-β family, either due to homology with known members of the TGF-β family, or due to similarity in function with known members of the TGF-β family. In particular embodiments of the invention, if the member of the TGF-β family is present, the TGF-β family member or variant or functional fragment thereof activates SMAD 2 or 3. In certain embodiments, the member of the TGF-β family is selected from the group consisting of Nodal, Activin A, Activin B, TGF-β, bone morphogenic protein-2 (BMP2), GDF-8, GDF-11 and bone morphogenic protein-4 (BMP4) to name a few. In one embodiment, the member of the TGF-β family is selected from Activin A, Activin B, Nodal, GDF-8 and GDF-11. The use of TGF-β family of growth factors to differentiate pluripotent cells is described in detail in U.S. application Ser. No. 12/132, 437, entitled GROWTH FACTORS FOR PRODUCTION OF DEFINITIVE ENDODERM, and filed Jun. 3, 2008, which is herein incorporated by reference in its entirety.

In additional embodiments of the present invention, the compositions and methods of the present invention are free of activators of FGF receptors. As used herein, the term "activator of an FGF receptor" refers to growth factors that are generally recognized by one of skill in the art as belonging to the FGF family, either due to homology with known members of the FGF family, or due to similarity in function with known members of the FGF family. In certain embodiments, the activator of an FGF receptor is an FGF, such as, but not limited to α-FGF and FGF2. In particular embodiments, the compositions and methods are free of exogenous FGF2. The phrase "exogenous FGF2" is used herein to indicate fibroblast growth factor 2, i.e., basic FGF that is intentionally added to the compositions or methods of the present invention. Thus, in certain embodiments of the present invention, the methods and compositions are free of intentionally supplied FGF2. The compositions or methods may, however, not necessarily be free of endogenous FGF2. As used herein, "endogenous FGF2" indicates that the cultured cells may be producing FGF2 of their own accord when cultured according to the methods of the present invention. "Endogenous FGF2" may also be used to indicate residual impurities from the primary cell culture or impurities from the starting materials. In specific examples, the compositions and methods of the present contain less than 10, 9, 8, 7, 6, 5, 4, 3, 2, or 1 ng/mL of FGF2.

It is contemplated, however, that the compositions and methods of the invention can include at least one activator of an FGF receptor, including any of the FGF polypeptides, functional fragments thereof or variants thereof. It is contemplated that if FGF2 is present, it is initially present at a concentration of approximately 0.1 ng/mL to approximately 100 ng/mL, typically approximately 0.5 ng/mL to approximately 50 ng/mL, frequently approximately 1 ng/mL to approximately 25 ng/mL, often approximately 1 ng/mL to approximately 12 ng/mL, or most often at a concentration of approximately 8 ng/mL. In another specific embodiment, the compositions and methods of the invention can include at least one activator of an FGF receptor, other than FGF2. For example, the compositions and methods of the present invention may comprise at least one of FGF-7, FGF-10 or FGF-22 or variants or functional fragments thereof. In specific embodiments, a combination of at least two of FGF-7, FGF-10 and FGF-22, or variants or functional fragments thereof, are present. In another embodiment, all three of FGF-7, FGF-10 and FGF-22, or variants or functional fragments thereof, are present. It is contemplated that if any of FGF-7, FGF-10 or FGF-22 or variants or functional fragments are present, each is initially present at a concentration of approximately 0.1 ng/mL to approximately 100 ng/mL, more specifically from approximately 0.5 ng/mL to approximately 50 ng/mL, more specifically from approximately 1 ng/mL to approximately 25 ng/mL, more specifically from approximately 1 ng/mL to approximately 12 ng/mL, or most specifically at a concentration of approximately 8 ng/mL.

In certain additional embodiments, the compositions and methods of the present invention include serum albumin (SA). In specific embodiments, the SA is either bovine SA (BSA) or preferably human SA (HAS). In still more specific embodiments, the concentration of the SA is more than about 0.2%, weight to volume (wt/vol), but less than about 10% wt/vol. In even more specific embodiments, the concentration of SA is more than about 0.3%, 0.4%, 0.5%, 0.6%, 0.7%, 0.8%, 0.9%, 1.0%, 1.2%, 1.4%, 1.6%, 1.8%, 2.0%, 2.2%, 2.4%, 2.6%, 2.8%, 3.0%, 3.2%, 3.4%, 3.6%, 3.8%, 4.0%, 4.2%, 4.4%, 4.6%, 4.8%, 5.0%, 5.2%, 5.4%, 5.6%, 5.8%, 6.0%, 6.2%, 6.4%, 6.6%, 6.8%, 7.0%, 7.2%, 7.4%, 7.6%, 7.8%, 8.0%, 8.2%, 8.4%, 8.6%, 8.8%, 9.0%, 9.2%, 9.4%, 9.6% and 9.8% (wt/v).

Rho Kinase

Cellular regulation can be effected through the transduction of extracellular signals across the membrane that in turn, modulate biochemical pathways within the cell. Rho kinases, are a class of enzymes, which if inhibited can have relevance to the treatment of human disease, including diabetes, cancer, and a variety of inflammatory cardiovascular disorders and AIDS.

The Rho kinase family of small GTP binding proteins contains at least 10 members including Rho A-E and G, Rac 1 and 2, Cdc42, and TC10. The inhibitor is often referred to as ROK or ROCK inhibitors, and these names are used interchangeably herein. The effector domains of RhoA, RhoB, and RhoC have the same amino acid sequence and appear to have similar intracellular targets. Rho kinase operates as a primary downstream mediator of Rho and exists as two isoforms: α (ROCK2) and β (ROCK1). The typical Rho kinase family protein has a catalytic (kinase) domain in its N-terminal domain, a coiled-coil domain in its middle portion, and a putative pleckstrin-homology (PH) domain in its C-terminal domain. The Rho-binding domain of ROCK is localized in the C-terminal portion of the coiled-coil domain and binding of the GTP-bound form of Rho results in enhancement of kinase activity. The Rho/Rho-kinase-mediated pathway plays an important role in the signal transduction initiated by many agonists, including angiotensin II, serotonin, thrombin, endothelin-1, norepinephrine, platelet-derived growth factor, ATP/ADP and extracellular nucleotides, and urotensin II. Through the modulation of its target effectors/substrates Rho kinase plays an important role in various cellular functions including smooth muscle contraction, actin cytoskeleton organization, cell adhesion and/or motility and gene expression.

Hence, in other embodiments of the invention, agents that promote and/or support cell survival are added to various cell culture media, including but not limited to for example, Rho-kinase inhibitors Y-27632, Fasudil, and H-1152P and ITS (insulin/transferrin/selenium; Gibco). These cell survival agents function, in part, by promoting re-association of dissociated hES cell or hES-derived cultures, e.g., foregut endoderm, pancreatic endoderm, pancreatic epithelium, pancreatic endoderm progenitor populations and the like, particularly dissociated pancreatic endoderm and pancreatic progenitor populations. Increase in survival of hES or hES-derived cells have been achieved independently of whether the cells were produced from cell aggregates in suspension or from adherent plate cultures (with or without extracellular matrix, with or without animal serum, with or without fibroblast feeder cells). Increased survival of these cell populations facilitates and improves purification (e.g. using a cell-sorter) and, therefore, allows improved recovery of the cells. Use of Rho kinase inhibitors such as Y27632 may allow for expansion of hES-derived cell types as well, by promoting survival during serial passaging of dissociated single cells or during recovery from cryogenic preservation. Although, Rho kinase inhibitors such as Y27632 have been tested on hES and hES-derived cell cultures, Rho kinase inhibitors can be applied to other cell types, for example, in general, epithelial type cells including but not limited to intestinal, lung, thymus, kidney as well as neural cell types like pigmented retinal epithelium.

Cell Culture Methods

Cell culture environments and methods of the present invention include plating the cells in an adherent culture. As used herein, the terms "plate," "plated" and "plating" refer to any process that allows a cell to be grown in adherent culture. As used herein, the term "adherent culture" refers to a cell culture system whereby cells are cultured on a solid surface, such as culture vessel, which may in turn be coated with an insoluble substrate that may in turn be coated with another surface coat of a substrate, such as those listed below, or any other chemical or biological material that allows the cells to adhere, proliferate and/or be stabilized in culture. The cells may or may not tightly adhere to the solid surface or to the substrate.

Cell Substrates, Feeder Layers and Conditioned Media

The substrate for the adherent culture may include any one or a combination of polyornithine, laminin, poly-lysine, purified collagen, gelatin, fibronectin, tenascin, vitronectin, entactin, heparin sulfate proteoglycans, MATRIGEL™, poly glycolytic acid (PGA), poly lactic acid (PLA), and poly lactic-glycolic acid (PLGA). Furthermore, the substrate for the adherent culture may comprise a matrix laid down by a feeder layer, or laid down by cells (e.g. pluripotent human cells) or a cell culture thereof. As used herein, the term "extracellular matrix" encompasses solid substrates such as but not limited to those described above, as well as the matrix laid down by a feeder cell layer or by a cell (e.g. a pluripotent human cell) or cell culture or that made from lysed fibroblast feeder cells. In one embodiment, the cells are plated on MATRIGEL™-coated plates. In another embodiment, the cells are plated on fibronectin-coated plates. In another embodiment, human serum can be placed in the medium for up to 24 hours before the growth media contacts the cells, approximately simultaneous to when the growth media contacts the cells, or sometime after the growth media contacts the cells. See, e.g. U.S. Patent Publication No. 2009-0104696, filed Oct. 19, 2007, entitled "METHODS AND COMPOSITIONS FOR FEEDER-FREE PLURIPOTENT STEM CELL MEDIA CONTAINING HUMAN SERUM, which is incorporated herein by reference in its entirety.

The compositions and methods of the present invention contemplate that pluripotent and differentiable cells may be cultured in conditions that are essentially free of a feeder cell or feeder layer. As used herein, a "feeder cell" or "fibroblast feeder cell" or equivalent expressions thereof, is a cell that grows in vitro, that is co-cultured with a target cell or cell of interest. As used herein, a "feeder cell layer" is used interchangeably with the term "feeder cell" or "fibroblast feeder cell" or "fibroblast feeder layer" or "feeders" or equivalent expressions thereof. As used herein, the term "essentially free of a feeder cell" refers to tissue culture conditions, in particular pluripotent stem cell (e.g. hES or iPS cell) culture conditions, such as those described herein, that do not contain any feeder cells, or that contain a de minimus number of feeder cells, or matrices made from feeder cells or extracellular matrices, natural or synthetic, used to coat a culture vessel. "De minimus," in the context of feeder cells, refers to the minimal number of feeder cells that may be inadvertently and in some cases unavoidably carried over to the instant culture conditions from previous culture conditions where the cells may have been cultured on feeder cells.

In certain aspects, the present invention pluripotent stem cells may be cultured without a need for any type of feeder cell or feeder layer, whether created by cells or proteins lysed from those cells, or the use of other types of surface coatings such as a coating of human serum.

In one embodiment of the present invention, cells are grown in conditioned medium obtained from a feeder cell, which stabilizes the cell in its current state of differentiation. In another embodiment, the defined medium used herein is a non-conditioned medium, which is a medium that is not obtained from a feeder cell.

As used herein, the term "stabilize," when used in reference to the differentiation state of a cell or culture of cells, indicates that the cells will continue to proliferate over multiple passages in culture, and preferably indefinitely in culture, where most, if not all, of the cells in the culture are of the same differentiation state. In addition, when the stabilized cells divide, the division typically yield cells of the same cell type or yields cells of the same differentiation state. A stabilized cell or cell population in general, does not further differentiate or de-differentiate if the cell culture conditions are not altered and the cells continue to be passaged without being allowed to overgrow. In one embodiment, the cell that is stabilized is capable of proliferation in the stable state indefinitely, or for at least more than 2 passages. In more specific embodiments, the cells are stable for more than 3 passages, 4 passages, 5 passages, 6 passages, 7 passages, 8 passages, 9 passages, more than 10 passages, more than 15 passages, more than 20 passages, more than 25 passages, or more than 30 passages. In certain embodiments, the cell is stable for greater than approximately 1 month, 2 months, 3 months, 4 months, 5 months, 6 months, 7 months, 8 months, 9 months, 10 months, or 11 months of continuous passaging. In another embodiment, the cell is stable for greater than approximately 1 year of continuous passaging. In one embodiment, pluripotent stem cells are maintained in culture in a pluripotent state by routine passage in a defined medium until it is desired that they be differentiated. As used herein, the term "proliferate" refers to an increase in the number cells in a cell culture.

In one embodiment, differentiable cells are contacted with at least one of the compositions of the invention in the absence of animal fetal serum or serum replacement, and in the absence of a feeder cell layer or matrices, natural or synthetic, such that the cells are maintained in an undifferentiated state for at least one month. Pluripotency can be determined through characterization of the cells with respect to morphology, surface markers, transcriptional markers, karyotype, and ability to differentiate to cells of the three germ layers. These characteristics are well known to those of ordinary skill in the art.

Suspension Culture

As used herein, the term "embryoid bodies" or "EBs" or "aggregate bodies" or equivalents expressions, refer differentiated cell types in suspension cultures in undefined media or are differentiated via non-directed protocols towards multiple germ layer tissues. Embryoid bodies are distinguishable from pluripotent stem cell aggregates in suspension for example by morphological criteria. The determination of when embryoid bodies exist in a culture of embryonic stem cells is routinely made by persons of skill in the art. For example, floating masses of about 20 cells or more depending on the culture conditions are considered to be EBs. See e.g., Schmitt et al. (1991) Genes Dev. 5:728-740; Doetschman et al. (1985) J. Embryol. Exp. Morph. 87:27-45. The term also refers to equivalent structures derived from primordial germ cells, which are primitive cells extracted from embryonic gonadal regions; see e.g., Shamblott, et al. (1998) Proc. Natl. Acad. Sci. USA 95:13726. Primordial germ cells, sometimes also referred to in the art as EG cells or embryonic germ cells, when treated with appropriate factors, form pluripotent ES cells from which embryoid bodies can be derived; see e.g., U.S. Pat. No. 5,670,372; and Shamblott, et al., supra.

Various methods for making embryoid bodies exist, e.g. spin embryoid bodies as described by Ng et al. (2008) (Nature Protocols 3:468-776), and embryoid bodies made from single cell suspensions plated onto micro-patterned extracellular matrix islands as described in Bauwens et al. (2008), supra. However, these methods are cost-prohibitive and less efficient for large scaled production (manufacturing) of hES cells and hES-derived cells because they require too many steps before scale-up production can actually commence. For example, the protocol of Bauwens et al. requires that hES cells are seeded on growth factor reduced MATRIGEL™ before the cells can be selected to initiate a suspension culture. The time and cost of this method makes it cumbersome because customized micro-patterned tissue culture plates are required. Additionally, the method employed by Ng et al. cannot be cost-effectively scaled for manufacturing of hES cells and hES-derived cells because it requires the use of centrifuges to create uniform embryoid bodies. Lastly, in all these methodologies, the cell aggregates are not made from single cell suspensions of pluripotent stem cells, as are the single cell aggregate suspension cultures described herein.

Embryoid bodies can also be created by exposing aggregates of undifferentiated ES cells to non-directed differentiation signals, such as 20% fetal bovine serum. The result of this non-directed methodology is a mixture of cell types that is intended to mimic normal embryonic development in vitro. While this approach is useful at the basic research level for examining embryonic development, it is not amenable to any large-scale manufacturing process suitable for producing material for cell therapy, where cell yield, population identity, population purity, batch consistency, safety, cell function and cost of goods are primary concerns. Moreover, regardless of any enrichment strategies employed to purify a given cell type from an embryoid body, the differentiation protocol does not provide a directed approach that will generate a large, homogenous population of a single cell type. Subsequently, contaminant populations will always be present and may predominate, which will hamper any attempt to purify a specific population.

All previously reported work on creating and differentiating aggregates of pluripotent stem cells has one or more of the following components in their methodology: 1) use of mouse rather than human ES cells; 2) forced aggregation protocols that rely on centrifugation to aggregate cells rather than normal cell adhesion processes; 3) aggregation of cell chunks under static conditions; 4) non-single cell dissociation or scraping of cells off surfaces to create aggregates; and 5) non-direct differentiation of cell aggregates using 15-20% fetal calf serum (FCS), resulting in the formation of embryoid bodies and cell types of all germ layers. To applicants' knowledge, the only reported study in which 15-20% FCS is not used to differentiate embryoid bodies involves a protocol where cell aggregates were formed by forced aggregation and then the formed aggregates were immediately differentiated using media appropriate for mesoderm (Ng et al., Blood (2005) 106:1601). However, in this report, the researchers transferred the embryoid bodies to non-aggregate adherent culture after 10-12 days in static aggregate culture, making comparisons to the current application irrelevant.

In contrast, single cell aggregates described herein are produced by an approach that 1) dissociates human pluripotent stem cells (e.g., human ES cells or human IPS cells) to single cells and then creates aggregates by rotational culture at shear rates optimized for improved control of aggregate diameter and cell survival; and 2) allows direct differentiation of the pluripotent stem cell aggregates, for example, to definitive endoderm, and subsequently to other endoderm-lineage cell types. See U.S. Pat. Publication Nos. 2008/0268534 (filed Feb. 23, 2007, entitled "COMPOSITIONS AND METHODS USEFUL FOR CULTURING DIFFERENTIABLE CELLS"); 2008/0113433 (filed Aug. 13, 2007, entitled "COMPOSITIONS AND METHODS USEFUL FOR CULTURING DIFFERENTIABLE CELLS"); 2010/0112691 (filed Nov. 4, 2008, entitled "STEM CELL AGGREGATE SUSPENSION COMPOSITIONS AND METHODS OF DIFFERENTIATION THEREOF") the entire disclosures of which are incorporated herein by reference. This differentiation protocol generates definitive endoderm and pancreatic lineage populations with high efficiency and minimal contaminant populations. Moreover, this approach to pluripotent stem cell aggregation and differentiation does not create embryoid bodies, in direct contrast to all other published research.

In one particular embodiment, undifferentiated as well as differentiable cells are expanded in a suspension culture, using the cell culture media of the present invention. In another particular embodiment, differentiable cells can be maintained and expanded in suspension, i.e., they remain undifferentiated or are prevented from further differentiating. The terms "expand," "expanded" and "expansion" in the context of cell culture are used as they are in the art, and refer to cellular proliferation and increase in the number of cells, preferably increase in number of viable cells. In a specific embodiment, the cells are expanded in suspension by culturing for more than about one day, i.e., about 24 hours. In a more specific embodiment, the cells are expanded in suspension by culturing for at least 1, 2, 3, 4, 5, 6, 7 days or more, or at least 2, 3, 4, 5, 6, 7, 8 weeks or more.

Aggregate Suspension Culture

A variety of methods of making cell aggregates are known in the art such as, for example, the "hanging drop" method wherein cells in an inverted drop of tissue culture medium sink to the bottom of the drop where they aggregate; shaking cell suspensions in a laboratory flask; and various modifications of these techniques. See e.g., Timmins, et al. (2004) Angiogenesis 7:97-103; Dai et al., (1996) Biotechnol. Bioengineering 50:349-356; Foty et al. (1996) Development 122 :1611-20; Forgacs et al. (2001) J. Biophys. 74 :2227-34 (1998); Furukawa et al. (2001) Cell Transplant. 10:441-445;

Glicklis et al. (2004) Biotechnol. Bioengineering 86: 672-80; Carpenedo et al. (2007) Stem Cells 25: 2224-34; and Korff et al., (2001) FASEB J. 15: 447-57, which are herein incorporated by reference in their entirety. More recently, cell aggregates have been formed by scraping micropatterned colonies into suspension, centrifuging colonies out of microtiter plates and into suspension or using pipets to dislodge and suspend colonies grown in patterned microwells (Ungrin et al., (2008) PLoS ONE 3(2), 1-12; Bauwens et al. (2008) Stem Cells, Published online Jun. 26, 2008). Although such methods can be used to produce cell aggregates described herein, the cell aggregates produced herein are optimized for synchronous directed-differentiation as described in d'Amour et al. 2006, supra. Also, unlike these other methods, the methods for producing the cell aggregates in suspension described herein are amenable to large scale manufacturing.

The term "suspension" as used in the context of cell culturing, is used as it is in the art. Namely, cell culture suspensions are cell culture environments where the cells or cell aggregates do not adhere to a surface, such as a culture vessel. One of skill in the art will be familiar with suspension culture techniques, including, but not limited to, the use of equipment such as flow hoods, incubators and/or other equipment used to keep the cells in constant motion, e.g., rotator platforms, shakers, etc, if necessary. As used herein, cells are "in motion" if they are moving, or if their immediate environment is moving relative to the cells. If the cells are kept "in motion," the motion will, in one embodiment, be a "gentle motion" or "gentle agitation" that is designed to avoid or prevent exposing the cells to shear stress.

In general, the cell medium compositions of the present invention are refreshed at least once every day, but the medium can be changed more often or less often, depending of the specific needs and circumstances of the culture and the type of culture vessel, e.g., a closed loop bioreactor system. In vitro, cells are usually grown in culture media in a batch mode and exposed to various media conditions. In some embodiments of the invention, the cells in a culture can be maintained as either adherent cultures or as cell aggregates in suspension, which are maintained in contact with a surrounding culture medium; and the waste media being replaced periodically. In general, the culture medium may be refreshed about every 1, 2, 3, 4, 5, 6, 7, 8, 9, 10, 11, 12, 13, 14, 15, 16, 17, 18, 19, 20, 21, 22, 23 or 24 hours, or any fraction thereof. In additional examples, the medium may be refreshed less often such as, but not limited to, every 1.1, 1.2, 1.3, 1.4, 1.5, 1.6, 1.7, 1.8, 1.9 or every 2 or more days, or any time frame in between.

In another embodiment of the invention, large scale up manufacturing processes are employed, which may include growth, culture and differentiation of cells in large bioreactors using perfusion methods to refresh the medium to prevent degradation of growth factors and other agents which have to be replaced frequently. Perfusion may also be used as a means to deplete waste products from the culture media over a period of time. For example, U.S. Pat. No. 5,320,963 describes a bioreactor for perfusion culture of suspension cells. U.S. Pat. No. 5,605,822 describes a bioreactor system, employing stromal cells to provide growth factors, for growth of cells in culture by perfusion. U.S. Pat. No. 5,646,043 describes growth of cells by continuous and periodic perfusion including media compositions for growth of cells. U.S. Pat. No. 5,155,035 describes a bioreactor for suspension culture of cells by fluid media rotation. These references are all incorporated herein by reference in their entirety.

In general, the cells that are cultured in the medium compositions of the present invention are "split" or "passaged" every week or so, but the cells can be split more often or less often, depending on the specific needs and circumstances of the suspension culture. For example, the cells may be split every 1, 2, 3, 4, 5, 6, 7, 8, 9, 10, 11, 12, 13, 14 or more days, or any time frame in between. As used herein, the term "split" or "passaged" in the context of cell culture is used as it is in the art. Namely, cell culture splitting, or passaging, is the collection of cells from a previous culture and subsequent transfer ("seeding") of a smaller number of collected (harvested) cells into a new cell culture vessel of the same size. The skilled artisan will recognize that "splitting" or "passaging" also encompasses transferring all or a portion of the harvested cells to a larger vessel, or dividing them into several culture vessels. In general, passaging cells allows the cells to continue to grow in a healthy cell culture environment. One of skill in the art will be familiar with the process and methods of cell culture passaging, which may, but do not necessarily, involve the use of enzymatic or non-enzymatic methods that may be used to disaggregate cells that have clumped together during their growth expansion.

The embodiments described herein provide methods for large-scale manufacturing of proliferating and/or differentiating pluripotent stem cells (e.g. hES and iPS cells) by maintaining a low shear environment, which thereby maintains operating cell density in the system and minimizes fluid shear stresses. In particular, the present invention encompasses methods for maintaining a low shear environment in a eukaryotic cell manufacturing scale-up system by culturing a cell suspension in a 60 mm dish, 6-well plate, a rotating bottle, a bioreactor (e.g., large and spinner flasks), a vessel, closed loop systems and the like. Alternatively, continuous perfusion systems for culturing cells requires agitation or movement in the bioreactor or vessel to provide suspension of the cells, oxygenation and a supply of fresh nutrients, e.g., for growth and/or differentiation. To keep cells in suspension, bioreactor vessels typically use one or more movable mechanical agitation devices that are also a potential source of shear stress.

Establishing and maintaining a constant, optimized agitating shear rate is important for maintaining cell growth and viability. For example increased shear rate is deleterious in the following aspects: (1) excessive shear increases energy consumption, (2) excessive shear interferes with diffusion at the membrane surface, (3) excessive shear can deprive certain compounds of their bioactivities, and (4) excessive shear can deform cell membranes beyond the threshold bursting tension leading to cell lysis. It therefore is desirable to maintain shear within an optimal range of 5 to 500 $\sec^{-1}$, depending on the diameter of the cell aggregate and the sensitivity of the particular cell line to single cell dissociation and shear. Exemplary shear rates produced by configurations useful in the methods of the invention are shown in Example 17 of U.S. patent application Ser. No. 12/264,760 (which is incorporated by reference herein in its entirety) for aggregate diameters between 100-200 μm and rotation speeds between 60-140 rpm for a 6-well dish. These values estimate the time averaged shear stress that occurs in the bulk fluid during rotation. However, it is expected that the shear stress at the wall of the vessel will be higher due to boundary effects.

Still, other examples of means or devices for generating a gently agitated cell suspension exist and are well known to one skilled in the art including impellers, such as propellers, or other mechanical means, bladders, fluid or gas flow-based means, ultrasonic standing wave generators, rocking or rotating platforms or combinations thereof which produce a cell suspension. In the methods of the invention, a rotating platform is an exemplary means for suspending the cells in the media when cells are in 6-well plates, generating a shear rate of less than 400 $\sec^{-1}$. Regardless of rotator type or mechanism for generating agitated mixed fluid suspensions, the estimated time-averaged shear rate and shear stress in the bulk fluid provides a normalizing factor by which all fluid mixing devices can be related. While the flow regimes amongst the devices may vary in their profile and extent of laminar or turbulent flow, shear calculations provide a basis for equating flow in devices that produce mixing by different mechanisms. For example, for a 125 mL spinner flask with an impeller diameter of 4 cm, a vessel width of 6.4 cm, an impeller angle of 90 degrees, and an impeller width of 0.1 cm, a impeller rotation speed of 135 rpm will generate the same time-average shear rate and shear stress in the bulk fluid as 6-well dish with 5 mL media rotating at 100 rpm for aggregates of 100 μm in diameter.

It is contemplated that differentiable cells can be passaged using enzymatic, non-enzymatic, or manual dissociation methods prior to and/or after contact with the defined medium of the invention. Manual passaging techniques have been well described in the art, such as in Schulz et al. (2004) Stem Cells, 22:1218-38. Although mechanical passaging does not involve any additional substances, it is not efficient for large-scale manufacturing of pluripotent stem cells or many cells derived thereof. For example, in bioreactors or large flasks, use of enzymes is contemplated, using for example GMP-collagenase. Non-limiting examples of enzymatic dissociation methods include the use of proteases such as trypsin, collagenase, dispase, and ACCUTASE™ (Life Technologies, Carlsbad, Calif.). In one embodiment, ACCUTASE™ is used to passage the contacted cells. When enzymatic passaging methods are used, the resultant culture can comprise a mixture of singlets, doublets, triplets, and clumps of cells that vary in size depending on the enzyme used. A non-limiting example of a non-enzymatic dissociation method is a cell dispersal buffer. The choice of passaging method is influenced by the choice of extracellular matrix, if one is present, and is easily determined by one of ordinary skill in the art.

The disaggregation solution used in the methods of the present invention can be any disaggregation solution capable of breaking apart or disaggregating the cells into single cells, without causing extensive toxicity to the cells. Examples of disaggregation solutions include, but are not limited to, trypsin, ACCUTASE™, 0.25% Trypsin/EDTA, TrypLE, or VERSENE™ (EDTA) and trypsin. The methods of the present invention need not result in every cell of a confluent layer or suspension being disaggregated into single cells, provided that at least a few single cells (or more preferably most cells) are disaggregated and capable of being re-cultured.

Either at the beginning of culture, or after passaging, the differentiable cells can be seeded at any density, including a single cell in a culture chamber. The cell density of the seeded cells may be adjusted depending on a variety of factors, including but not limited to the use of adherent or suspension cultures, the specific recipe of the cell culture media used, the growth conditions and the contemplated use of the cultured cells. Examples of cell culture densities that may be suitable for use in the methods of the invention include, but are not limited to, $0.01 \times 10^5$ cells/mL, $0.05 \times 10^5$ cells/mL, $0.1 \times 10^5$ cells/mL, $0.5 \times 10^5$ cells/mL, $1.0 \times 10^5$ cells/mL, $1.2 \times 10^5$ cells/mL, $1.4 \times 10^5$ cells/mL, $1.6 \times 10^5$ cells/mL, $1.8 \times 10^5$ cells/mL, $2.0 \times 10^5$ cells/mL, $3.0 \times 10^5$ cells/mL, $4.0 \times 10^5$ cells/mL, $5.0 \times 10^5$ cells/mL, $6.0 \times 10^5$ cells/mL, $7.0 \times 10^5$ cells/mL, $8.0 \times 10^5$ cells/mL, $9.0 \times 10^5$ cells/mL, or $10.0 \times 10^5$ cells/mL, or more, have been cultured in suspension with good cell survival, or any value in between.

In addition to the above, as used herein, the term "operating cell density" or "operational cell density" or equivalents expressions refers to that cell density at which a cell culture protocol or manufacturing process or system will be operated to obtain the production of a proliferating or differentiating hES cell culture. Such cell densities are those at which nutrients such as vitamins, minerals, amino acids or metabolites, as well as environmental conditions such as oxygen tension, that are supplied to the system are sufficient to maintain cellular viability. Alternatively, such cell densities are those at which waste products can be removed from the system at a rate sufficient to maintain cellular viability. Such cell densities can be readily determined by one of ordinary skill in the art.

Furthermore, pluripotent stem cells can also be grown in 96-well culture devices that provide real-time measurements of impedance, which can be used to measure cell proliferation and viability using the RT-CEST™ methods from ACEA Biosciences, Inc. (world wide web at aceabio.com) or other similar cell assay research tools. Such an approach enables a label-free identification and quantification of subtle or immediate effects on differentiable cells, as well as measurements of proliferation, apoptosis and changes to morphology, in real time.

Differentiation of Pluripotent Stem Cells along Endoderm-Lineage and Pancreatic Endoderm-Lineage lines: Summary of the Production of Stages 1 to 4 Cells The methods for production of certain endoderm-lineage and pancreatic endoderm-lineage cells are provided herein, and discussed elsewhere in related applications such as U.S. patent application Ser. No. 11/773,944, entitled METHODS OF PRODUCING PANCREATIC HORMONES, filed Jul. 5, 2007, which is a continuation-in-part of U.S. patent application Ser. No. 11/681,687, entitled ENDOCRINE PRECURSOR CELLS, PANCREATIC HORMONE-EXPRESSING CELLS AND METHODS OF PRODUCTION, filed Mar. 2, 2007; which are incorporated herein by reference in their entirety.

Briefly, the directed differentiation methods described herein for pluripotent stem cells, for example, hES and iPS cells, can be divided into at least four or five stages. Stage 1 is the production of definitive endoderm from pluripotent stem cells and takes about 2 to 5 days, typically 2 or 3 days. Pluripotent stem cells are first suspended in media comprising RPMI (without animal serum or with very low levels of animal serum, e.g., 0.2%); a TGFβ superfamily member growth factor, such as Activin A, Activin B, GDF-8 or GDF-11 (at least 100 ng/mL); a Wnt family member or Wnt pathway activator, such as Wnt3a (at least 25 ng/mL); and optionally, a rho-kinase or ROCK inhibitor, such as Y-27632 (about 10 μM) to enhance growth, survival and proliferation as well as promote cell-cell adhesion for about 24 hours. Alternatively, small amounts of ITS (Invitrogen, Carlsbad, Calif.) at about 1:5000 can also be used, while still maintaining low insulin and serum content in the cell culture media. See also U.S. patent application Ser. No. 12/132,437, entitled GROWTH FACTORS FOR PRODUCTION OF DEFINITIVE ENDODERM, filed Jun. 3, 2008, which is herein incorporated by reference in its entirety. After about 24 hours, the medium is exchanged for medium comprising RPMI with a small amount of animal serum, such as 0.2% fetal bovine serum (FBS); a TGFβ superfamily member growth factor, such as Activin A, Activin B, GDF-8 or GDF-11 (about 100 ng/mL); optionally, a rho-kinase or ROCK inhibitor, for another 24 (day 2) to 48 hours (day 3); and optionally 1:5000 of ITS. Importantly, production of definitive endoderm requires cell culture conditions without animal serum or with very small concentrations of animal serum, and no insulin or insulin like growth factor or very low concentrations of insulin or insulin-like growth factor, e.g., less than 0.2 μg/mL of insulin or insulin like growth factor. See McLean et al. (2007) Stem Cells 25: 29-38, which is herein incorporated by reference in its entirety. McLean et al. also showed that contacting hES cells with insulin at concentrations as low as 0.2 μg/mL at Stage 1 can be detrimental to the production of definitive endoderm. Still others skilled in the art have modified the Stage 1 differentiation of pluripotent stem cells to definitive endoderm substantially as described herein and in D'Amour et al. (2005). See e.g., Agarwal et al. (2008) 26:1117-1127; Amen et al. (2010) Stem Cells 28:45-56; Bingham et al. (2009) Stem Cells & Development 18(7): 1-10; Borowiak et al. (2009) Cell Stem Cell 4:348-358; Brolen et al. (2010) J. Biotechnology 145 (2010) 284-294; Brunner et al. (2009) Genome Res. 19:1044-56; Chen et al. (2008) Nature Chemical Biology 5(4): 258-265; Duan et al. (2010) Stem Cells, 28(4):674-86. Hinton et al. (2009) Stem Cells & Development, 19(6):797-807; Gibson et al. (2009) Integr. Biol. 1, 540-551; Johannesson et al. (2009) Plos ONE 4(3): e4794; King, C., "Culture and Preparation of Human Embryonic Stem Cells for Proteomics-Based Applications" Chapter 19 of Human Embryonic Stem Cell Protocols, Methods in Molecular Biology, Turksen (ed.) Humana Press; King et al. (2008) Regenerative Medicine, 3(2): 175-180; Maehr et al., (2009) Proc Nat'l Aca Sci 106(37): 15768-15773; Synnergren et al. (2009) Stems Cells & Development 19(7):961-78; and Zhou et al. (2008) Stem Cells & Development 17:737-750, all of which are incorporated herein by reference in their entirety. Proper differentiation, specification, characterization and identification of definitive endoderm are necessary in order to derive other endoderm-lineage cells. Definitive endoderm cells at this stage co-express SOX17 and HNF313 (FOXA2) and do not appreciably express at least HNF4alpha, HNF6, PDX1, SOX6, PROX1, PTF1A, CPA, cMYC, NKX6.1, NGN3, PAX3, ARX, NKX2.2, INS, GHRL, SST, or PP.

In preferred embodiments, the definitive endoderm cells are enriched, isolated and/or purified using one or more of the methods described in U.S. patent application Ser. No. 11/021, 618, entitled DEFINITIVE ENDODERM, filed Dec. 23, 2004, (now U.S. Pat. No. 7,510,876); U.S. Provisional Pat. Application No. 60/736,598, entitled MARKERS OF DEFINITIVE ENDODERM, filed Nov. 14, 2005; U.S. patent application Ser. No. 11/317,387 entitled EXPANSION OF DEFINITIVE ENDODERM CELLS, filed Dec. 22, 2005 (now U.S. Pat. No. 7,625,753); U.S. patent application Ser. No. 12/093,590, entitled MARKERS OF DEFINITIVE ENDODERM filed Jul. 21, 2008; and U.S. patent application Ser. No. 12/582,600, entitled EXPANSION OF DEFINITIVE ENDODERM CELLS, FILED Oct. 20, 2009, THE disclosures of which are incorporated herein by reference in their entirety.

Stage 2 takes the properly specified and characterized definitive endoderm cell culture from Stage 1 and produces foregut endoderm or specifically PDX1-negative foregut endoderm by incubating suspension cultures thereof with RPMI with optionally an increased amount of non-human animal serum, (e.g. 0.2 to 2% FBS); 1:1000 dilution of ITS; 25 ng/mL KGF (or FGF7); optionally, a ROCK or Rho Kinase inhibitor to enhance growth, survival, proliferation and promote cell-cell adhesion, for 24 hours (day 3 or day 4); and optionally, a TGFβ receptor kinase inhibitor such as SB-431542 or inhibitor IV. After about 24 hours, the medium is exchanged for medium with the same formulation but optionally without a TGFβ receptor kinase inhibitor and/or a ROCK inhibitor, for at least another 24 to 48 hours. A critical step for proper specification of foregut endoderm is removal of TGFβ family growth factors. Hence, a TGFβ receptor kinase inhibitor can optionally be added to Stage 2 cell cultures for about 24 hours after definitive endoderm induction or after Stage 1, such as TGFβ inhibitor no. IV, or SB431542, a specific inhibitor of activin receptor-like kinase (ALK), which is a TGFβ type I receptor. Foregut endoderm or PDX1-negative foregut endoderm cells produced during Stage 2 co-express SOX17, HNF1β and HNF4alpha and do not appreciably co-express at least PDX1, nor HNF6, PDX1, SOX6, PROX1, PTF1A, CPA, cMYC, NKX6.1, NGN3, PAX3, ARX, NKX2.2, INS, GSC, GHRL, SST, or PP, which are characteristic of definitive endoderm, PDX1-positive foregut endoderm, PDX1-positive pancreatic endoderm progenitor cells or endocrine precursors as well as singly or poly hormonal type cells.

Still in another embodiment, the FGF-family growth factor provided to the definitive endoderm cell culture or cell population is FGF10 and/or FGF7. However, it will be appreciated that other FGF-family growth factors or FGF-family growth factor analogs or mimetics may be provided instead of or in addition to FGF10 and/or FGF7. For example, an FGF-family growth factor selected from the group consisting of FGF1, FGF2, FGF3, etc., up to and including FGF23, may be provided.

In other embodiments, the hedgehog inhibitor is KAAD-cyclopamine. However, it will be appreciated that other hedgehog inhibitors can be used. Such inhibitors include, but are not limited to, KAAD-cyclopamine analogs, jervine, jervine analogs, hedgehog pathway blocking antibodies and any other inhibitors of hedgehog pathway function known to those of ordinary skill in the art. When used alone or in conjunction with FGF-family growth factor, the hedgehog inhibitor can be provided at a concentration of at least about 0.01 μM to about 50 μM.

Stage 3 takes the PDX-negative foregut endoderm cell culture properly specified from Stage 2 and produces PDX1-positive foregut endoderm cells by culturing in DMEM or RPMI with 1% vol/vol B27; 25 μM KAAD cyclopamine; a retinoid, such as about 0.2 μM retinoic acid (RA), or a retinoic acid analog such as about 3 nM of Arotinoid acid, 4-[(E)-2-(5,6,7,8-Tetrahydro-5,5,8,8-tetramethyl-2-naphthalenyl)-1-propenyl]benzoic acid or TTNPB; and about 50 ng/mL of Noggin, for about 24 to 72 hours. Again, a ROCK inhibitor such as Y-27632 can be used to enhance growth, survival, proliferation and promote cell-cell adhesion. PDX1-positive foregut cells produced during Stage 3 co-express PDX1 and HNF6 as well as SOX9 and PROX1, and do not appreciably co-express markers characteristic of definitive endoderm or PDX1-negative foregut endoderm cells as described above in Stages 1 and 2. Stages 2 and 3 are described in more detail in U.S. Application No. U.S. patent application Ser. No. 11/588, 693, entitled PDX1-EXPRESSING DORSAL AND VENTRAL FOREGUT ENDODERM, filed Oct. 27, 2006 which is incorporated herein by reference in its entirety.

Stage 4 takes cells which have been properly specified from Stage 3 and exchanges the culture medium for medium containing DMEM with about 1% vol/vol B27 supplement, about 50 ng/mL of KGF and 50 ng/mL EGF and about 50 ng/mL of noggin for about 24 to 96 hours (about 1-4 days) or more. Again, a ROCK inhibitor such as Y-27632 can be used to enhance growth, survival, proliferation and promote cell-cell adhesion. PDX1-positive pancreatic endoderm progenitor cells produced during Stage 4 co-express at least PDX1 and Nkx6.1 as well as PTF1A, and do not appreciably express certain other markers or all markers characteristic of definitive endoderm or PDX1-negative and PDX1-positive foregut endoderm cells as described above in Stages 1, 2 and 3, or endocrine or endocrine precursor cells.

In another embodiment of the invention, Stages 1-4 produce differentiated cell cultures consisting of a mixed population of cells, e.g., stage 4 differentiation produces PDX1-positive pancreatic endoderm progenitors having the potential to develop and mature in vivo into functioning insulin secreting cells, physiologically similar in function to that of natural human beta cells, but can also produce other cell populations. For example, stage 4 cell cultures also produce significant populations of endocrine precursor, or CHGA-positive cells. These different cell populations after stage 4 differentiation are described in more detail in U.S. application Ser. No. 12/132,437, entitled METHODS FOR PURIFYING ENDODERM AND PANCREATIC ENDODERM CELLS DERIVED FROM HES CELLS, field Jun. 3, 2008, which is herein incorporated by reference in its entirety.

With respect to some of the processes for the differentiation of pluripotent cells to definitive endoderm cells, the above-mentioned growth factors are provided to the cells so that the growth factors are present in the cultures at concentrations sufficient to promote differentiation of at least a portion of the pluripotent cells to definitive endoderm cells. In some processes, the above-mentioned growth factors are present in the cell culture at a concentration of at least 5 ng/mL, at least 10 ng/mL, at least 25 ng/mL, at least 50 ng/mL, at least 75 ng/mL, at least 100 ng/mL, at least 200 ng/mL, at least 300 ng/mL, at least 400 ng/mL, at least 500 ng/mL, at least 1000 ng/mL, at least 2000 ng/mL, at least 3000 ng/mL, at least 4000 ng/mL, at least 5000 ng/mL or more than 5000 ng/mL; or in the case with retinoic acid (RA), at least 0.05 µM, at least 0.1 µM, at least 1.5 µM, or at least 2 µM of RA is provided to stage 2 cultures (or PDX-1 negative foregut endoderm cell cultures) or equivalent effective concentrations if using RA analogs such as TTNPB. In certain processes for the differentiation of pluripotent cells to differentiated definitive endoderm and endoderm-lineage cells, the above-mentioned growth factors are removed from the cell culture subsequent to their addition. For example, the growth factors can be removed within about one day, about two days, about three days, about four days, about five days, about six days, about seven days, about eight days, about nine days or about ten days or more after their addition. In a typical process, the growth factors are removed about one, two or three days after their addition.

In other embodiments, the gamma secretase inhibitor (do we describe this above anywhere?) is provided at the start of the differentiation process, for example, at the pluripotent stage, and remains in the cell culture throughout the differentiation to pancreatic islet hormone-expressing cells. In still other embodiments, the gamma secretase inhibitor is added subsequent to the initiation of differentiation but prior to differentiation to the PDX1-positive foregut endoderm stage. In preferred embodiments, the gamma secretase inhibitor is provided to the cell culture or cell population at about the same time as providing the differentiation factors which promote the conversion of definitive endoderm to PDX1-positive endoderm. In other preferred embodiments, the gamma secretase inhibitor is provided to the cell culture or cell population after a substantial portion of the cells in the cell culture or cell population have differentiated to PDX1-positive foregut endoderm cells.

Encapsulation of PDX1-Positive Pancreatic Endoderm Progenitors

Cultures containing PDX1-positive pancreatic endoderm progenitor cells produced from Stage 4 are loaded and wholly contained in a macro-encapsulation device and transplanted in a patient, and the PDX1-positive pancreatic endoderm progenitor cells mature into physiologically functioning pancreatic hormone secreting cells in vivo, e.g., insulin secreting cells. Encapsulation of the PDX1-positive pancreatic endoderm progenitor cells and production of insulin in vivo is described in detail in U.S. patent application Ser. No. 12/618,659, entitled ENCAPSULATION OF PANCREATIC LINEAGE CELLS DERIVED FROM HUMAN PLURIPOTENT STEM CELLS, filed Nov. 13, 2009, which claims the benefit of priority to Provisional Pat. Application No. 61/114,857, entitled ENCAPSULATION OF PANCREATIC PROGENITORS DERIVED FROM HES CELLS, filed Nov. 14, 2008; and U.S. Provisional Pat. Application No. 61/121,084, entitled ENCAPSULATION OF PANCREATIC ENDODERM CELLS, filed Dec. 9, 2008. The disclosures of each of these applications are incorporated herein by reference in their entirety.

The methods, compositions and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that various substitutions and modifications may be made to the invention disclosed herein without departing from the scope and spirit of the invention.

For example, Activin A, a member of the TGFβ superfamily of growth factors or signaling proteins, is used to produce definitive endoderm from pluripotent stem cells, e.g., hES cells and iPS cells, however, other TGFβ super family members can be used, for example GDF-8 and GDF-11, to produce definitive endoderm as described in PCT International Pat. Pub. No. WO 2009/154606, entitled GROWTH FACTORS FOR PRODUCTION OF DEFINITIVE ENDODERM, filed Jun. 3, 2008, which is herein incorporated by reference in its entirety.

Retinoic acid (RA) is used to differentiate PDX1-negative foregut endoderm cells in Stage 2 to PDX1-positive foregut cells in Stage 3. However, other retinoids or retinoic acid analogues such as 4-[(E)-2-(5,6,7,8-tetrahydro-5,5,8,8-tetramethyl-2-napthalenyl)-1-propenyl]benzoic acid (TTNPB) and similar analogs (e.g., 4-HBTTNPB) can be used.

Noggin, for example, is a protein that inactivates members of the TGFβ superfamily of signaling proteins, such as bone morphogenetic protein-4 (BMP4). However, other BMP4 inhibitors such as Chordin and Twisted Gastrulation (Tsg) or anti-BMP neutralizing antibodies can prevent BMP binding to its cell surface receptors, thereby effectively inhibiting BMP signaling. Still small molecules such as dorsomorphin (6-[4-(2-Piperidin-1-yl-ethoxy)phenyl]-3-pyridin-4-yl-pyrazolo[1,5-a]pyrimidine), also known as compound C, and its derivatives can also be used to inactivate or inhibit BMP for example. Alternatively, substitutions for Noggin may come from the gene for human Noggin, which has been cloned and sequenced. See U.S. Pat. No. 6,075,007, which is herein incorporated by reference. Analysis of the Noggin sequence shows a carboxy terminal region having homology to a Kunitz-type protease inhibitor, indicating that other Kunitz-type protease inhibitors may potentially have a similar effect of inhibiting BMP. The macro-encapsulation devices described herein and in U.S. patent application Ser. No. 12/618,659 (incorporated herein by reference in its entirety), are again only exemplary and are not intended as limitations on the scope of the invention. Particularly, changes to the device design such as size of the device, plurality of chambers or subcompartments in the device, plurality of ports, or even

Monitoring the Production of Multipotent or Differentiated Cells

A cell differentiating medium or environment may be utilized to partially, terminally, or reversibly differentiate the differentiable cells of the present invention. In accordance with the invention the cell differentiating medium or environment may contain a variety of components including, for example, KODMEM medium (Knockout Dulbecco's Modified Eagle's Medium), DMEM, Ham's F12 medium, FBS (fetal bovine serum), FGF2 (fibroblast growth factor 2), KSR or hLIF (human leukemia inhibitory factor). The cell differentiating medium or environment can also contain supplements such as L-Glutamine, NEAA (non-essential amino acids), P/S (penicillin/streptomycin), N2, B27 and β-mercaptoethanol (β-ME). It is contemplated that additional factors may be added to the cell differentiating medium or environment, including, but not limited to, fibronectin, laminin, heparin, heparin sulfate, retinoic acid, members of the epidermal growth factor family (EGFs), members of the fibroblast growth factor family (FGFs) including FGF2, FGF7, FGF8, and/or FGF10, members of the platelet derived growth factor family (PDGFs), transforming growth factor (TGF)/bone morphogenetic protein (BMP)/growth and differentiation factor (GDF) factor family antagonists including but not limited to noggin, follistatin, chordin, gremLin, cerberus/DAN family proteins, ventropin, high dose Activin, and amnionless or variants or functional fragments thereof. TGF/BMP/GDF antagonists can also be added in the form of TGF/BMP/GDF receptor-Fc chimeras. Other factors that may be added include molecules that can activate or inactivate signaling through Notch receptor family, including but not limited to proteins of the Delta-like and Jagged families as well as inhibitors of Notch processing or cleavage, or variants or functional fragments thereof. Other growth factors may include members of the insulin like growth factor family (IGF), insulin, the wingless related (WNT) factor family, and the hedgehog factor family or variants or functional fragments thereof. Additional factors may be added to promote mesendoderm stem/progenitor, endoderm stem/progenitor, mesoderm stem/progenitor, or definitive endoderm stem/progenitor proliferation and survival, as well as survival and differentiation of derivatives of these progenitors.

The compositions described herein are useful for the screening of test compounds to determine whether a test compound modulates pluripotency, proliferation, and/or differentiation of differentiable cells. Pluripotency, proliferation and/or differentiation of differentiable cells can be readily ascertained by one of ordinary skill in the art. Non-limiting methods include examining cell morphology, the expression of various markers, teratoma formation, cell counts and measurements of impedance.

The progression of pluripotent cells to multipotent cells to further multipotent cells or differentiated cells can be monitored by measuring and quantifying the level expression of certain gene markers, such as detecting the presence or absence of a specific gene marker at different time points before and after addition of an exogenous agent, for example, a TGF-β signaling agent. Alternatively, the expression of certain markers can be determined by measuring the level at which the marker is present in the cells of the cell culture or cell population. For example, in certain processes, the expression of markers characteristic of pluripotent cells as well as the lack of significant expression of markers characteristic of multipotent or differentiated cells is determined.

Within another embodiment, the monitoring the production of other less differentiated cell types of the definitive endoderm lineage, qualitative or semi-quantitative techniques, such as blot transfer methods and immunocytochemistry (ICC) or immunohistochemistry (IHC), can be used to measure marker expression. Alternatively, marker expression can be accurately quantified with techniques such as Q-PCR. Additionally, it will be appreciated that at the polypeptide level, many of the markers of pancreatic islet hormone-expressing cells are secreted proteins. As such, techniques for measuring extracellular marker content, such as ELISA, may be utilized. This and other monitoring and screening methodologies are described in detail in U.S. application Ser. No. 11/165,305, entitled METHODS FOR IDENTIFYING FACTORS FOR DEFINITIVE ENDODERM, filed Jun. 23, 2005, now U.S. Pat. No. 7,541,185, which is herein incorporated by reference in its entirety.

The developmental progression of the pluripotent cells described herein (e.g., cells produced as a result of Stages or Steps 1-4 or steps 1-5 as described in D'Amour et al. 2006, supra) can be monitored by determining the expression of markers characteristic of each pluripotent-derived cell type along the developmental pathway. For example, in some processes, the identification and characterization of a pluripotent-derived cell type is by expression of a certain marker or by different expression levels and patterns of more than one marker. That is, the presence or absence, the high or low expression, of one or more the marker(s) typifies and identifies a cell-type. Also, certain markers can have transient expression, whereby the marker is highly expressed during one stage of development and poorly expressed in another stage of development. The expression of certain markers can be determined by measuring the level at which the marker is present in the cells of the cell culture or cell population as compared to a standardized or normalized control marker. In such processes, the measurement of marker expression can be qualitative or quantitative. One method of quantitating the expression of markers that are produced by marker genes is through the use of quantitative PCR (Q-PCR). Methods of performing Q-PCR are well known in the art.

In still other embodiments, Q-PCR can be used in conjunction with immunohistochemical techniques or flow cytometry techniques to effectively and accurately characterize and identify cell types and determine both the amount and relative proportions of such markers in a subject cell type. In one embodiment, Q-PCR can quantify levels of RNA expression in a cell culture containing a mixed population of cells. However, Q-PCR cannot provide or qualify whether the subject markers or proteins are co-expressed in the same cell. In another embodiment, Q-PCR is used in conjunction with flow cytometry methods to characterize and identify cell types. Thus, by using a combination of the methods described herein, and such as those described above, complete characterization and identification of various cell types, including endoderm lineage type cells, can be accomplished and demonstrated.

It has been demonstrated that the measurement of the expression of a particular gene by Q-PCR can be used to accurately estimate the relative amount of cells in mixed cell populations which differentially express that particular gene. Hence, using Q-PCR based measurement of gene expression, the amount of pluripotent, differentiated multipotent, differentiated unipotent, and/or terminally differentiated cells can be determined in certain mixed cell populations under various cell culture conditions. For example, populations of pluripotent cells and differentiated cells such as Stage 1 (definitive endoderm) cells were mixed together in known proportions and assayed for gene expression of definitive endoderm markers. Total RNA was isolated from 10,000 total cells and performed in triplicate for each condition (sample). One-third (⅓) of the isolated RNA was then used for the synthesis of cDNA and one-fortieth (1/40$^{th}$) of the cDNA reaction was used in each Q-PCR amplification. Therefore, each PCR data point is derived approximately from 1/120$^{th}$ of the original 10,000 cell input (or RNA equivalent of about 83 total cells. Q-PCR was performed using methodologies well established in the art. See D'Amour et al. (2006), supra.

FIG. 1A provides a graphical representation of Q-PCR gene expression data obtained for the SOX17 marker, which is expressed in the Stage 1 cells (definitive endoderm, DE), but not in pluripotent cells, for example, hESCs. The first column of FIG. 1A (far left) shows the signal produced by Q-PCR from 100% hESCs, whereas the far right column shows the signal produced by PCR from 100% DE cells. The columns in between the 100% hESCs and the 100% DE cells show the signal produced by Q-PCR from known dilution mixtures (or ratios) of hESCs:DE cells. For example, column 2 shows the signal produced by Q-PCR from a mixture of 99:1 hESCs:DE cells, column 3 shows the signal produced by Q-PCR from a mixture of 95:5 hESCs:DE cells, column 4 shows the signal produced by Q-PCR from a mixture of 90:10 hESCs:DE cells, and so on through the penultimate column, which shows the signal produced by Q-PCR from a mixture of 1:99 hESCs:DE cells.

The data presented in FIG. 1A demonstrate that as the number of human definitive endoderm cells in the mixed population increases, so does the level of gene expression for the definitive endoderm-specific genes. Moreover, this Q-PCR assay is highly sensitive, detecting the expression of definitive endoderm marker genes when definitive endoderm makes up only 1% of the cell population, e.g., column 2 of panel A has a hESC:DE ratio of 99:1. This indicates that this Q-PCR method can detect even a single definitive endoderm cell equivalent in a mixed cell culture. Additionally, the Q-PRC signal response is reasonably linear over most of the range of cell concentrations (from 1% to 90% definitive endoderm).

The relationship between the amounts of human definitive endoderm cells to the expression of a definitive endoderm marker was also observed when the sample size was 50,000 cells/sample. Further, other gene markers present in definitive endoderm cells were analyzed and results were consistent with that observed for SOX17.

Figure 1B:
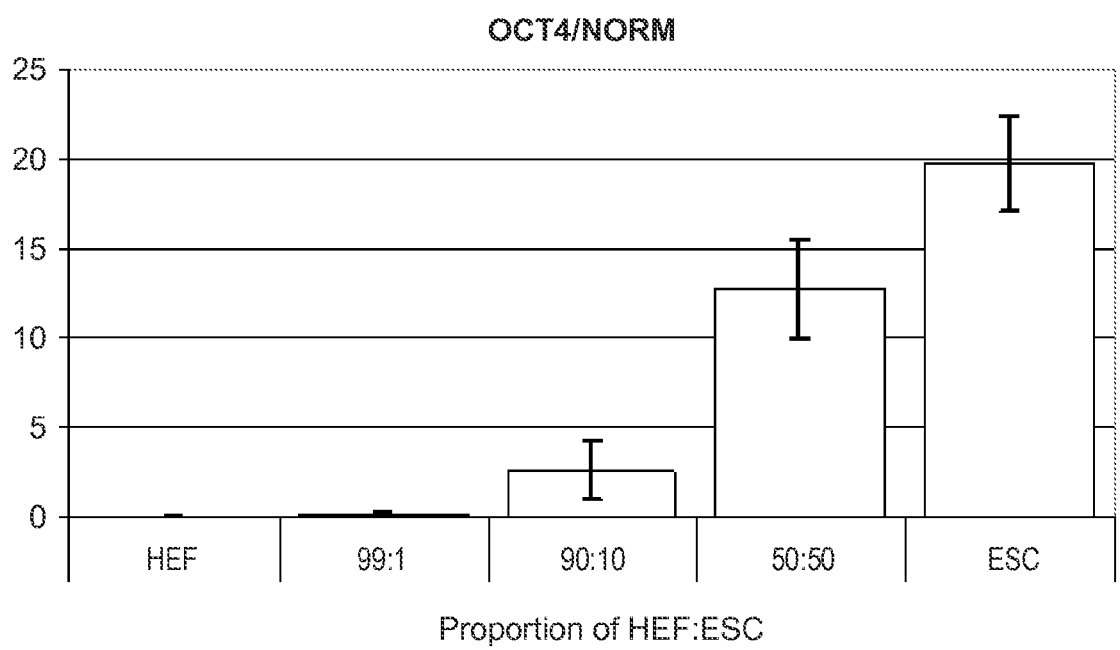
FIG. 1B shows OCT4 gene expression in hESCs mixed with human embryonic fibroblast cells (HEFs) in known ratios (100:0 HEFs:hESCs; 99:1 HEFs:hESCs; 90:10 HEFs: hESCs; 50:50 HEFs:hESCs; and 0:100 HEFs:hESCs.

In another embodiment, the relative amounts of pluripotent cells present in mixed cell populations can be measured by determining the relative gene expression value for the pluripotent stem cell marker genes. For example, undifferentiated hESCs were mixed with human embryonic fibroblast cells (HEFs) in known proportions, i.e., 100:0 HEFs:hESCs; 99:1 HEFs:hESCs; 90:10 HEFs:hESCs; 50:50 HEFs:hESCs; and 0:100 HEFs:hESCs. Each sample containing the described mixtures of unclustered cells was placed into rotational culture to form a suspension aggregate culture essentially as described herein. Q-PCR samples were taken at 48 hours of culture and assayed for the expression of pluripotent marker genes including those listed in Table 1, such as OCT4. Similar to the results described above in FIG. 1A, the relative expression of the pluripotent cell marker gene, OCT4, is proportional to the percentage (ratio) of the pluripotent cells that were placed into the culture. See FIG. 1B. Therefore, the described method of determining relative cell abundance by determining levels of gene marker expression for a specific cell type does not depend on any particular cell type; rather the method is equally reproducible for pluripotent cells (e.g., hESCs) and for pluripotent-derived cells, such as Stages 1 (definitive endoderm or SOX17 & HNF3β definitive endoderm), 2 (foregut, or PDX1-negative foregut endoderm, or SOX17, HNF3β and HNF4α foregut endoderm), 3 (posterior foregut endoderm, or PDX1-positive foregut endoderm), 4 (pancreatic progenitors, or pancreatic endoderm or epithelium, or PDX1/NKX6.1 co-positive pancreatic endoderm) and 5 (endocrine or endocrine precursor cells, or NGN3/NKX2.2 co-positive endocrine precursor cells, or insulin positive endocrine cells) cells. Still other pluripotent cell markers gene such as those described in Table 1, in particular SOX2, can be analyzed similarly.

TABLE 1

Pluripotency Cell Markers

| Marker Name | Mouse EC/ES/EG Cells | Monkey ES Cells | Human Pluripotent ES/iPS Cells | Human EG Cells |
|---|---|---|---|---|
| SSEA-1 | + | − | − | − |
| SSEA-3 | − | + | + | + |
| SSEA-4 | − | + | + | + |
| TRA-1-60 | − | + | + | + |
| TRA-1-81 | − | + | + | + |
| Alkaline Phosphatase | + | + | + | + |
| Oct4 (POU5F1) | + | + | + | Unknown |
| Nanog | + | + | + | + |
| SOX2 | + | + | + | + |
| Teratoma formation in vivo | + | + | + | − |

KEY
ES Cell = Embryonic stem cell
EG Cell = Embryonic germ cell
EC Cell = Embryonal carcinoma cell
TRA = Tumor rejection antigen 1
SSEA = Stage-specific embryonic antigen
SOX2 = SRY (sex determining region Y) box 2

Figure 1C:
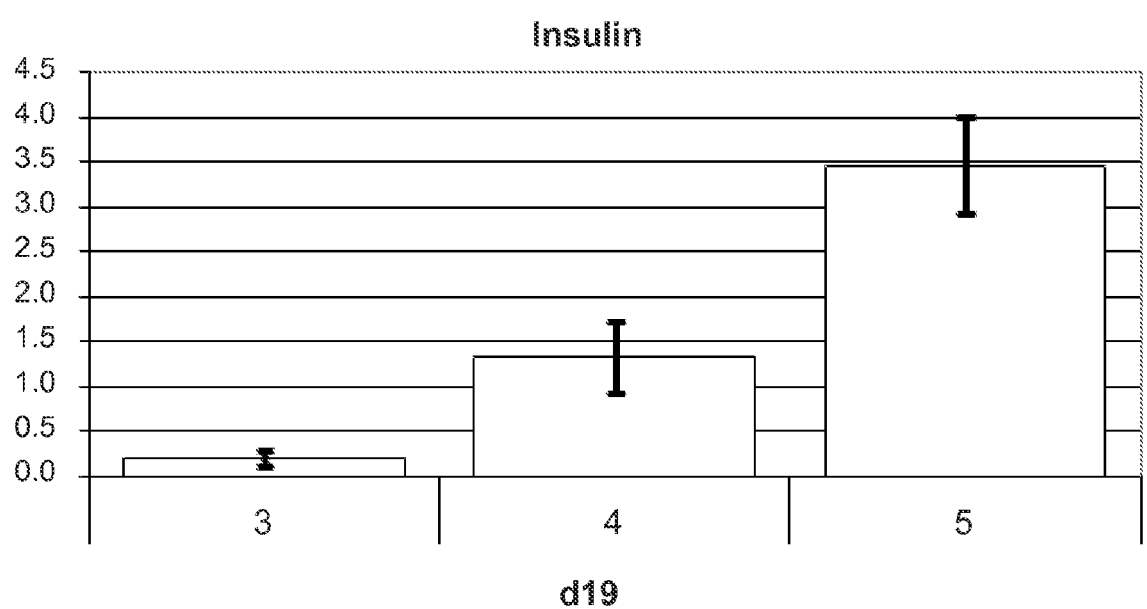
FIG. 1C shows that relative insulin (INS) gene expression is proportionate to the numbers of cells that express the marker gene in the population.

Q-PCR results can be confirmed using flow cytometry. Human ESCs were differentiated to Stage 5 (pancreatic endocrine cells). See D'Amour et al. (2006), supra. The proportion of the cell population that had differentiated to pancreatic endocrine cells was determined by flow cytometry using an antibody against insulin. Populations of approximately 1%, 10% or 20% insulin-expressing endocrine cells were obtained. Messenger RNA samples were then taken from these three populations and Q-PCR was performed. The results shown in FIG. 1C demonstrated that the relative insulin gene expression is indeed proportional to the numbers of cells which express the marker gene in the population. This method was highly reproducible, and further demonstrates the correlation between the amount of marker gene expression and the percentage of cells in a cell population expressing the marker gene. Additionally, other pancreatic endocrine cell gene markers were analyzed and results were consistent with those observed for insulin.

Still other methods, which are known in the art, can also be used to quantitate marker gene expression. For example, the expression of a marker gene product can be detected by using antibodies specific for the marker gene product of interest (e.g., by Western blot, flow cytometry analysis, ELISA, immunohistochemistry or immunofluorescence, and the like). In certain processes, the expression of marker genes characteristic of pluripotent-derived cells as well as the lack of significant expression of marker genes characteristic of pluripotent-derived cells can be determined. Still further methods for characterizing and identifying pluripotent-derived cells types are described in related applications as indicated above, which are herein incorporated by reference in their entirety.

Amplification probe/primer combinations suitable for use in amplification assays include the following: Insulin (INS) (GenBank NM_000207): primers AAGAGGCCATCAAG-CAGATCA (SEQ ID NO: 1); CAGGAGGCGCATCCACA (SEQ ID NO: 2); NRx6.1 (NM_006168): primers CTGGC-CTGTACCCCTCATCA (SEQ ID NO: 3); CTTC-CCGTCTTTGTCCAACAA (SEQ ID NO: 4); Pdx1 (NM_000209): primers AAGTCTACCAAAGCTCACGCG (SEQ ID NO: 5); GTAGGCGCCGCCTGC (SEQ ID NO: 6); Ngn3 (NM_020999): primers GCTCATCGCTCTCTAT-TCTTTTGC (SEQ ID NO: 7); GGTTGAGGCGTCATC-CTTTCT (SEQ ID NO: 8); FOXA2 (HNF3B) (NM_021784): primers GGGAGCGGTGAAGATGGA (SEQ ID NO: 9); TCATGTTGCTCACGGAGGAGTA (SEQ ID NO: 10); Glucagon (GCG) (NM_002054): primers AAG-CATTTACTTTGTGGCTGGATT (SEQ ID NO: 11); TGATCTGGATTTCTCCTCTGTGTCT (SEQ ID NO: 12); HNF6 (NM_030712): primers CGCTCCGCTTAGCAGCAT (SEQ ID NO: 13); GTGTTGCCTCTATCCTTCCCAT (SEQ ID NO: 14); HNF4Alpha (NM_000457): primers GAA-GAAGGAAGCCGTCCAGA (SEQ ID NO: 15); GACCT-TCGAGTGCTGATCCG (SEQ ID NO: 16); Sox17 (NM_022454): primers GGCGCAGCAGAATCCAGA (SEQ ID NO: 17); CCACGACTTGCCCAGCAT (SEQ ID NO: 18); HLxB9 (NM_005515): primers CAC-CGCGGGCATGATC (SEQ ID NO: 19); ACTTCCCCAG-GAGGTTCGA (SEQ ID NO: 20); Nkx2.2 (NM_002509): primers GGCCTTCAGTACTCCCTGCA (SEQ ID NO: 21); GGGACTTGGAGCTTGAGTCCT (SEQ ID NO: 22); PTF1a (NM_178161): primers GAAGGTCATCATCTGC-CATCG (SEQ ID NO: 23) GGCCATAATCAGGGTCGCT (SEQ ID NO: 24); SST (NM_001048): primers CCCCA-GACTCCGTCAGTTTC (SEQ ID NO: 25); TCCGTCTG-GTTGGGTTCAG (SEQ ID NO: 26); PAX6 (NM_000280): primers CCAGAAAGGATGCCTCATAAAGG (SEQ ID NO: 27); TCTGCGCGCCCCTAGTTA (SEQ ID NO: 28); Oct4 primers: TGGGCTCGAGAAGGATGTG (SEQ ID NO: 29) GCATAGTCGCTGCTTGATCG (SEQ ID NO: 30); MIXL1 primers CCGAGTCCAGGATCCAGGTA (SEQ ID NO: 31) CTCTGACGCCGAGACTTGG (SEQ ID NO: 32); GATA4 primers CCTCTTGCAATGCGGAAAG (SEQ ID NO: 33) CGGGAGGAAGGCTCTCACT (SEQ ID NO: 34); GSC primers GAGGAGAAAGTGGAGGTCTGGTT (SEQ ID NO: 35) CTCTGATGAGGACCGCTTCTG (SEQ ID NO: 36); CER primers ACAGTGCCCTTCAGCCAGACT (SEQ ID NO: 37) ACAACTACTTTTTCACAGCCTTCGT (SEQ ID NO: 38); AFP primers GAGAAACCCACTGGAGAT-GAACA (SEQ ID NO: 39) CTCATGGCAAAGTTCTTC-CAGAA (SEQ ID NO: 40); SOX1 primers ATGCACCGC-TACGACATGG (SEQ ID NO: 41) CTCATGTAGCCCTGCGAGTTG (SEQ ID NO: 42); ZIC1 primers CTGGCTGTGGCAAGGTCTTC (SEQ ID NO: 43) CAGCCCTCAAACTCGCACTT (SEQ ID NO: 44); NFM primers ATCGAGGAGCGCCACAAC (SEQ ID NO: 45) TGCTGGATGGTGTCCTGGT (SEQ ID NO: 46). Other primers are available through ABI Taqman including FGF17 (Hs00182599_m1), VWF (Hs00169795_m1), CMKOR1 (Hs00604567_m1), CRIP1 (Hs00832816_g1), FOXQ1 (Hs00536425_s1), CALCR (Hs00156229_m1) and CHGA (Hs00154441_m1).

Monitoring Pluripotent Cells

Figure 2:
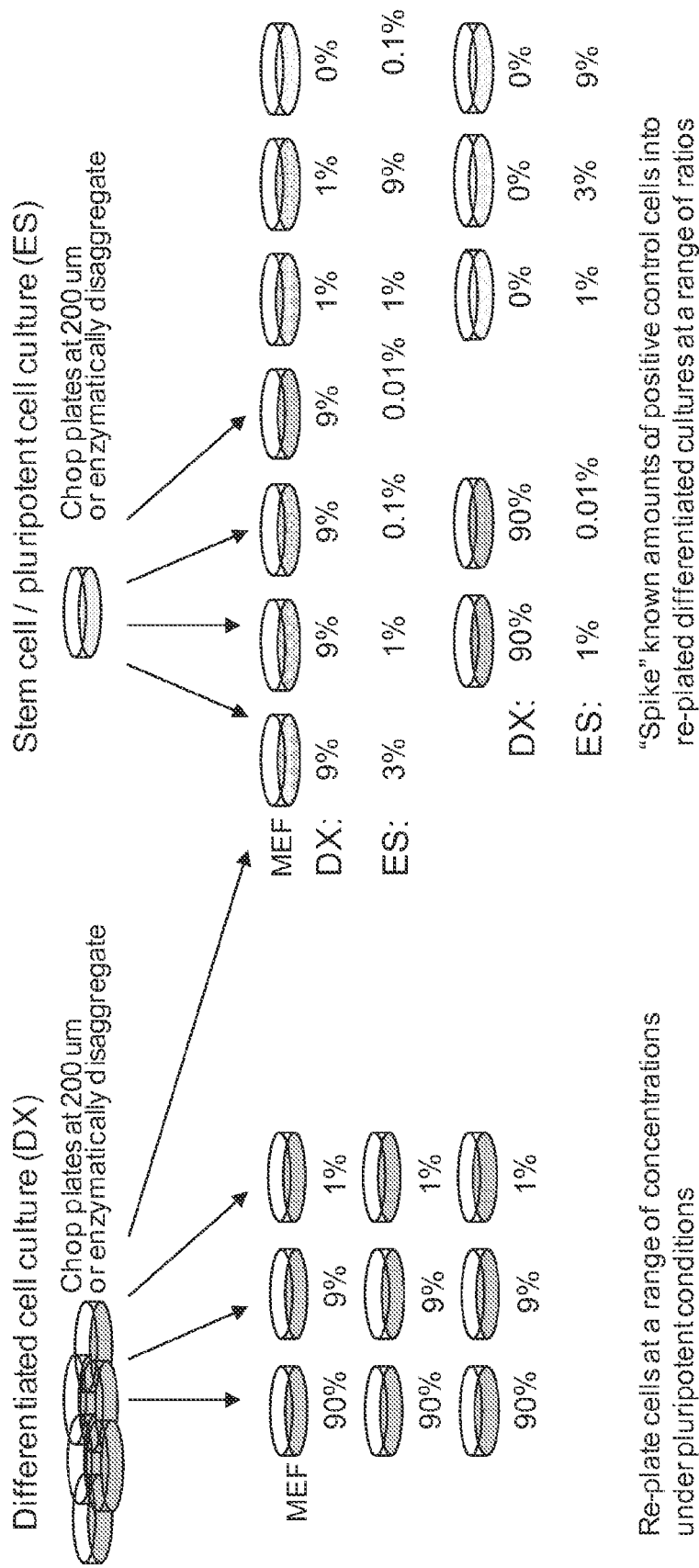
FIG. 2 is an exemplary schematic for monitoring and detecting levels of pluripotent stem cells in differentiated cultures.

In addition to the methods for monitoring and determining estimates of the relative amount of pluripotent or pluripotent-derived cells in mixed cell populations expressing a particular gene described above, another method for monitoring and determining levels of at least pluripotent cells is to re-plate differentiated cell cultures as described in FIG. 2 under pluripotent cell culture conditions. This can be performed with adherent cell cultures or suspension aggregate cultures as described in U.S. patent application Ser. No. 12/264,760, entitled STEM CELL AGGREGATE SUSPENSION COMPOSITIONS AND METHODS OF DIFFERENTIATION THEREOF, filed Nov. 4, 2008, which is herein incorporated by reference in its entirety. Pluripotent cell culture conditions are those conditions that promote pluripotent growth and proliferation, including growth on feeder layers or under feeder-free conditions on an extracellular matrix derived from lysed fibroblasts feeders, or on synthetic surface matrices (Corning), or in feeder-free pluripotent cell culture media as described in related U.S. patent application Ser. No. 11/875,057, entitled METHODS AND COMPOSITIONS FOR FEEDER-FREE PLURIPOTENT STEM CELL MEDIA CONTAINING HUMAN SERUM, filed Oct. 20, 2008, which is herein incorporated by reference in its entirety. This approach amplifies small numbers of pluripotent cells in any culture because when transferred or re-plated and cultured under pluripotent cell culture conditions, even the small numbers of pluripotent cell(s) will proliferate faster and acquire doubling times similar to that for other pluripotent cells in pluripotent culture conditions (e.g., hESCs double overnight or in about 18-24 hours). Positive staining with Ki67 has confirmed that cells from re-plated cultures were proliferating.

Screening Methods Employing Pluripotent Suspension Aggregation Cultures

In some embodiments, screening methods are employed to obtain certain cell populations comprising pluripotent, multipotent and/or differentiated cells. The cell population is then provided with a candidate differentiation factor. At a first time point, which is prior to or at approximately the same time as providing the candidate differentiation factor, expression of a marker is determined. Alternatively, expression of the marker can be determined after providing the candidate differentiation factor. At a second time point, which is subsequent to the first time point and subsequent to the step of providing the candidate differentiation factor to the cell population, expression of the same marker is again determined Whether the candidate differentiation factor is capable of promoting the differentiation of the pancreatic precursor cells is determined by comparing expression of the marker at the first time point with the expression of the marker at the second time point. If expression of the marker at the second time point is increased or decreased as compared to expression of the marker at the first time point, then the candidate differentiation factor is capable of promoting the differentiation of pancreatic progenitor cells.

In embodiments of the screening methods described herein, the cell population is contacted or otherwise provided with a candidate (test) differentiation factor or cytotoxic or inhibitory factor. The candidate differentiation factor or cytotoxic or inhibitory factor can comprise any molecule that may have the potential to promote the differentiation of any of the above-mentioned cells or prevent growth or reduce the proliferation of pluripotent stem cells or kill them pluripotent stem cells. In alternate embodiments, the candidate differentiation factor or cytotoxic or inhibitory factor comprises a molecule that is not known to promote cell differentiation. In preferred embodiments, the candidate differentiation factor or cytotoxic or inhibitory factor comprises a molecule that is not known to promote the differentiation of human pancreatic progenitor cells.

In some embodiments of the screening methods described herein, the candidate differentiation factor or cytotoxic or inhibitory factor comprises a small molecule. "Small molecule" is used herein as it is in the art to refer to low molecular weight organic compounds, which are by definition not polymers. Small molecules can be naturally occurring (such as endogenous neurotransmitters) or can prepared by synthetic organic chemistry methods known in the art. In certain embodiments, a small molecule is a molecule having a molecular mass of about 800 Daltons or less.

In other embodiments described herein, the candidate differentiation factor or cytotoxic or inhibitory agent comprises a large molecule, e.g., a polypeptide. The polypeptide can be any polypeptide including, but not limited to, a glycoprotein, a lipoprotein, an extracellular matrix protein, a cytokine, a chemokine, a peptide hormone, an interleukin or a growth factor. Preferred polypeptides include growth factors.

In some embodiments of the screening methods described herein, the candidate differentiation factor or candidate cytotoxic or inhibitory agent is provided to the cell population in one or more concentrations. In some embodiments, the candidate differentiation factor or candidate cytotoxic or inhibitory agent is provided to the cell population so that the concentration of the candidate differentiation factor in the medium surrounding the cells ranges from about 0.1 ng/mL to about 10 mg/mL. In some embodiments, the concentration of the candidate differentiation factor or candidate cytotoxic or inhibitory agent in the medium surrounding the cells ranges from about 1 ng/mL to about 1 mg/mL. In other embodiments, the concentration of the candidate differentiation factor or candidate cytotoxic or inhibitory agent in the medium surrounding the cells ranges from about 10 ng/mL to about 100 μg/mL. In still other embodiments, the concentration of the candidate differentiation factor or candidate cytotoxic or inhibitory agent in the medium surrounding the cells ranges from about 100 ng/mL to about 10 μg/mL. In preferred embodiments, the concentration of the candidate differentiation factor or candidate cytotoxic or inhibitory agent in the medium surrounding the cells is about 5 ng/mL to 1000 μg/mL.

In some embodiments, steps of the screening methods described herein comprise determining expression of at least one marker at a first time point and a second time point. In some of these embodiments, the first time point can be prior to or at approximately the same time as providing the cell population with the candidate differentiation factor or candidate cytotoxic or inhibitory agent. Alternatively, in some embodiments, the first time point is subsequent to providing the cell population with the candidate differentiation factor or candidate cytotoxic or inhibitory agent. In some embodiments, expression of a plurality of markers is determined at a first time point.

The aforementioned methods are equally applicable to screening for small molecule and other compounds that are cytotoxic or inhibit pluripotent stem cell growth, expansion and/or proliferation; or in the case of a candidate differentiation factor, improve viability, stabilize differentiation state, increase growth and maintain pluripotency of hES cells. It will be well within the level of skill in the art to adapt the teachings described herein to such screening methods.

In addition to determining expression of at least one marker at a first time point, some embodiments of the screening methods described herein contemplate determining expression of at least one marker at a second time point, which is subsequent to the first time point and which is subsequent to providing the cell population with the candidate differentiation factor or candidate cytotoxic or inhibitory agent. In such embodiments, expression of the same marker is determined at both the first and second time points. In some embodiments, expression of a plurality of markers is determined at both the first and second time points. In such embodiments, expression of the same plurality of markers is determined at both the first and second time points. In some embodiments, marker expression is determined at a plurality of time points, each of which is subsequent to the first time point, and each of which is subsequent to providing the cell population with the candidate differentiation factor or candidate cytotoxic or inhibitory agent. In certain embodiments, marker expression is determined by Q-PCR. In other embodiments, marker expression is determined by immunocytochemistry.

In some embodiments of the screening methods described herein, sufficient time is allowed to pass between providing the cell population with the candidate differentiation factor or candidate cytotoxic or inhibitory agent and determining marker expression at the second time point. Sufficient time between providing the cell population with the candidate differentiation factor or candidate cytotoxic or inhibitory agent and determining expression of the marker at the second time point can be as little as from about 1 hour to as much as about 10 days. In some embodiments, the expression of at least one marker is determined multiple times subsequent to providing the cell population with the candidate differentiation factor or candidate cytotoxic or inhibitory agent. In some embodiments, sufficient time is at least about 1 hour, at least about 6 hours, at least about 12 hours to several days to weeks.

In some embodiments of the methods described herein, it is further determined whether the expression of the marker at the second time point has increased or decreased as compared to the expression of this marker at the first time point. An increase or decrease in the expression of the at least one marker indicates that the candidate differentiation factor or candidate cytotoxic or inhibitory agent is capable of promoting the differentiation of the cell or blocking or inhibiting the cell. Similarly, if expression of a plurality of markers is determined, it is further determined whether the expression of the plurality of markers at the second time point has increased or decreased as compared to the expression of this plurality of markers at the first time point. An increase or decrease in marker expression can be determined by measuring or otherwise evaluating the amount, level or activity of the marker in the cell population at the first and second time points. Such determination can be relative to other markers, for example housekeeping gene expression, or absolute. In certain embodiments, wherein marker expression is increased at the second time point as compared with the first time point, the amount of increase is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of increase is less than 2-fold. In embodiments where marker expression is decreased at the second time point as compared with the first time point, the amount of decrease is at least about 2-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold or more than at least about 100-fold. In some embodiments, the amount of decrease is less than 2-fold.

Throughout this application, various publications are referenced. The disclosures of all of these publications and those references cited within those publications in their entireties are herein incorporated by reference into this application in their entirety in order to more fully describe the state of the art to which this invention pertains.

EXAMPLES

The simple defined media (DC) employed in the following Examples is termed DC-HAIF, and consists essentially of DMEM/F12; 2 mM Glutamax; 1× non-essential amino acids; 0.5 U/mL penicillin; 0.5 U/mL streptomycin; 10 μg/mL transferrin (all from Invitrogen, Carlsbad, Calif., USA); 0.1 mM β-mercaptoethanol (Sigma); 0.2% fatty acid-free Cohn's fraction V BSA (Serologicals); 1× Trace Element mixes A, B and C (Cellgro); 50 μg/mL Ascorbic Acid (Sigma); 10 ng/mL HRG-13 (H); 10 ng/mL Activin A (A); 200 ng/mL LR-IGF1 (I) and 8 ng/mL FGF2 (F). DC-HAIF supported long term maintenance of pluripotent hES cells, as well as single cell passaging and scaled expansion of hES cell using Accutase™. See Wang, L. et al. (2007) Blood, 110(12): 4111-4119. A batch-tested commercial formulation of DC-HAIF is available from Invitrogen, under the trade name StemPro® hESC SFM.

Throughout background studies it became clear that FGF2 was not a required component of the defined medium. Only poor or moderate phosphorylation of FGF receptors was observed after growth factor stimulation, even at high concentrations, and FGF2 could be omitted from the defined medium without any measurable impact on the culture, in terms of proliferation, spontaneous differentiation or maintenance of pluripotency. See Wang, L. et al. 2007, supra. Therefore, certain studies below were conducted in the absence of added FGF2, and as indicated in the text and figure legends. Furthermore, because some assays required varying combinations of growth factors, a growth factor-free batch of StemPro® hESC SFM was custom ordered & purchased from Life Technologies to provide such flexibility.

In order to highlight additional signaling pathways with critical functions in hES cell culture, a LOPAC library consisting essentially of a library of small molecule compounds with known bioactivities was employed to screen against hES cell cultures. The aim was to identify those small molecules that negatively impacted culture expansion and/or pluripotency Inhibition of key pathways would be expected to result in slowed proliferation, cytotoxicity, apoptosis or differentiation. Importantly, these primary and secondary screens were performed on the background of the simple defined medium described above and herein, reducing variability typically introduced by undefined components such as serum or semifractionated albumin. To determine activity of compounds, an alkaline phosphatase staining assay was performed. Alkaline phosphatase is a stem cell marker associated with undifferentiated pluripotent stem cells. Using this assay, about 50 small molecule compounds demonstrated some measurable amount of activity with regard to their ability to negatively impact hES cells, including reduced hES cell growth and survival. Of these compounds, numerous inhibitors of cell surface neurotransmitter receptors were identified, suggesting at least a signaling role for these receptors in self-renewal. Using naturally occurring ligands or pharmacologically related derivatives, several classes of small molecule neurotransmitters, which may also act as hormones, were identified and demonstrated support and/or expansion of hES cell growth and survival at low density. Such activities could be crucial for developing advanced technologies for commercial and clinical application of hES cells, such as reliable single cell cloning, efficient derivation of new hES cell lines in fully defined and GMP-compliant conditions, growth of hES cells in suspension and enhanced viability upon passaging. The goal of the following studies was to similarly identify agents having the opposite effect on pluripotent stem cells. More specifically, the screening methods of the invention were used to identify pluripotent stem cell inhibitory and cytotoxic agents that can be used to reduce populations of undifferentiated cells during directed differentiation in vitro.

It should be understood that the foregoing relates to exemplary embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents expressions, which, after reading the description herein, may suggest themselves to those skilled in the art without departing from the spirit of the present invention and/or the scope of the appended claims.

The methods, compositions, and devices described herein are presently representative of preferred embodiments and are exemplary and are not intended as limitations on the scope of the invention. For example, certain hES cell lines were employed, however the present invention contemplates use with any pluripotent stem cell lines including, human iPS cell lines and other not mentioned hES and iPS cell lines such as that in Tables 1 and 2 below, respectively, which were adapted from the National Institute of Health's Stem Cell Registry on the world wide web at stemcells.nih.gov/research/registry, as well as the Human Embryonic Stem Cell Registry and the International Stem Cell Registry located at the University of Massachusetts Medical School, Worcester, Mass., USA. These databases are periodically updated as cell lines become available and registration obtained. Some of which cell lines are not available for shipment NSCB Stem Cell Registry. Regardless, at least the below hES cell lines can be made commercially available as of the date of this present invention.

TABLE 2

| Human ES Cell Lines | |
|---|---|
| Institution (Country) | Name |
| U.S.A. | |
| BresaGen, Inc., Athens, Georgia (USA) | BG01, BG02, BG03; BG04; BG01v |
| Invitrogen (USA) | BG01v/hOG |

TABLE 2-continued

Human ES Cell Lines

| Institution (Country) | Name |
|---|---|
| CyThera, Inc., San Diego, California (USA) | CyT49, CyT203, CyT25 |
| Geron Corporation, Menlo Park, California (USA) | GE01, GE07, GE09, GE13, GE14, GE91, GE92 (H1, H7, H9, H13, H14, H9.1, H9.2) |
| University of California, San Francisco, California (USA) | UC01, UC06 (HSF-1, HSF-6); UCSFB1, UCSFB2, UCSFB3, UCSFB4, UCSFB5, UCSFB6, UCSFB7, UCSFB8, UCSFB9 & UCSFB10 |
| Wisconsin Alumni Research Foundation, Madison, Wisconsin (USA) | WA01, WA07, WA09, WA13, WA14 (H1, H7, H9, H13, H14) |
| Children's Hospital Corporation (USA) | CHB-1, CHB-2 CHB-3 CHB-4, CHB-5, CHB-6, CHB-8, CHB-9, CHB-10, CHB-11 & CHB-12 |
| The Rockefeller University (USA) | RUES1, RUES2 & RUES3 |
| Harvard University (USA) | HUES1, HUES2, HUES3, HUES4, HUES5, HUES6, HUES7, HUES8, HUES9, HUES10, HUES11, HUES12, HUES13, HUES14, HUES15, HUES16, HUES17, HUES18, HUES19, HUES20, HUES21, HUES22, HUES23, HUES24, HUES25, HUES26, HUES27; HUES28; HUES48; HUES49; HUES53; HUES55 & HUES 56 |
| Mt Sinai Hosp-Samuel Lunenfeld Research Institute (USA) | CA1 & CA2 |
| Children's Memorial Hospital (USA) | CM-1, CM-2, CM-5, CM-6, CM-7, CM-8, CM-11, CM-12, CM-13, CM-14, CM-16 |
| The University of Texas Health Science Center at Houston (USA) | CR1 & CR2 |
| California Stem Cell, Inc. (USA) | CSC14 |
| University of Connecticut School of Medicine/Dentistry (USA) | CSC14, CT1, CT2, CT3, & CT4 |
| The Third Affiliated Hospital of Guangzhou Medical College (USA) | FY-3PN; FY-hES-1; FY-hES-3; FY-hES-5; FY-hES-7 & FY-hES-8 |
| Advanced Cell Technology, Inc. (USA) | MA 01; MA 09; MA 42; MA 50; MA135; NED 1; NED 2; NED 3 & NED 4 |
| Stanford University (USA) | MFS5 |
| New York University School of Medicine (USA) | NYUES1; NYUES2; NYUES3; NYUES4; NYUES5; NYUES6 & NYUES7 |
| Reprogenetics, LLC (USA) | RNJ7 |
| University of California, Los Angeles (USA) | UCLA1; UCLA2 & UCLA3 |
| Eastern Virginia Medical School (USA) | ES-76; ES-78-1; ES-78-2 |
| Reproductive Genetics Institute (USA) | RG-222; RG-230; RG-249; RG-308; RG-313; RG-148; DYSTROPHIA MYOTONICA 1 (DM1), affected, 46,XY; RG-153; DYSTROPHIA MYOTONICA 1 (DM1), affected, 46,XX; RG-170; MUSCULAR DYSTROPHY, BECKER TYPE (BMD), affected, 46,XY; RG-186; HUNTINGTON DISEASE (HD), affected, 46,XX; RG-194; HUNTINGTON DISEASE (HD), affected, 46,XY; RG-233; HEMOGLOBIN BETA LOCUS (HBB), affected (HbS/HbS-sickle cell anemia), 46,XX; RG-245; EMERY-DREIFUSS MUSCULAR DYSTROPHY, X-LINKED (EDMD), carrier, 47,XXY; RG-246; EMERY-DREIFUSS MUSCULAR DYSTROPHY, X-LINKED (EDMD), affected, 46,XY; RG-271; TORSION DYSTONIA 1 (DYT1), AUTOSOMAL DOMINANT, affected (N/GAG del), 46,XY; RG-283; MUSCULAR DYSTROPHY, DUCHENNE TYPE (DMD), affected, 46,XY; RG-288; CYSTIC FIBROSIS (CF), affected (deltaF508/deltaF508), 46,XY; RG-289; CYSTIC FIBROSIS (CF), affected (deltaF508/deltaF508), 46,XX; RG-301; MUSCULAR DYSTROPHY, DUCHENNE TYPE (DMD) affected, 46,XY; RG-302; MUSCULAR DYSTROPHY, DUCHENNE TYPE (DMD), carrier, 46,XX; RG-315; NEUROFIBROMATOSIS, TYPE I (NF1), affected (R19 47X/N), 46,XY; RG-316; TUBEROUS SCLEROSIS, TYPE 1(TSC1), affected (N/IVS7 + 1 G-A); RG-316; TUBEROUS SCLEROSIS, TYPE 1(TSC1), affected (N/IVS7 + 1 G-A); RG-320; TUBEROUS SCLEROSIS, TYPE 1(TSC1), affected (N/IVS7 + 1 G-A); RG-326; POPLITEAL PTERYGIUM SYNDROME (PPS), affected (R84H/N), 46,XY; RG-328; FACIOSCAPULOHUMERAL MUSCULAR DYSTROPHY 1A(FSHD), affected, 46,XY; RG-330; FACIOSCAPULOHUMERAL MUSCULAR DYSTROPHY |

TABLE 2-continued

Human ES Cell Lines

| Institution (Country) | Name |
|---|---|
| | 1A (FSHD), affected, 46,XY;<br>RG-333; FACIOSCAPULOHUMERAL MUSCULAR DYSTROPHY 1A (FSHD), affected, 46,XX;<br>RG-356; HEMOGLOBIN ALPHA LOCUS (HBA), affected (−alpha/—), 46,XX;<br>RG-357; EMERY-DREIFUSS MUSCULAR DYSTROPHY, X-LINKED (EDMD), affected, 46,XY;<br>RG-358; EMERY-DREIFUSS MUSCULAR DYSTROPHY, X-LINKED (EDMD), affected, 46,XY;<br>RG-399; FACIOSCAPULOHUMERAL MUSCULAR DYSTROPHY 1A (FSHD), affected, 46,XX;<br>RG-401; FACIOSCAPULOHUMERAL MUSCULAR DYSTROPHY 1A (FSHD), affected, 46,XX;<br>RG-402; FACIOSCAPULOHUMERAL MUSCULAR DYSTROPHY 1A (FSHD), affected, 46,XX;<br>RG-403; FACIOSCAPULOHUMERAL MUSCULAR DYSTROPHY 1A (FSHD), affected;<br>RG-404; SPINAL MUSCULAR ATROPHY, TYPE I (SMA1), affected, 46,XY;<br>RG-406; TORSION DYSTONIA 1, AUTOSOMAL DOMINANT (DYT1), affected (N/GAG del);<br>RG-413; BREAST CANCER, FAMILIAL (BRCA2), affected (N/IVS7 GT del) & MULTIPLE ENDOCRINE NEOPLASIA, TYPE I (MEN1), affected (N/3036 4 bp del);<br>RG-414; MULTIPLE ENDOCRINE NEOPLASIA, TYPE I (MEN1), affected (N/3036 4 bp del);<br>RG-415; HUNTINGTON DISEASE (HD), affected;<br>RG-416; CYSTIC FIBROSIS (CF), affected (deltaF508/1717-1 G-A);<br>RG-417; CYSTIC FIBROSIS (CF), affected (deltaF508/1717-1 G-A);<br>RG-418; HEMOGLOBIN BETA LOCUS (HBB), affected (cd8 + G/619del);<br>RG-420; HEMOGLOBIN BETA LOCUS (HBB), affected (cd8 + G/619del);<br>RG-422; CYSTIC FIBROSIS (CF), affected (N1303K/deltaF508);<br>RG-423; CYSTIC FIBROSIS (CF), carrier (N/deltaF508);<br>RG-424; MULTIPLE ENDOCRINE NEOPLASIA, TYPE 2 (MEN2B), affected (M918T/N);<br>RG-426; PELIZAEUS-MERZBACHER DISEASE (PMLD), affected;<br>RG-428; TUBEROUS SCLEROSIS, TYPE 1 (TSC1), affected (N/IVS7 + 1 G-A) |

South American

| Institution (Country) | Name |
|---|---|
| Instituto de Biociências, São Paulo (Brazil) | BR-1 |

Middle East

| Institution (Country) | Name |
|---|---|
| Technion-Israel Institute of Technology, Haifa (Israel) | TE03, TE04, TE06 (I 3, I 4, I 6) |
| Hadassah University Hospital (Israel) | HAD 1; HAD 2; HAD 3; HAD 4; HAD 5; HAD 6 |
| Hebrew University of Jerusalem | HEFX1 |
| Technion - Israel Institute of Technology | I3; I3.2; I3.3; 14; 16; 16.2; J3; J3.2 |
| Royan Institute (Iran) | ARMD.1.H.iPSC.2; BOM.1.H.iPSC.1; CNS.1.H.iPSC.10; CNS.2.H.iPSC.7; FHC.1.H.iPSC.3; GSD.1.H.iPSC.7; HER.1.H.iPSC.1; LCA.1.H.iPSC.1; LHON.1.H.iPSC.5; R.1.H.iPSC.1; R.1.H.iPSC.4; R.1.H.iPSC.9; Royan H1; Royan H10; Royan H2; Royan H3; Royan H4; Royan H5; Royan H6; Royan H7; Royan H8; Royan H9; RP.1.H.iPSC.2; RP2.H.iPSC.3; TYR.1.H.iPSC.1; USH.1.H.iPSC.6 |

Europe

| Institution (Country) | Name |
|---|---|
| Cellartis AB, Gotenberg (Sweden) | SA001, SA002 (Sahlgrenska 1, Sahlgrenska 2); SA002.2; SA003; AS034.1; AS034.1.1; AS034.2; AS038; AS046; FC018; ASo85; AS094; SA111; SA121; SA142; SA167; SA181; SA191; SA196; SA202; SA203; SA211; SA218; SA240; SA279; SA348; SA352; SA399; SA461; SA502; SA506; SA521; SA540; SA611 |
| Karolinska Institutet (Sweden) | HS181; HS207; HS235; HS237; HS293; HS306; HS346; HS351; HS356; HS360; HS361; HS362; HS363; HS364; HS366; HS368; HD380; HS382; HS400; HS401; HS402; HS415; HS420; HS422; HS426; HS429; HS429A; HS429B; HS429C; HS429D; HS475; HS480; HS481; HS539 |
| Göteborg University, Göteborg (Sweden) | SA04-SA19 (Sahlgrenska 4-Sahlgrenska 19) |
| Karolinska Institute, Stockholm (Sweden) | KA08, KA09, KA40, KA41, KA42, KA43 (hICM8, hICM9, hICM40, hICM41, hICM42, hICM43) |
| Geneva University (Switzerland) | CH-ES1 |
| University of Basel (Switzerland) | CH-ES3; CH-ES3; CH-ES5 |
| Roslin Cells Ltd (UK) | RC2; RC3; RC4; RC5 |

TABLE 2-continued

Human ES Cell Lines

| Institution (Country) | Name |
|---|---|
| University of Newcastle upon Tyne (UK) | NCL-1; NCL-2; NCL-3; NCL-4; NCL-5; NCL-6; NCL-7; NCL-8; NCL-9 |
| Roslin Institute (Edinburgh) & Geron Corporation (UK) | RH1; RH2; RH3; RH4; RH5; RH6; RH7; RH9; |
| University of Manchester (UK) | Man 2 |
| King's College London (UK) | KCL-001 (formerly WT3) |
| The University of Sheffield, Sheffield (UK) | SHEF-1; SHEF-2; SHEF-3; SHEF-4; SHEF-5; SHEF-6; SHEF-7; SHEF-8 |
| Universities of Edinburgh & Oxford; University of Cambridge (UK) | Edi-1; Edi-2; Edi-3; Edi-4 |
| Roslin Cells Ltd, Roslin Institute, Universities of Edinburgh & Manchester, Central Manchester & Manchester Children's University Hospitals NHS Trust (UK) | RCM-1; RC-1; RC-2; RC-3; RC-4; RC-5; RC-6; RC-7; RC-8; RC-9; RC-10 |
| King's College London & Guy's Hospital Trust/Charitable Foundation of Guy's & St Thomas (UK) | KCL-003-CF1 (formerly CF1); KCL-005-HD1; KCL008-HD-2; KCL009-trans-1; KCL-001 (WT-3); KCL-001 (WT-4) |
| Stem Cell Sciences Ltd, Australia (SCS) & Australian Stem Cell Centre (ASCC) | MEL-1; MEL-2; MEL-3; MEL-4 |
| University of Edinburgh (UK) | CB660 |
| Axordia Ltd. (UK) | Shef-1; Shef-2; Shef-3; Shef-4; Shef-5; Shef-6; Shef-7 |
| University of Nottingham (UK) | Nott-1; Nott-2 |
| Centre of Regenerative Medicine in Barcelona (Spain) | ES-2; ES-3; ES-4; ES-5; ES-6; ES-7; ES-8; ES-9; ES-10; ES-11EM; cFA404-KiPS4F-1; cFA404-KiPS4F-3; KiPS3F-7; KiPS4F-1; KiPS4F-8 |
| Principe Felipe Centro de Investigacion (Spain) | VAL-3; VAL-4; VAL-5; VAL-6M; VAL-7; VAL-8; VAL-9; VAL-10B |
| Université Libre de Bruxelles (Belgium) | ERA-1; ERA2; ERA-3; ERAMUC-1; ERAMUC-1 |
| Vrije Universiteit Brussel (Belgium) | VUB01; VUB02; VUB06; VUB07; VUB03_DM1; VUB04_CF; VUB05_HD; VUB08_MFS; VUB09_FSHD; VUB10_SCA7; VUB11_FXS; VUB13_FXS; VUB14; VUB19_DM1; VUB20_CMT1A; VUB22_CF; VUB23_OI; VUB24_DM1; VUB26; VUB27; VUB28_HD_MFS |
| Central Manchester and Manchester Children's University Hospitals NHS (UK) | Man 1; Man 2 |
| Université Paris-Sud 11 (France) | CL01; CL02; CL03; PB04; PB05; PB05-1; PB06; PB06-1; PB07; PB08; PB09; PB10 |
| INSERM (France) | OSCAR; STR-I-155-HD; STR-I-171-GLA; STR-I-189-FRAXA; STR-I-203-CFTR; STR-I-209-MEN2a; STR-I-211-MEN2a; STR-I-221-Sca2; STR-I-229-MTMX; STR-I-231-MTMX; STR-I-233-FRAXA; STR-I-251-CFTR; STR-I-301-MFS; STR-I-305-APC; STR-I-315-CMT1a; STR-I-347-FRAXA; STR-I-355-APC; STR-I-359-APC |
| Masaryk University (Czech Republic) | CCTL 6; CCTL 8; CCTL 9; CCTL 10; CCTL 12; CCTL 13; CCRL 14 |
| Aalborg University (Denmark) | CLS1; CLS2; CLS3; CLS4 |
| University of Copenhagen (Denmark) | LRB001; LRB002; LRB003; LRB004; LRB005; LRB006; LRB007; LRB008; LRB009; LRB010; LRB011; LRB013; LRB014; LRB016; LRB017; LRB018; |
| University of Southern Denmark | KMEB1; KMEB2; KMEB3; KMEB4; KMEB |
| University of Helsinki (Finland) | FES21; FES22; FES29; FES30; FES61; FES75 |
| University of Tampere (Finland) | Regea 06/015; Regea 06/040; Regea 07/027; Regea 07/046; Regea 08/013; Regea 08/017; Regea 08/023; Regea 08/056 |
| Leiden University Medical Center (Netherlands) | HESC-NL1; HESC-NL2; HESC-NL3; HESC-NL4 |
| Russian Academy of Sciences (Russia) | ESM01; ESM02; ESM03; |
| Instanbul Memorial Hospital (Turkey) | MINE: NS-2; NS-3; NS-4; NS-5; NS-6; NS-7; NS-8; NS-9; NS-10; OZ-1; OZ-2; OZ-3; OZ-4; OZ-5; OZ-6; OZ-7; OZ-8 |
| Australia | |
| Monash University (Australia) | Envy |
| Prince of Wales Hospital, Sydney (Australia) | E1C1; E1C2; E1C3; E1C4; Endeavour 1; Endeavour 2; hES3.1; hES3.2; hES3.3 |
| Sydney IVF Limited (Australia) | SIVF01; SIVF03; SIVF05; SIVF06; SIVF07; SIVF08; SIVF09; SIVF10; SIVF11; SIVF12; SIVF13 |
| Asia | |
| Kyoto University (Japan) | 201B1; 201B2; 201B3; 201B6; 201B7; 243H1; 243H7; 246G1; 246G3; 246G4; 246G5; 246G6; khES-1; khES-2; khES-3; |
| Singapore Stem Cell Consortium | ESI-013; ESI-014; ESI-017; ESI-027; ESI-035; ESI-049; ESI-051; ESI-053 |

TABLE 2-continued

Human ES Cell Lines

| Institution (Country) | Name |
|---|---|
| ES Cell International Pte Ld (Singapore) | ES01, ES02, ES03, ES04, ES05, ES06 (HES-1, HES-2, HES-3, HES-4, HES-5, HES-6 |
| Maria Biotech Co. Ltd. - Maria Infertility Hospital Medical Institute, Seoul (Korea) | MB01, MB02, MB03; MB04; MB05; MB06; MB07; MB08; MB09 |
| MizMedi Hospital—Seoul National University, Seoul (Korea) | MI01 (Miz-hES1); Miz-hES2; Miz-hES3; Miz-hES4; Miz-hES5; Miz-hES6; Miz-hES7; Miz-hES8; Miz-hES9; Miz-hES10; Miz-hES11; Miz-hES12; Miz-hES13; Miz-hES14; Miz-hES15; |
| Pochon CHA University College of Medicine (Korea) | CHA-hES3; CHA-hES4 |
| Seoul National University (Korea) | SNUhES1; SNUhES2; SNUhES3; SNUhES4; SNUhES11; SNUhES16 |
| National Centre for Biological Sciences/Tata Institute of Fundamental Research, Bangalore (India) | NC01, NC02, NC03 (FCNCBS1, FCNCBS2, FCNCBS3); BJN-hem19; BJN-hem20 |
| Reliance Life Sciences, Mumbai (India) | RL05, RL07, RL10, RL13, RL15, RL20, RL21 (RLS ES 05, RLS ES 07, RLS ES 10 |
| National Institute for Research in Reproductive Health (India) | KIND-1; KIND-2 |
| Tata Institute of Fundamental Research (India) | FCNCBS1; FCNCBS2; FCNCBS3 |
| Kaohsiung Medical University (Taiwan) | T1; T2; T3; T4; T5 |
| Central South University (China) | chESC-3 (H3); chESC-8; chESC-20; chESC-22; EBNA1 + H9 |
| Graduate University of Chinese Academy of Sciences (China) | hPES-1; hPES-2 |
| Huazhong University of Science and Technology (China) | hES-8; hES18 |
| Peking University Third Hospital (China) | B4; B7; PKU1; PKU2 |
| Shanghai Jiao Tong University School of Medicine (China) | SHhES1 |
| Shanghei Second Medical University (China) | SH1; SH2; SH4; SH7; SH28; SH35; SH35a; SH38; SH39; SH42 |
| Sun Yat-sen University (China) | CHES-1; SYSU-1; SYSU-2 |
| Sun Yat-sen University Second Affiliated Hospital (China) | CHE-1; CHE-2; CHE-3 |
| The Third Affiliated Hospital of Guangzhou Medical College (China) | FY-hES-5; FY-hES-9; FY-hES-10;; FY-hES-11 |

TABLE 3

Listing of Human Induced Pluripotent Stem (hIPS) Cell Lines

| Institution | Cell Line |
|---|---|
| University of Wisconsin - Madison (USA) | 1. IPS(FORESKIN)-1 (Normal; 46XY; Yu, J., et al. [Thomson] Science. 2007 Induced pluripotent stem cell lines derived from human somatic cells 318(5858): 1917-20.) <br> 2. IPS(FORESKIN)-2 (Normal; 46XY; Yu, J., et al. [Thomson] Science. 2007 Induced pluripotent stem cell lines derived from human somatic cells 318(5858): 1917-20.) <br> 3. IPS(FORESKIN)-3 (Normal; 46XY; Yu, J., et al. [Thomson] Science. 2007 Induced pluripotent stem cell lines derived from human somatic cells 318(5858): 1917-20.) <br> 4. IPS(FORESKIN)-4 (Normal; 46XY; Yu, J., et al. [Thomson] Science. 2007 Induced pluripotent stem cell lines derived from human somatic cells 318(5858): 1917-20.) <br> 5. IPS(IMR90)-1 (Normal; 46XX; Yu, J., et al. [Thomson] Science. 2007 Induced pluripotent stem cell lines derived from human somatic cells 318(5858): 1917-20.) <br> 6. IPS(IMR90)-2 (Normal; 46XX; Yu, J., et al. [Thomson] Science. 2007 Induced pluripotent stem cell lines derived from human somatic cells 318(5858): 1917-20.) <br> 7. IPS(IMR90)-3 (Normal; 46XX; Yu, J., et al. [Thomson] Science. 2007 Induced pluripotent stem cell lines derived from human somatic cells 318(5858): 1917-20.) <br> 8. IPS(IMR90)-4 (Normal; 46XX; Yu, J., et al. [Thomson] Science. 2007 Induced pluripotent stem cell lines derived from human somatic cells 318(5858): 1917-20.) <br> 9. IPS-SMA-3.5 (Normal; 46XY; Type 1 Spinal Muscular Atrophy; Ebert, A. D., et al. 2009. Induced pluripotent stem cells from a spinal muscular atrophy patient Nature. 457: 277-80) <br> 10. IPS-SMA-3.6 (Normal; 46XY; Type 1 Spinal Muscular Atrophy; Ebert, A. D., et al. 2009. Induced pluripotent stem cells from a spinal muscular atrophy patient Nature. 457: 277-80) <br> 11. IPS-WT (Normal; 46XX; Type 1 Spinal Muscular Atrophy; Ebert, A. D., et al. 2009. Induced pluripotent stem cells from a spinal muscular atrophy patient Nature. 457: 277-80) |

TABLE 3-continued

Listing of Human Induced Pluripotent Stem (hIPS) Cell Lines

| Institution | Cell Line |
| --- | --- |
| University of California, Los Angeles (USA) | 1. IPS-1 (Karumbayaram, S. et al. 2009. Directed Differentiation of Human-Induced Pluripotent Stem Cells Generates Active Motor NeuronsStem Cells. 27: 806-811; Lowry, W. E., et al.. 2008. Generation of human induced pluripotent stem cells from dermal fibroblasts Proc Natl Acad Sci USA. 105: 2883-8)<br>2. IPS-2 (Karumbayaram, S. et al. 2009. Directed Differentiation of Human-Induced Pluripotent Stem Cells Generates Active Motor NeuronsStem Cells. 27: 806-811; Lowry, W. E., et al.. 2008. Generation of human induced pluripotent stem cells from dermal fibroblasts Proc Natl Acad Sci USA. 105: 2883-8)<br>3. IPS-5 (Lowry, W. E., et al.. 2008. Generation of human induced pluripotent stem cells from dermal fibroblasts Proc Natl Acad Sci USA. 105: 2883-8)<br>4. IPS-7 (Lowry, W. E., et al.. 2008. Generation of human induced pluripotent stem cells from dermal fibroblasts Proc Natl Acad Sci USA. 105: 2883-8)<br>5. IPS-18 (Karumbayaram, S. et al. 2009. Directed Differentiation of Human-Induced Pluripotent Stem Cells Generates Active Motor NeuronsStem Cells. 27: 806-811; Lowry, W. E., et al.. 2008. Generation of human induced pluripotent stem cells from dermal fibroblasts Proc Natl Acad Sci USA. 105: 2883-8)<br>6. IPS-24 (Lowry, W. E., et al.. 2008. Generation of human induced pluripotent stem cells from dermal fibroblasts Proc Natl Acad Sci USA. 105: 2883-8)<br>7. IPS-29 (Lowry, W. E., et al.. 2008. Generation of human induced pluripotent stem cells from dermal fibroblasts Proc Natl Acad Sci USA. 105: 2883-8) |
| Mt. Sinai Hospital (Samuel Lunenfeld Research Institute; USA) | 1. (Woltjen, K. et al. 2009. PiggyBac transposition reprograms fibroblasts to induced pluripotent stem cells Nature. 458(7239): 766-70)<br>2. 61 (Woltjen, K. et al. 2009. PiggyBac transposition reprograms fibroblasts to induced pluripotent stem cells Nature. 458(7239): 766-70)<br>3. 66 (Woltjen, K. et al. 2009. PiggyBac transposition reprograms fibroblasts to induced pluripotent stem cells Nature. 458(7239): 766-70)<br>4. 67 (Woltjen, K. et al. 2009. PiggyBac transposition reprograms fibroblasts to induced pluripotent stem cells Nature. 458(7239): 766-70)<br>5. HIPSC117 (Kaji K, et al. 2009 Virus-free induction of pluripotency and subsequent excision of reprogramming factors Nature 458(7239): 771-5)<br>6. HIPSC121 (Kaji K, et al. 2009 Virus-free induction of pluripotency and subsequent excision of reprogramming factors Nature 458(7239): 771-5)<br>7. HIPSC122 (Kaji K, et al. 2009 Virus-free induction of pluripotency and subsequent excision of reprogramming factors Nature 458(7239): 771-5) |
| Children's Hospital - Boston (USA) | 1. 551-IPS8 (Park I H, et al. 2008. Reprogramming of human somatic cells to pluripotency with defined factors. Nature 451: 141-6).<br>2. ADA-IPS2 ((ADA-SCID) Adenosine Deaminase Deficiency-related Severe Combined Immunodeficiency (GGG>AGG, exon 7, ADA gene); Park, I. H. et al. 2008. Disease-Specific Induced Pluripotent Stem Cells Cell134(5): 877-86)<br>3. ADA-IPS3 ((ADA-SCID) Adenosine Deaminase Deficiency-related Severe Combined Immunodeficiency (GGG>AGG, exon 7, ADA gene); Park, I. H. et al. 2008. Disease-Specific Induced Pluripotent Stem Cells Cell134(5): 877-86)<br>4. BJ1-IPS1 (Park, I. H. et al. 2008. Disease-Specific Induced Pluripotent Stem Cells Cell134(5): 877-86)<br>5. BMD-IPS1 (Male; (BMD) Becker Muscular Dystrophy (Unidentified mutation in dystrophin); Park, I. H. et al. 2008. Disease-Specific Induced Pluripotent Stem Cells Cell134(5): 877-86)<br>6. BMD-IPS4 (Normal; 46XY; (BMD) Becker Muscular Dystrophy (Unidentified mutation in dystrophin); Park, I. H. et al. 2008. Disease-Specific Induced Pluripotent Stem Cells Cell134(5): 877-86)<br>7. DH1CF16-IPS1 (Normal; 46XY; Park, I. H. et al. 2008. Disease-Specific Induced Pluripotent Stem Cells Cell134(5): 877-86)<br>8. DH1CF32-IPS2 (Male; Park, I. H. et al. 2008. Disease-Specific Induced Pluripotent Stem Cells Cell134(5): 877-86)<br>9. DH1F-IPS3-3(Normal; 46XY; Park, I. H. et al. 2008. Disease-Specific Induced Pluripotent Stem Cells Cell134(5): 877-86)<br>10. DMD-IPS1 ((Normal; 46XY; DMD) Duchenne Muscular Dystrophy (Deletion of exon 45-52, dystrophin gene; Park, I. H. et al. 2008. Disease-Specific Induced Pluripotent Stem Cells Cell134(5): 877-86)<br>11. DMD-IPS2 (Male; (DMD) Duchenne Muscular Dystrophy (Deletion of exon 45-52, dystrophin gene; Park, I. H. et al. 2008. Disease-Specific Induced Pluripotent Stem Cells Cell134(5): 877-86)<br>12. DS1-IPS4 (Male; Down syndrome (Trisomy 21); Park, I. H. et al. 2008. Disease-Specific Induced Pluripotent Stem Cells Cell134(5): 877-86)<br>13. DS2-IPS1 (Male; Down syndrome (Trisomy 21); Park, I. H. et al. 2008. Disease-Specific Induced Pluripotent Stem Cells Cell134(5): 877-86)<br>14. DS2-IPS10 (Male; Down syndrome (Trisomy 21); Park, I. H. et al. 2008. Disease-Specific Induced Pluripotent Stem Cells Cell134(5): 877-86)<br>15. GD-IPS1(Male; (GD) Gaucher Disease type III (AAC > AGC, exon 9, G-insertion, nucleotide 84 of cDNA, GBA gene; Park, I. H. et al. 2008. Disease-Specific Induced Pluripotent Stem Cells Cell134(5): 877-86)<br>16. GD-IPS3 (Male; (GD) Gaucher Disease type III (AAC > AGC, exon 9, G-insertion, nucleotide 84 of cDNA, GBA gene; Park, I. H. et al. 2008. Disease-Specific Induced Pluripotent Stem Cells Cell134(5): 877-86)<br>17. HFIB2-IPS2 (Park, I. H., et al. 2008. Generation of human-induced pluripotent stem cells Nat Protoc. 3: 1180-6; Park, I. H. et al. 2008. Reprogramming of human somatic |

TABLE 3-continued

Listing of Human Induced Pluripotent Stem (hIPS) Cell Lines

| Institution | Cell Line |
|---|---|
| | cells to pluripotency with defined factors Nature. 451: 141-6)<br>18. HFIB2-IPS4 (Park, I. H., et al. 2008. Generation of human-induced pluripotent stem cells Nat Protoc. 3: 1180-6; Park, I. H. et al. 2008. Reprogramming of human somatic cells to pluripotency with defined factors Nature. 451: 141-6)<br>19. HFIB2-IPS5 (Park, I. H., et al. 2008. Generation of human-induced pluripotent stem cells Nat Protoc. 3: 1180-6; Park, I. H. et al. 2008. Reprogramming of human somatic cells to pluripotency with defined factors Nature. 451: 141-6)<br>20. JDM-IPS1 (Normal, 46XX; Juvenile diabetes mellitus (multifactorial); Park, I. H. et al. 2008. Disease-Specific Induced Pluripotent Stem Cells Cell134(5): 877-86)<br>21. JDM-IPS1 (Normal, 46XX; Juvenile diabetes mellitus (multifactorial); Park, I. H. et al. 2008. Disease-Specific Induced Pluripotent Stem Cells Cell134(5): 877-86)<br>22. JDM-IPS2 (Female; Juvenile diabetes mellitus (multifactorial); Park, I. H. et al. 2008. Disease-Specific Induced Pluripotent Stem Cells Cell134(5): 877-86)<br>23. JDM-IPS3 (Female; Juvenile diabetes mellitus (multifactorial); Park, I. H. et al. 2008. Disease-Specific Induced Pluripotent Stem Cells Cell134(5): 877-86)<br>24. LNSC-IPS2 (Female; Lesch-Nyhan syndrome (carrier, heterozygosity of HPRT1; Park, I. H. et al. 2008. Disease-Specific Induced Pluripotent Stem Cells Cell134(5): 877-86)<br>25. MRC5-IPS7 (Male; Park, I. H. et al. 2008. Disease-Specific Induced Pluripotent Stem Cells Cell134(5): 877-86)<br>26. MRC5-IPS12 (Normal; 46XY; Park, I. H. et al. 2008. Disease-Specific Induced Pluripotent Stem Cells Cell134(5): 877-86)<br>27. MRC5-IPS1 (Male; Park, I. H. et al. 2008. Disease-Specific Induced Pluripotent Stem Cells Cell134(5): 877-86)<br>28. PD-IPS1 (Male; Parkinson disease (multifactorial); Park, I. H. et al. 2008. Disease-Specific Induced Pluripotent Stem Cells Cell134(5): 877-86)<br>29. SBDS-IPS1 (Male; Swachman-Bodian-Diamond syndrome (IV2 + 2T>C and IV3 − 1G>A, SBDS gene; Park, I. H. et al. 2008. Disease-Specific Induced Pluripotent Stem Cells Cell134(5): 877-86)<br>30. SBDS-IPS2<br>31. SBDS-IPS3 (Normal; 46XY; Swachman-Bodian-Diamond syndrome (IV2 + 2T>C and IV3 − 1G>A, SBDS gene; Park, I. H. et al. 2008. Disease-Specific Induced Pluripotent Stem Cells Cell134(5): 877-86) |
| Harvard University (USA) | 1. A29a (46XX; (ALS) Amyotrophic Lateral Sclerosis (L144F [Leu144 > Phe] dominant allele of the superoxide dismutase (SOD1) gene; Caucasian; Dimos, J. T., et al. 2008. Induced pluripotent stem cells generated from patients with ALS can be differentiated into motor neurons Science. 321: 1218-21)<br>2. A29b (46XX; (ALS) Amyotrophic Lateral Sclerosis (L144F [Leu144 > Phe] dominant allele of the superoxide dismutase (SOD1) gene; Caucasian; Dimos, J. T., et al. 2008. Induced pluripotent stem cells generated from patients with ALS can be differentiated into motor neurons Science. 321: 1218-21)<br>3. A29c (46XX; (ALS) Amyotrophic Lateral Sclerosis (L144F [Leu144 > Phe] dominant allele of the superoxide dismutase (SOD1) gene; Caucasian; Dimos, J. T., et al. 2008. Induced pluripotent stem cells generated from patients with ALS can be differentiated into motor neurons Science. 321: 1218-21) |
| Salk Institute (USA) | 1. HAIR-IPS1 (Aasen, T., et al.[Belmonte, J. C.] 2008. Efficient and rapid generation of induced pluripotent stem cells from human keratinocytes Nat Biotechnol. 26: 1276-84)<br>2. HAIR-IPS2 (Aasen, T., et al.[Belmonte, J. C.] 2008. Efficient and rapid generation of induced pluripotent stem cells from human keratinocytes Nat Biotechnol. 26: 1276-84) |
| Royan Institute (Iran) | 1. R.1.H.iPSC.1(OCT4, Sox2, KLF4, c-Myc; Human fibroblasts)<br>2. BOM.1.H.iPSC.1 (OCT4, Sox2, KLF4, c-Myc; Human fibroblasts)<br>3. FHC.1.H.iPSC.3 (OCT4, Sox2, KLF4, c-Myc; Human fibroblasts)<br>4. GSD.1.H.iPSC.7 (OCT4, Sox2, KLF4, c-Myc; Human fibroblasts)<br>5. TYR.1.H.iPSC.1 (OCT4, Sox2, KLF4, c-Myc; Human fibroblasts)<br>6. HER.1.H.iPSC.1 (OCT4, Sox2, KLF4, c-Myc; Human fibroblasts)<br>7. R.1.H.iPSC.4 (OCT4, Sox2, KLF4, c-Myc; Human fibroblasts)<br>8. R.1.H.iPSC.9 (OCT4, Sox2, KLF4, c-Myc; Human fibroblasts)<br>9. RP2.H.iPSC.3 (OCT4, Sox2, KLF4, c-Myc; iPS cells)<br>10. LCA.1.H.iPSC.1 (OCT4, Sox2, KLF4, c-Myc; iPS cells)<br>11. USH.1.H.iPSC.6 (OCT4, Sox2, KLF4, c-Myc; Human fibroblasts)<br>12. RP.1.H.iPSC.2 (OCT4, Sox2, KLF4, c-Myc; Human fibroblasts)<br>13. ARMD.1.H.iPSC.2 (OCT4, Sox2, KLF4, c-Myc; Human fibroblasts)<br>14. LHON.1.H.iPSC.5 (OCT4, Sox2, KLF4, c-Myc; iPS cells)<br>15. CNS.1.H.iPSC.10 (OCT4, Sox2, KLF4, c-Myc; iPS cells)<br>16. CNS.2.H.iPSC.7 (OCT4, Sox2, KLF4, c-Myc; iPS cells) |
| Centre of Regenerative Medicine in Barcelona (Spain) | 1. KiPS4F-1 (OCT4, Sox2, KLF4, c-Myc; human foreskin keratinocytes; 46XY)<br>2. KiPS3F-7 (OCT4, Sox2, KLF4); human foreskin keratinocytes)<br>3. KiPS4F-8 (OCT4, Sox2, KLF4, c-Myc human foreskin keratinocytes; 46XY)<br>4. cFA404-KiPS4F-1 (OCT4, Sox2, KLF4, c-Myc; Epidermal keratinocytes; 46XY)<br>5. cFA404-KiPS4F-3 (OCT4, Sox2, KLF4, c-Myc; Epidermal keratinocytes; 46XY) |
| Université Paris-Sud 11 (France) | 1. PB03 (Oct4, Sox2, Lin28, Nanog; Primary Amniocytes; 46XX; Lentivirus)<br>2. PB04 (Oct4, Sox2, Lin28, Nanog; Primary Amniocytes; Beta-Thalassemia affected; 46XY; Lentivirus)<br>3. PB05-1 (Oct4, Sox2, Lin28, Nanog; Primary Amniocytes; Beta-Thalassemia affected; 46XY; Lentivirus)<br>4. PB05 (Oct4, Sox2, Lin28, Nanog; Primary Amniocytes; Beta-Thalassemia affected; 46XY; Lentivirus) |

TABLE 3-continued

Listing of Human Induced Pluripotent Stem (hIPS) Cell Lines

| Institution | Cell Line |
|---|---|
| | 5. PB06 (Oct4, Sox2, Lin28, Nanog; Primary Amniocytes; Down Syndrome; 47XY, +21; Lentivirus) |
| | 6. PB06-1 (Oct4, Sox2, Lin28, Nanog; Primary Amniocytes; Down Syndrome; 47XY, +21; Lentivirus) |
| | 7. PB07 (OCT4, Sox2, KLF4, c-Myc; Primary Amniocytes; 46XY; Retrotivirus) |
| | 8. PB08 (OCT4, Sox2, KLF4, c-Myc; Primary Amniocytes; 46XY; Retrotivirus) |
| | 9. PB09 (Oct4, Sox2, Lin28, Nanog; Primary Amniocytes; 46XY; Lentivirus) |
| | 10. PB10 (Oct4, Sox2; Primary Amniocytes46XY, Lentivirus) |
| Kyoto University (Japan) | 1. 201B1 (human fibroblast; 46XX) |
| | 2. 201B2 (human fibroblast; 46XX) |
| | 3. 201B3 (human fibroblast; 46XX) |
| | 4. 201B6 (human fibroblast; 46XX) |
| | 5. 201B7 (human fibroblast; 46XX) |
| | 6. 243H1 (human fibroblast) |
| | 7. 243H7 (human fibroblast) |
| | 8. 246B1 (Normal, 46XX) |
| | 9. 246B2 (Normal, 46XX) |
| | 10. 246B3 (Normal, 46XX) |
| | 11. 246B4 (Normal, 46XX) |
| | 12. 246B5 (Normal, 46XX) |
| | 13. 246B6 (Normal, 46XX) |
| | 14. 246G1 (human fibroblast; Takahashi, K., et al. 2007. Induction of pluripotent stem cells from adult human fibroblasts by defined factors Cell. 131: 861-72) |
| | 15. 246G3 (human fibroblast; Takahashi, K., et al. 2007. Induction of pluripotent stem cells from adult human fibroblasts by defined factors Cell. 131: 861-72) |
| | 16. 246G4 (human fibroblast; Takahashi, K., et al. 2007. Induction of pluripotent stem cells from adult human fibroblasts by defined factors Cell. 131: 861-72) |
| | 17. 246G5 (human fibroblast; Takahashi, K., et al. 2007. Induction of pluripotent stem cells from adult human fibroblasts by defined factors Cell. 131: 861-72) |
| | 18. 246G6 (human fibroblast; Takahashi, K., et al. 2007. Induction of pluripotent stem cells from adult human fibroblasts by defined factors Cell. 131: 861-72) |
| | 19. 253F1 (Normal, 46XX; Takahashi, K., et al. 2007. Induction of pluripotent stem cells from adult human fibroblasts by defined factors Cell. 131: 861-72) |
| | 20. 253F2 (Normal, 46XX; Takahashi, K., et al. 2007. Induction of pluripotent stem cells from adult human fibroblasts by defined factors Cell. 131: 861-72) |
| | 21. 253F3 (Normal, 46XX; Takahashi, K., et al. 2007. Induction of pluripotent stem cells from adult human fibroblasts by defined factors Cell. 131: 861-72) |
| | 22. 253F4 (Normal, 46XX; Takahashi, K., et al. 2007. Induction of pluripotent stem cells from adult human fibroblasts by defined factors Cell. 131: 861-72) |
| | 23. 253F5 (Normal, 46XX; Takahashi, K., et al. 2007. Induction of pluripotent stem cells from adult human fibroblasts by defined factors Cell. 131: 861-72) |
| Shanghai Institutes for Biological Sciences (China) | 1. HAFDC-IPS-6 (Li C., et al. 2009 Pluripotency can be rapidly and efficiently induced in human amniotic fluid-derived cells Hum Mol Genet. 2009 Nov 15; 18(22): 4340-9) |
| | 2. IPS-S (Liao, J., et al. 2008. Enhanced efficiency of generating induced pluripotent stem (iPS) cells from human somatic cells by a combination of six transcription factors Cell Res. 18: 600-3) |

Example 1

Identification of Compounds Cytotoxic to hES Cells but not Differentiated Cells

Screening For Candidate Compounds Inhibiting or Cytotoxic to Human Embryonic Stem Cells (hESCs). Certain compounds were selected from the Library of Pharmacologically Active Compounds (LOPAC), specifically the LOPAC1280™ collection (Sigma-Aldrich, Catalog No. LO1280). LOPAC1280™ compounds are known or have well characterized properties. The full list of LOPAC1280™ can be viewed on the world wide web at sigmaaldrich.com/chemistry/drug-discovery/validation-libraries/lopac1280-navigator.html. Initial screening was performed using a subset of the LOPAC1280™ library consisting of 176 compounds that were selected because they were known inhibitors of cell signaling pathways, phosphorylation events, or receptors and the like. See Table 4, listing the selected 176 compounds. These compounds were arrayed in 2×96 well trays, including control wells containing DMSO.

TABLE 4

176 Selected LOPAC1280 ™ Compounds

| No. | Compound | Action |
|---|---|---|
| 1 | Acetamide | Inhibitor |
| 2 | O-(Carboxymethyl) hydroxylamine hemihydrochloride | Inhibitor |
| 3 | Actinonin | Inhibitor |
| 4 | S(−)-p-Bromotetramisole oxalate | Inhibitor |
| 5 | Acetazolamide | Inhibitor |
| 6 | 4-Androsten-4-ol-3,17-dione | Inhibitor |
| 7 | Adenosine 3',5'-cyclic monophosphate | Activator |
| 8 | Diacylglycerol kinase inhibitor I | Inhibitor |
| 9 | Fulvestrant | SERD |
| 10 | 4-(2-Aminoethyl)benzenesulfonyl fluoride hydrochloride | Inhibitor |
| 11 | TBBz | Inhibitor |
| 12 | L-allylglycine | Inhibitor |
| 13 | Betaine hydrochloride | Metabolite |
| 14 | SB 202190 | Inhibitor |
| 15 | Budesonide | |
| 16 | BTO-1 | Inhibitor |
| 17 | Benzamidine hydrochloride | Inhibitor |
| 18 | ML-9 | Inhibitor |
| 19 | Betamethasone | |

TABLE 4-continued

176 Selected LOPAC1280 ™ Compounds

| No. | Compound | Action |
|---|---|---|
| 20 | Bestatin hydrochloride | Inhibitor |
| 21 | Corticosterone | |
| 22 | Benserazide hydrochloride | Inhibitor |
| 23 | DAPH | Inhibitor |
| 24 | Cortisone | |
| 25 | Chelerythrine chloride | Inhibitor |
| 26 | Cyclosporin A | Inhibitor |
| 27 | Roscovitine | Inhibitor |
| 28 | Cantharidin | Inhibitor |
| 29 | Chlorothiazide | Inhibitor |
| 30 | beta-Chloro-L-alanine hydrochloride | Inhibitor |
| 31 | Calmidazolium chloride | Inhibitor |
| 32 | 4-Chloromercuribenzoic acid | Inhibitor |
| 33 | CGP-74514A hydrochloride | Inhibitor |
| 34 | Cyproterone acetate | Antagonist |
| 35 | Calcimycin | |
| 36 | Cantharidic Acid | Inhibitor |
| 37 | Daphnetin | Inhibitor |
| 38 | Y-27632 dihydrochloride | Inhibitor |
| 39 | CK2 Inhibitor 2 | Inhibitor |
| 40 | 1,4-Dideoxy-1,4-imino-D-arabinitol | Inhibitor |
| 41 | Diacylglycerol Kinase Inhibitor II | Inhibitor |
| 42 | 2,4-Dinitrophenyl 2-fluoro-2-deoxy-beta-D-glucopyranoside | Inhibitor |
| 43 | Tyrphostin AG 1296 | Inhibitor |
| 44 | S-(−)-Carbidopa | Inhibitor |
| 45 | P1,P4-Di(adenosine-5')tetraphosphate triammonium | Inhibitor |
| 46 | SD-169 | Inhibitor |
| 47 | PD 169316 | Inhibitor |
| 48 | Dephostatin | Inhibitor |
| 49 | 2,4-Diamino-6-pyrimidinone | Inhibitor |
| 50 | Dantrolene sodium | Inhibitor |
| 51 | Diethylenetriaminepentaacetic acid | Inhibitor |
| 52 | 3,4-Dichloroisocoumarin | Inhibitor |
| 53 | 1-Deoxynojirimycin hydrochloride | Inhibitor |
| 54 | 7-Cyclopentyl-5-(4-phenoxy)phenyl-7H-pyrrolo[2,3-d]pyrimidin-4-ylamine | Inhibitor |
| 55 | DL-erythro-Dihydrosphingosine | Inhibitor |
| 56 | (R,R)-cis-Diethyl tetrahydro-2,8-chrysenediol | Antagonist |
| 57 | Epibestatin hydrochloride | Inhibitor |
| 58 | 2,2'-Bipyridyl | Inhibitor |
| 59 | SP600125 | Inhibitor |
| 60 | AC-93253 iodide | Agonist |
| 61 | E-64 | Inhibitor |
| 62 | SB 415286 | Inhibitor |
| 63 | rac-2-Ethoxy-3-octadecanamido-1-propylphosphocholine | Inhibitor |
| 64 | Forskolin | Activator |
| 65 | beta-Estradiol | |
| 66 | GW2974 | Inhibitor |
| 67 | GW5074 | Inhibitor |
| 68 | Estrone | |
| 69 | Furegrelate sodium | Inhibitor |
| 70 | Genistein | Inhibitor |
| 71 | Endothall | Inhibitor |
| 72 | rac-2-Ethoxy-3-hexadecanamido-1-propylphosphocholine | Inhibitor |
| 73 | Emodin | Inhibitor |
| 74 | Flutamide | Inhibitor |
| 75 | 17alpha-hydroxyprogesterone | Metabolite |
| 76 | 4-Hydroxybenzhydrazide | Inhibitor |
| 77 | Iodoacetamide | Inhibitor |
| 78 | 1,3,5-tris(4-hydroxyphenyl)-4-propyl-1H-pyrazole | Agonist |
| 79 | HA-100 | Inhibitor |
| 80 | HA-1004 hydrochloride | Inhibitor |
| 81 | Hydrocortisone | |
| 82 | MNS | Inhibitor |
| 83 | Ibudilast | Inhibitor |
| 84 | Hydrochlorothiazide | Inhibitor |
| 85 | NSC 95397 | Inhibitor |
| 86 | Hispidin | Inhibitor |
| 87 | Imazodan | Inhibitor |
| 88 | ML-7 | Inhibitor |
| 89 | Kenpaullone | Inhibitor |
| 90 | LFM-A13 | Inhibitor |
| 91 | 1-(5-Isoquinolinylsulfonyl)-3-methylpiperazine dihydrochloride | Inhibitor |
| 92 | 1-(5-Isoquinolinylsulfonyl)-2-methylpiperazine dihydrochloride | Inhibitor |
| 93 | Aurothioglucose | Inhibitor |
| 94 | L-Leucinethiol, oxidized dihydrochloride | Inhibitor |
| 95 | (−)-Tetramisole hydrochloride | Inhibitor |
| 96 | K 185 | Antagonist |
| 97 | LY-294,002 hydrochloride | Inhibitor |
| 98 | Milrinone | Inhibitor |
| 99 | Myricetin | Inhibitor |
| 100 | 8-Methoxymethyl-3-isobutyl-1-methylxanthine | Inhibitor |
| 101 | BIO | Inhibitor |
| 102 | MK-886 | Inhibitor |
| 103 | Melatonin | Agonist |
| 104 | Mifepristone | Antagonist |
| 105 | PRL-3 Inhibitor I | Inhibitor |
| 106 | H-8 dihydrochloride | Inhibitor |
| 107 | Norcantharidin | Inhibitor |
| 108 | ZM 39923 hydrochloride | Inhibitor |
| 109 | L-alpha-Methyl DOPA | Inhibitor |
| 110 | Me-3,4-dephostatin | Inhibitor |
| 111 | Nordihydroguaiaretic acid from Larrea divaricata (creosote bush) | Inhibitor |
| 112 | Nilutamide | Inhibitor |
| 113 | Olomoucine | Inhibitor |
| 114 | Oleic Acid | Activator |
| 115 | Progesterone | |
| 116 | Piceatannol | Inhibitor |
| 117 | NS 2028 | Inhibitor |
| 118 | SB 216763 | Inhibitor |
| 119 | TBB | Inhibitor |
| 120 | Pentoxifylline | Inhibitor |
| 121 | PD 404,182 | Inhibitor |
| 122 | Palmitoyl-DL-Carnitine chloride | Modulator |
| 123 | ODQ | Inhibitor |
| 124 | Papaverine hydrochloride | Inhibitor |
| 125 | Protoporphyrin IX disodium | Activator |
| 126 | SU 6656 | Inhibitor |
| 127 | 1,10-Phenanthroline monohydrate | Inhibitor |
| 128 | IC 261 | Inhibitor |
| 129 | Bay 11-7082 | Inhibitor |
| 130 | A3 hydrochloride | Inhibitor |
| 131 | PD 98,059 | Inhibitor |
| 132 | Phorbol 12-myristate 13-acetate | Activator |
| 133 | Cortexolone | Precursor |
| 134 | IRAK-1/4 Inhibitor I | Inhibitor |
| 135 | Raloxifene hydrochloride | Modulator |
| 136 | Rottlerin | Inhibitor |
| 137 | Spironolactone | Antagonist |
| 138 | Phosphoramidon disodium | Inhibitor |
| 139 | PQ401 | Inhibitor |
| 140 | SU 5416 | Inhibitor |
| 141 | DL-Stearoylcarnitine chloride | Inhibitor |
| 142 | SU 4312 | Inhibitor |
| 143 | Tyrphostin AG 1478 | Inhibitor |
| 144 | Tyrphostin AG 528 | Inhibitor |
| 145 | Tyrphostin AG 112 | Inhibitor |
| 146 | Tyrphostin AG 494 | Inhibitor |
| 147 | Tyrphostin AG 537 | Inhibitor |
| 148 | Tyrphostin 1 | Inhibitor |
| 149 | N-p-Tosyl-L-phenylalanine chloromethyl ketone | Inhibitor |
| 150 | Tyrphostin AG 555 | Inhibitor |
| 151 | Tyrphostin 23 | Inhibitor |
| 152 | Tyrphostin AG 490 | Inhibitor |
| 153 | Tyrphostin AG 698 | Inhibitor |
| 154 | Tyrphostin AG 34 | Inhibitor |
| 155 | Tyrphostin AG 879 | Inhibitor |
| 156 | Tyrphostin AG 527 | Inhibitor |
| 157 | Tyrphostin AG 808 | Inhibitor |
| 158 | Triamcinolone | Agonist |
| 159 | Tetraisopropyl pyrophosphoramide | Inhibitor |
| 160 | Tyrphostin 25 | Inhibitor |
| 161 | SQ 22536 | Inhibitor |
| 162 | Tetramisole hydrochloride | Inhibitor |

TABLE 4-continued

176 Selected LOPAC1280 ™ Compounds

| No. | Compound | Action |
|---|---|---|
| 163 | Tolazamide | Releaser |
| 164 | Tyrphostin AG 835 | Inhibitor |
| 165 | Tamoxifen citrate | Inhibitor |
| 166 | U0126 | Inhibitor |
| 167 | Tyrphostin 47 | Inhibitor |
| 168 | YC-1 | Activator |
| 169 | Tyrphostin 51 | Inhibitor |
| 170 | Wortmannin from *Penicillium funiculosum* | Inhibitor |
| 171 | I—OMe-Tyrphostin AG 538 | Inhibitor |
| 172 | Tyrphostin A9 | Inhibitor |
| 173 | CGP 57380 | Inhibitor |
| 174 | Tyrphostin AG 538 | Inhibitor |
| 175 | Thapsigargin | Releaser |
| 176 | Tyrphostin AG 126 | Inhibitor |

The foregoing 176 selected compounds from the complete LOPAC1280™ library were then used to screen human pluripotent stem cells, e.g., hESCs, and differentiating cultures during Stage 1 (definitive endoderm) using a real-time impedance assay (ACEA biosciences RT-CES system). The RT-CES system uses 96-well trays that contain embedded microsensors to monitor changes in electrical impedance, which is translated into a measure of cell index. Any overt alteration within a cell culture can be detected, including but not limited to cell proliferation, migration, cell spreading, apoptosis, differentiation and the like. Previous experiments have shown that hES cells attached and expanded effectively in RT-CES trays. An increase in the cell index indicates proliferation of the cells, for example, proliferation of the undifferentiated cells. Proliferation was confirmed by Q-PCR. See also FIG. 1. A decrease or reduction in the cell index (impedance) indicated that the compound had an inhibitory or cytotoxic effect on the cells. In contrast, inactive compounds, or compounds found not to be inhibitory and/or cytotoxic, typically have similar cell indices (impedance) as that demonstrated in the DMSO control. A "scallop" cell index is one which remains high due to a confluent culture of cells, but will go down and up (scallop) between daily feedings. Conversely, cells undergoing differentiation have distinctive patterns, such as peaks and troughs in the cell index, potentially indicative of an epithelial-to-mesenchymal transition, flattening, cell migration, apoptosis or similar differentiation and growth related changes.

Figure 3A:
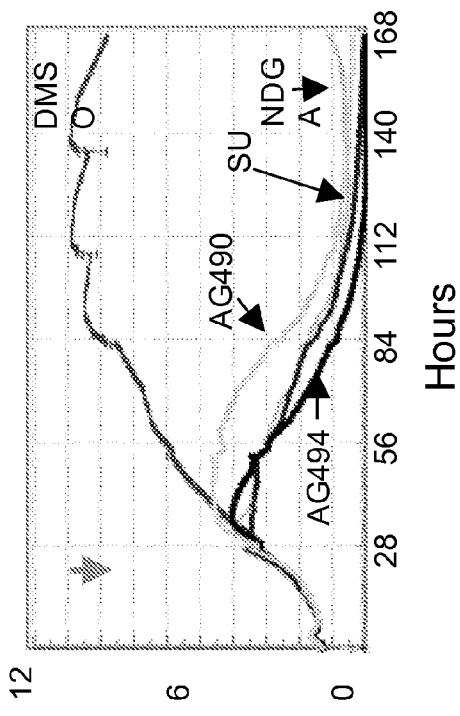
FIGS. 3A-3D are graphs tracing real time impedance assays of hES cells (hESC.
Figure 3B:
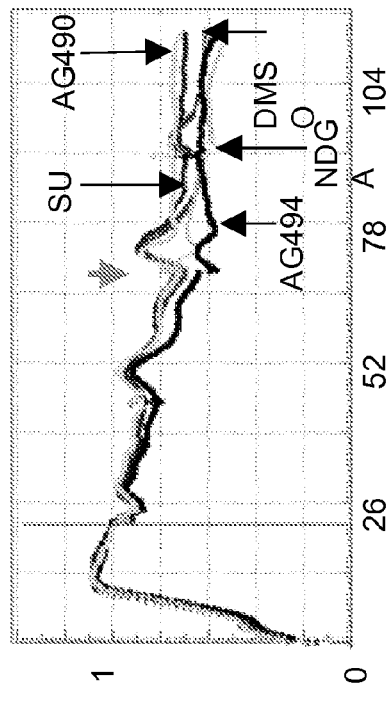

Impedance Assay for Inhibitory and Cytotoxic Agents. Human pluripotent stem cells, e.g., $2 \times 10^4$ hESCs (BG02), were cultured in DC-HAIF, a heregulin-based defined media, with daily feeding in the impedance monitoring plates. After about 24 hours, and 10 μM of the selected LOPAC1280™ compound was added to each well (see arrowhead in FIGS. 3 A & B) and cultured for about an additional 5 days. Seven compounds (BTO-1 (Cmpd. No. 16), Chelerythrine chloride (Cmpd. No. 25), Dephostatin (Cmpd. No. 48), Tyrphostin AG 494 (AGA494; Cmpd. No. 146), Tyrphostin AG 490 (AGA490; Cmpd. No. 152), SU 6656 (Cmpd. No. 126) and Nordihydrogualaretic acid (NDGA; Cmpd. No. 111)) were identified because they caused a significant decrease in the cell index (or impedance), indicating inhibitory or cytotoxic effect on the hESCs, as compared to the DMSO control; which were conducted in parallel over the course of these studies. The spike in impedance observed in the Dephostatin well around 112 hours was due to contamination and is an artifact (FIG. 3A).

Figure 3C:
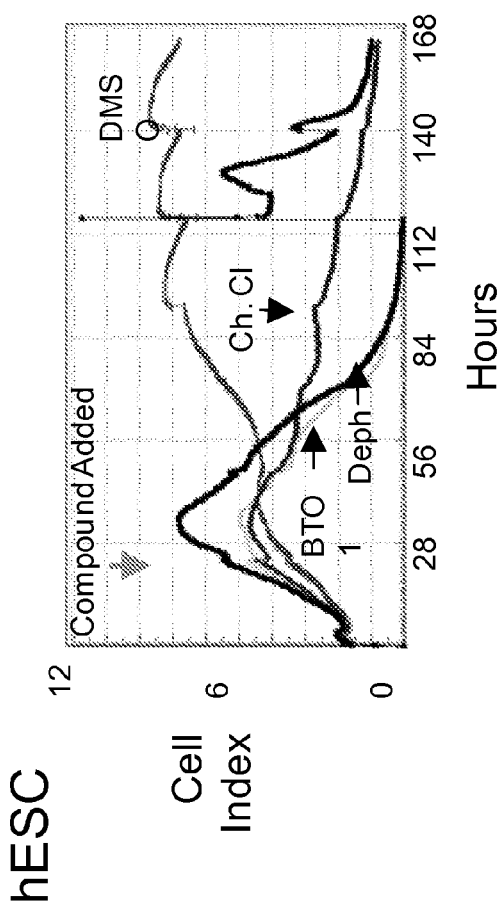
Figure 3D:
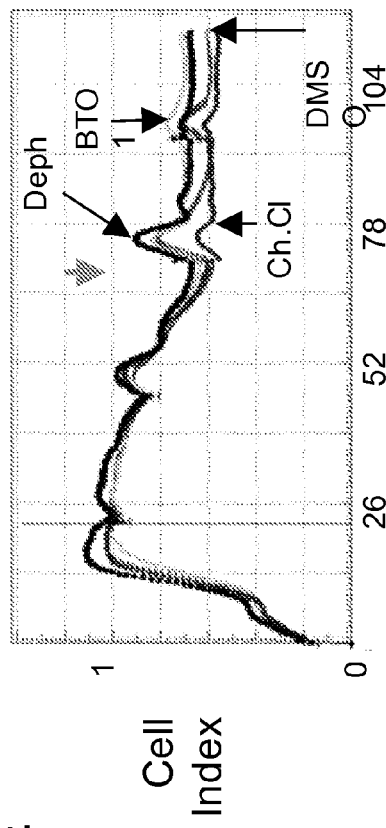

The impedance assay on the hESCs using the compounds in Table 4 above gave greater than twenty (20) hits. However, the ideal candidate compound of the present invention should not only be inhibitory or cytotoxic to human pluripotent stem cells, such as hESCs or hIPSCs, but should at the same time have no effect on cell viability of differentiated or differentiating cell populations including Stage 1, 2, 3, 4 and 5 type cells cultures (definitive endoderm, foregut endoderm, posterior foregut, pancreatic endoderm and endocrine cells, respectively). Hence, the compounds in Table 4 were then screened on differentiating definitive endoderm (DE) cell cultures (FIGS. 3C & D). Approximately $3 \times 10^4$ hES cells were plated per well and grown for 24 hrs in DC-HAIF defined medium (i.e. StemPro® hESC SFM medium (Life Technologies, Carlsbad, Calif.). Stage 1 or definitive endoderm differentiation was then induced by changing the medium and culturing in RPMI, 100 ng/mL Activin A, and 10 ng/mL of FGF2. nM/mL of GSK-3 beta Inhibitor 15 (Calbiochem #361558) as added to the culture for the first 24 hours of differentiation only. 10 μM of each of the candidate compounds were added about 48 hours or 2 days after differentiation was induced (see FIGS. 3 C & D, large arrowhead), and the cells were cultured for an additional 2 days. Of the compounds listed in Table 4, the following compounds in Table 5 below demonstrated cytotoxicity or inhibitory effects of hESC growth and proliferation while at the same time not apparently affecting cell viability of differentiating hESCs or differentiated endoderm cells.

TABLE 5

Select Candidate LOPAC1280 ™ Compounds

| Cmpd. No. (Table 4) | Compound Name | Activity | Target | Description | Viability of Definitive Endoderm |
|---|---|---|---|---|---|
| 16 | BTO-1 | Inhibitor | Plk | Polo-like kinase (Plk) Inhibitor | Viable |
| 25 | Chelerythrine chloride | Inhibitor | PKC | PKC inhibitor; affects translocation of PKC from cytosol to plasma membrane | Viable |
| 48 | Dephostatin | Inhibitor | CD45 | CD45 protein tyrosine kinase inhibitor | Viable |
| 111 | Nordihydrogualaretic acid | Inhibitor | Lipoxygenase | Lipoxygenase inhibitor | |
| 125 | Protoporphyrin IX | Activator | Guanylyl | Activates soluble guanylyl cyclase | |
| 126 | SU 6656 | Inhibitor | Src family | Selective Src family kinase inhibitor | Viable |

TABLE 5-continued

Select Candidate LOPAC1280 ™ Compounds

| Cmpd. No. (Table 4) | Compound Name | Activity | Target | Description | Viability of Definitive Endoderm |
|---|---|---|---|---|---|
| 142 | SU 4312 | Inhibitor | KDR | VEGFR1/2 and PDGFR inhibitor | |
| 146 | Tyrphostin AG 494 | Inhibitor | EGFR | Protein tyrosine kinase inhibitor; inhibits EGF-receptor kinase activity | |
| 150 | Tyrphostin AG 555 | Inhibitor | EGFR | EGFR protein tyrosine kinase inhibitor | N/D |
| 152 | Tyrphostin AG 490 | Inhibitor | JAK2 | Jak-2 protein tyrosine kinase (PTK) inhibitor | Viable |

Secondary Screen with Selected Compounds. A secondary screen using 9 of the 10 candidate compounds in Table 5 was performed by adding the compounds to differentiating Stage 1 cultures (definitive endoderm) as described above. For the secondary screen, larger standard 6-well trays were used instead of the RT-CEAS 96-well culture plates used in primary screens employing impedance assays. Only 9 of the 10 compounds in Table 5 were tested because the 10$^{th}$ was not available in sufficient quantity at the time the assays were performed. In the larger, 6-well trays, 5 of the 9 compounds listed in Table 5 had no effect on viability of differentiating cells or differentiated definitive endoderm. Stated another way, the definitive endoderm cells were capable of growth and proliferation in the presence of the following five compounds: Chelerythrine chloride (Ch.Cl; Cmpd. No. 25), Dephostatin (Deph.; Cmpd. No.), SU 6656 (SU; Cmpd. No. 126) and Tyrphostin AG 490 (AG490; Cmpd. No. 152). This assay also confirmed that the viability of differentiating cells and differentiated definitive endoderm cells was apparently consistent regardless of the numbers of cells tested, or the size, volume, or source of the culture vessel.

Screen for Effects on Stages 1-5 Differentiation. To further determine whether these 5 candidate compounds added at Stage 1 affected other differentiated cell types (e.g. Stages 2-5: foregut endoderm, posterior foregut endoderm, pancreatic endoderm and endocrine precursor cells, respectively), hES were differentiated in the presence or absence of compounds, and RNA samples were taken at various stages for gene expression analysis by Q-PCR.

Figure 4A:
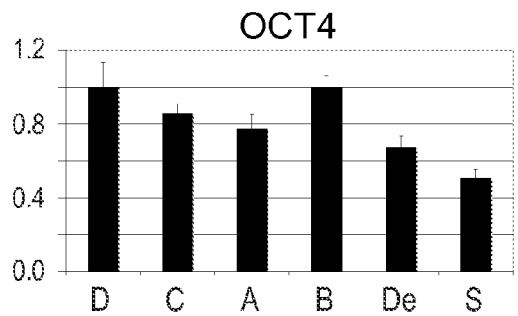
FIGS. 4A-4G are bar graphs showing the relative gene expression levels of OCT4 (FIG. 4A), NANOG (FIG. 4B), FOXA2 (FIG. 4C), SOX17 (FIG. 4D), SOX7 (FIG. 4E), PAX6 (FIG. 4F) and ZIC1 (FIG. 4G) BG02 with treatment of candidate selective cytotoxic agents from the LOPAC1280™ sublibrary (Table 4) to adherent Stage 1 cell cultures of BG02. Expression levels were normalized using the geometric mean of three housekeeping genes, GUSB, CYCG and TBP. The graphs depict fold regulation compared to the hESC sample. The large arrow heads indicate time of the drug treatment. D=DMSO (control); C=Chelerythrine Chloride; A=AG490; B=BTO-1; De=Dephostatin; S=SU6656.
Figure 4E:
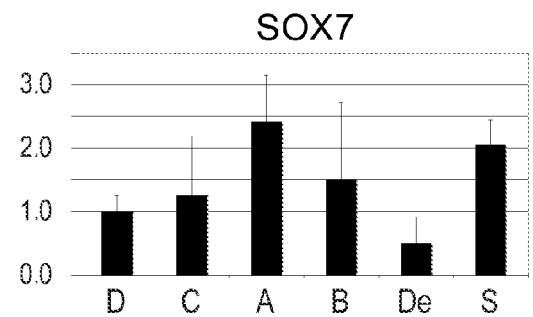
Figure 4B:
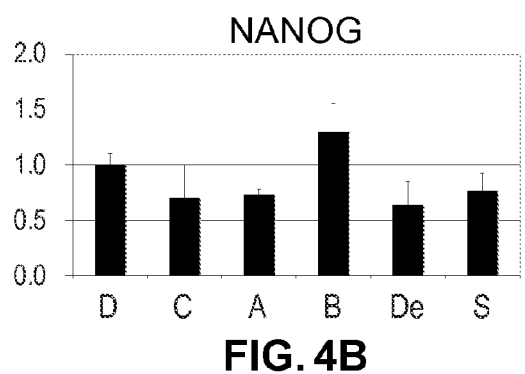
Figure 4F:
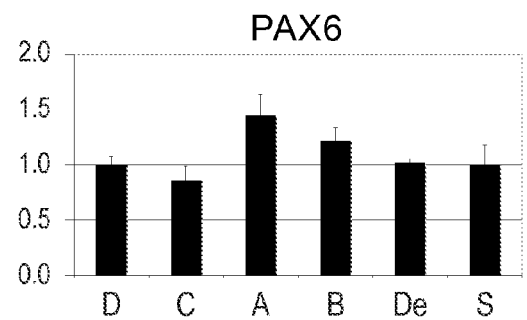
Figure 4C:
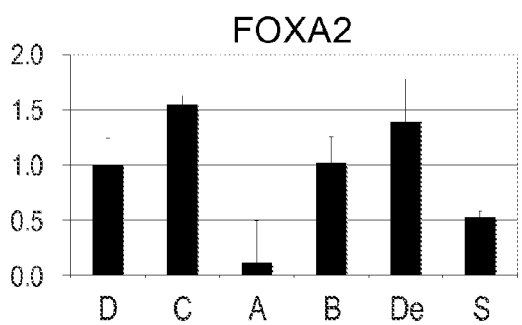
Figure 4G:
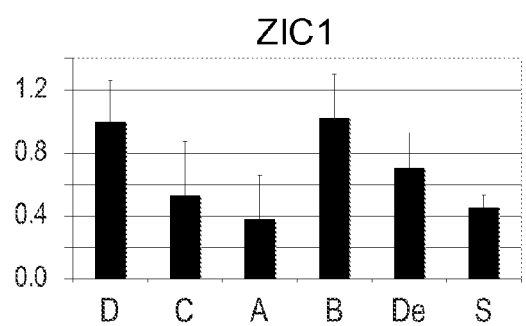
Figure 4D:
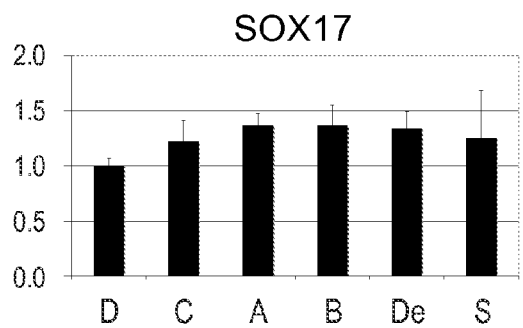
Figure 5A:
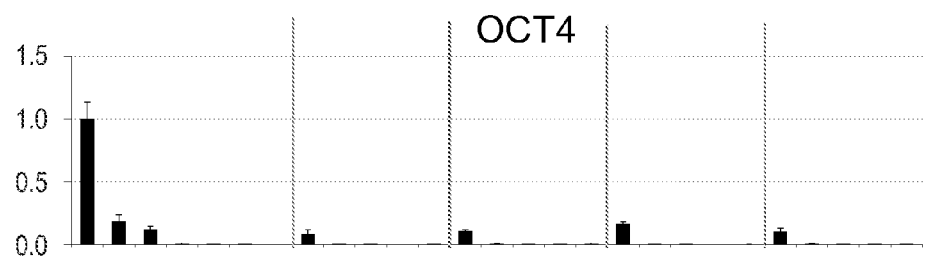
FIGS. 5A-5M. are bar graphs showing the relative gene expression levels of markers expressed in pluripotent cells or in cells of pancreatic lineage: OCT4 (FIG. 5A), MIXL (FIG. 5B), EOMES (FIG. 5C), CXCR4 (FIG. 5D), SOX17 (FIG. 5E), HNF1B (FIG. 5F), HNF4A (FIG. 5G), PDX1 (FIG. 5H), PTF1A (FIG. 5I), NKX2.2.
Figure 5B:
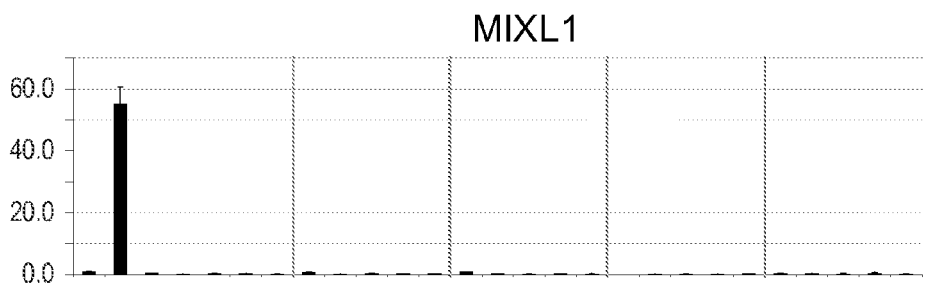
Figure 5C:
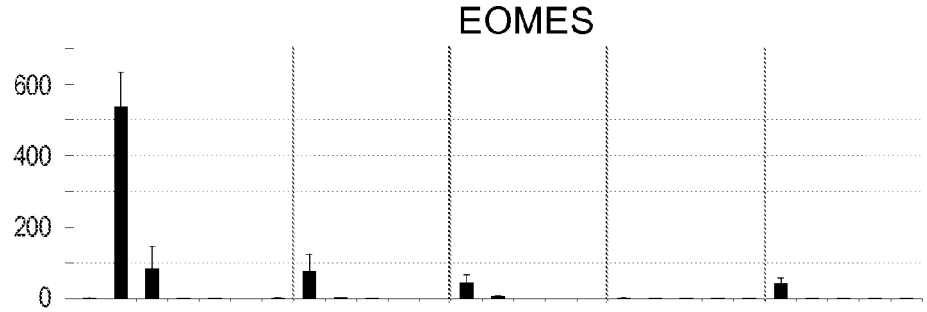
Figure 5D:
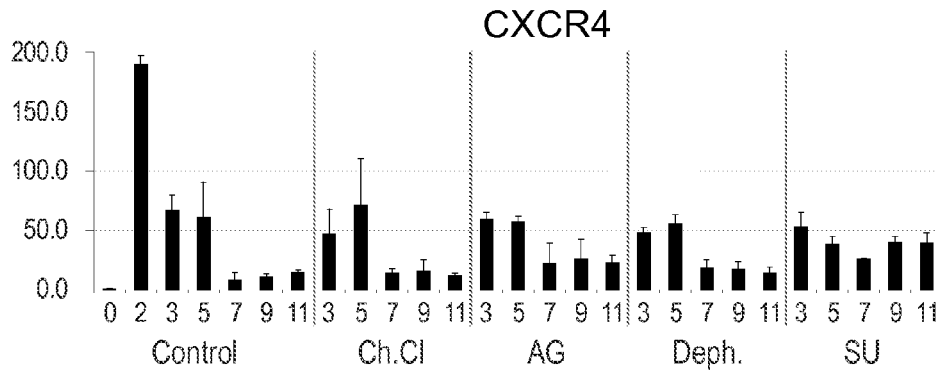
Figure 5E:
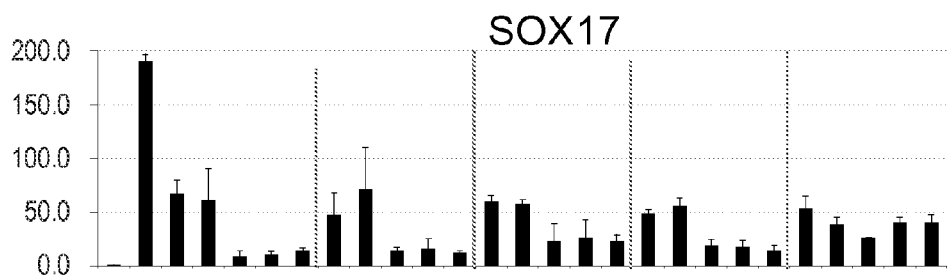
Figure 5F:
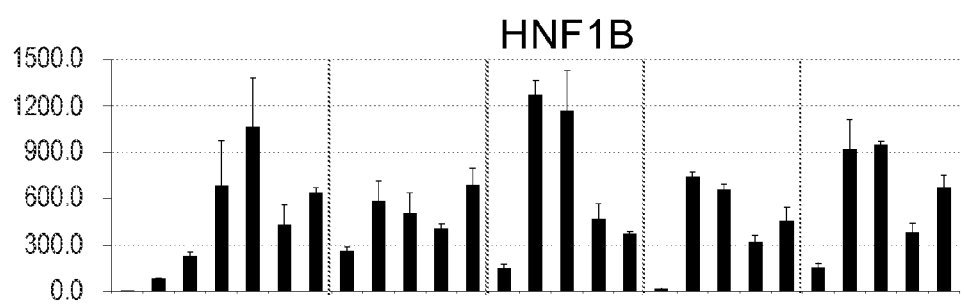
Figure 5G:
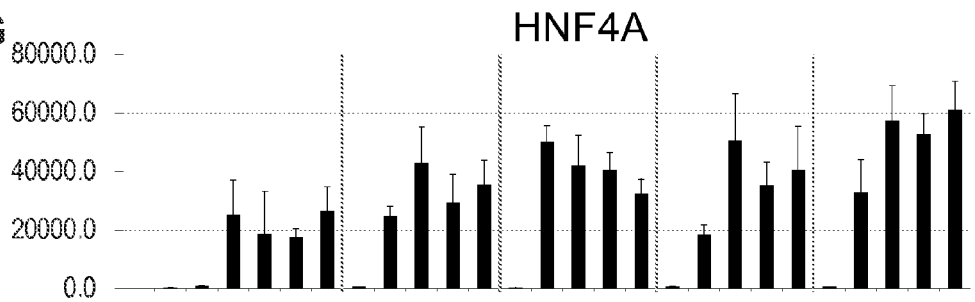
Figure 5H:
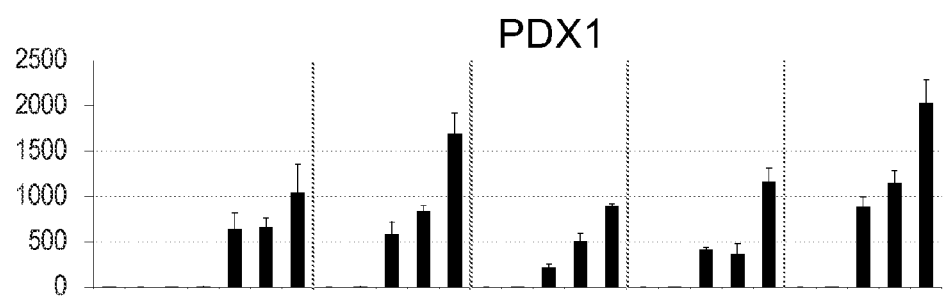
Figure 5I:
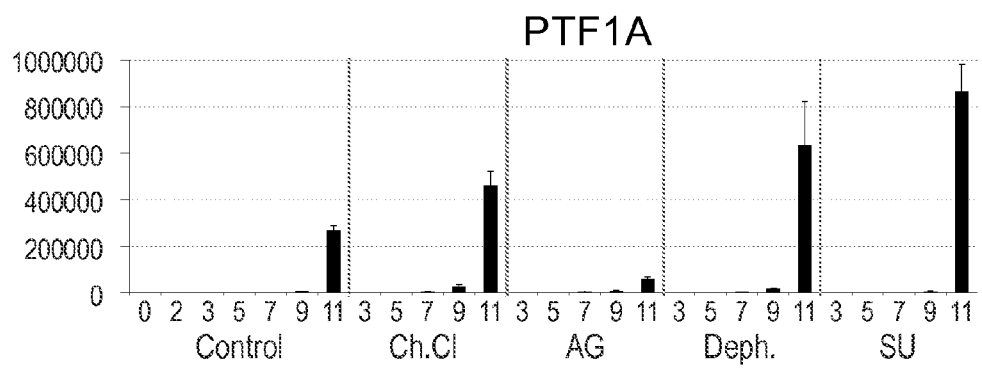
Figure 5J:
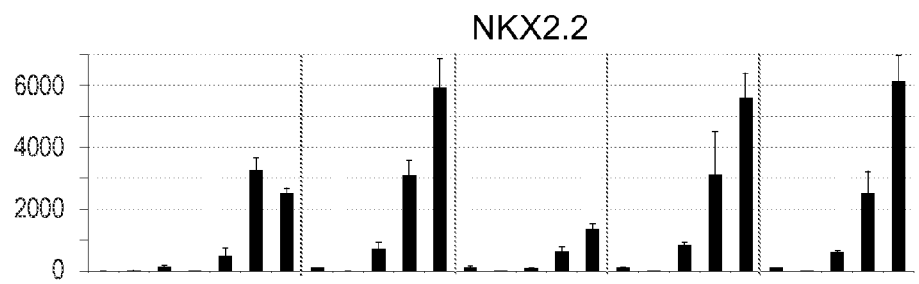
Figure 5K:
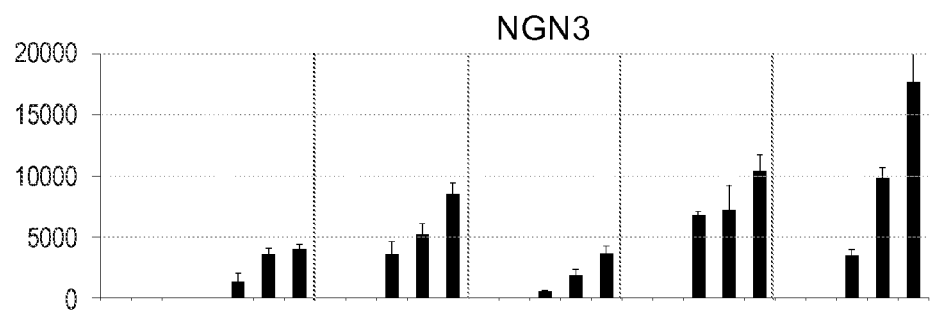
Figure 5L:
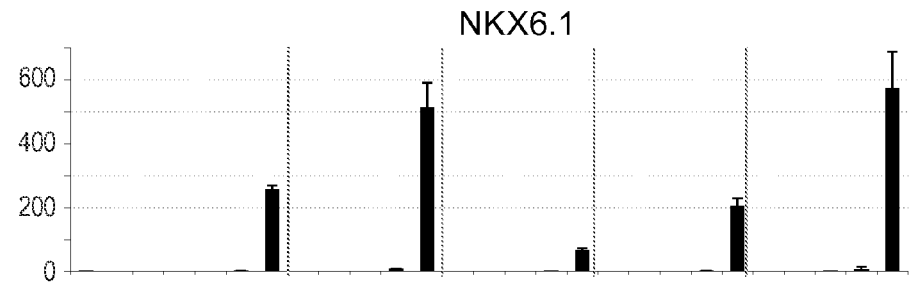
Figure 5M:
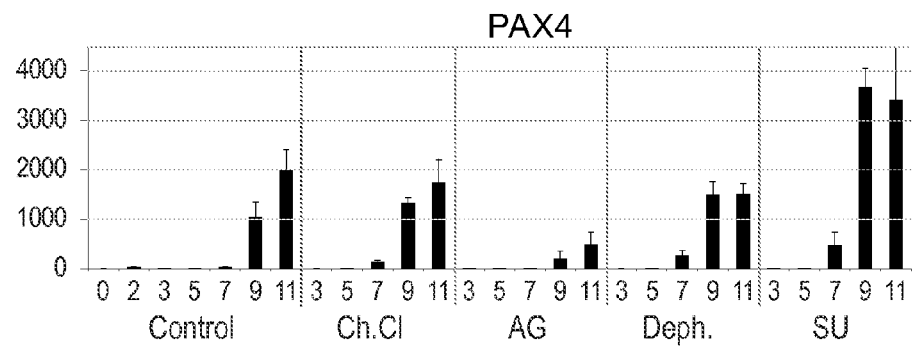
Figure 6D:
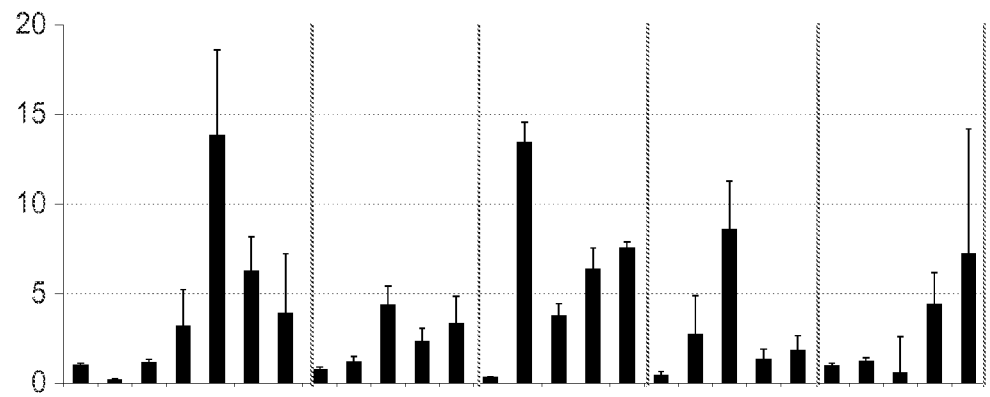
Figure 6E:
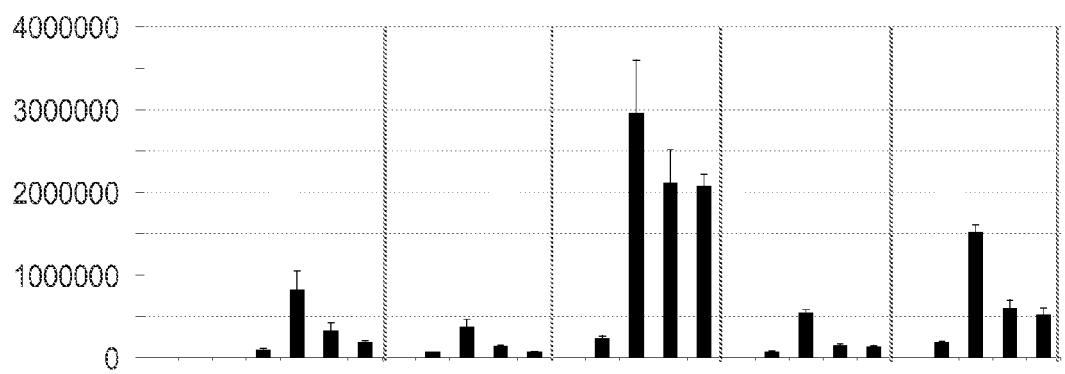
Figure 6F:
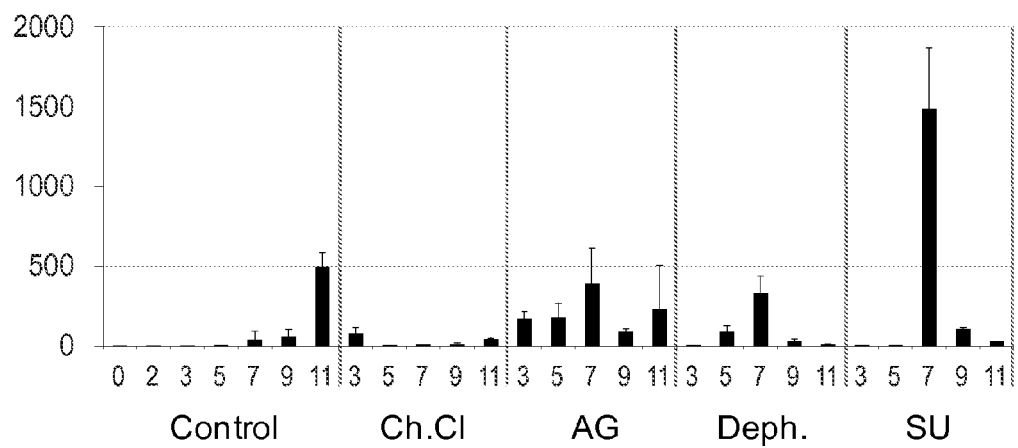

Gene expression levels were plotted relative to a DMSO treated control at the end of Stage 1 (FIG. 4), and relative to undifferentiated hESC aggregates (FIGS. 5 and 6). See "Control" in FIGS. 4, 5 & 6. Cultures treated with Chelerythrine chloride (Ch.Cl; Cmpd. No. 25); Dephostatin (Deph; Cmpd. No. 248); SU 6656 (SU; Cmpd. No. 126) and Tyrphostin AG 490 (AG; Cmpd. No. 152) exhibited a subtle relative decrease in OCT4 and NANOG gene expression (FIGS. 4A & 4B, 2$^{nd}$, 3$^{rd}$, 5$^{th}$ & 6$^{th}$ bars) as compared to the DMSO control (FIGS. 4A & 4B, 1$^{st}$ bar). Chelerythrine chloride, Dephostatin, SU 6656 and Tyrphostin AG 490 compounds each caused an increase in SOX17 gene expression as compared to the DMSO control, consistent with the gene expression profile for Stage 1 definitive endoderm cell cultures (FIG. 4D). However, Tyrphostin AG 490 (AG) and SU 6656 (SU) each caused a decrease in FOXA2 (HNF3β) expression as compared to the DMSO control, indicating adverse effects of these two compounds on definitive endoderm (FIG. 4C). Yet none of the compounds appeared to substantially impact expression of non-definitive endoderm markers including SOX7, PAX6 or ZIC1 (FIGS. 4E, 4F & 4G), and were not, therefore, excluded on the basis of inducing differentiation to other cell types. BTO-1 (BTO1; Cmpd. No. 16) did not appear to have any effect (FIGS. 4A, 4B, 4C & 4D) and was, therefore, excluded from further analysis. This compound neither decreased OCT4 or NANOG expression, nor increased FOXA2 (HNF3β) or SOX17 expression, as would have been expected of a pluripotent stem cell-selective inhibitor/cytotoxic agent.

Effects of Candidate Inhibitor/Cytotoxic Agents in Suspension Aggregate Culture. The ideal inhibitor candidate for cell therapy would be compatible with pancreatic cell lineage viability in a manufacturing scale-up process (e.g. a suspension aggregate culture that could be propagated in a large bioreactor), as well as in small-scale cell culture, such as in 96-well plates or 6-well trays. Thus, an additional screen included conditions similar to those in a commercial-scale process. As noted above, because BTO-1 did not appear to have any effect on OCT4, NANOG, FOXA2 or SOX17, it was not included in this experiment. The remaining 4 compounds, chelerythrine chloride (Ch.Cl; Cmpd. No. 25), tyrphostin AG 490 (AG; Cmpd. No. 152), dephostatin (Deph; Cmpd. No. 48), and SU 6656 (SU; Cmpd. No. 126) were screened for selective inhibition of pluripotent stem cell growth in a suspension aggregate type culture, which is amenable to manufacturing scale-up process. Briefly, Human ESCs were aggregated in rotational culture and differentiated through Stages 1-4 to make pancreatic endoderm substantially as described in U.S. patent application Ser. No. 11/838,054, entitled COMPOSITIONS AND METHODS USEFUL FOR CULTURING DIFFERENTIABLE CELLS, filed Aug. 13, 2007; and U.S. patent application Ser. No. 12/264,760, entitled STEM CELL AGGREGATE SUSPENSION COMPOSITIONS AND METHODS OF DIFFERENTIATION THEREOF, filed Nov. 4, 2008, which are herein incorporated by reference in their entirety. RNA samples were collected from control and compound-treated cell cultures at various time points during the differentiation as above, for analysis by Q-PCR. FIGS. 5A-5M show the expression of markers characteristic of pluripotent stem cells or at least one of Stages 1-5. FIGS. 6A-6F show the expression of markers not normally expressed in pluripotent stem cells or Stages 1-5. Each graph includes 5 sections: QPCR samples were normalized to day 0 (hESC), which is the "Control" section farthest left on each graph of FIGS. 5A-5M; the other four sections to the right of the Control section correspond to the four compounds used to treat the cells (chelerythrine chloride (Ch.Cl; Cmpd. No. 25); tyrphostin AG 490 (AG490; Cmpd. No. 152), dephostatin (Deph; Cmpd. No. 48), and SU 6656 (SU6656; Cmpd. No. 126) left to right, respectively). The Controls included untreated cells (d0 and d2) and DMSO-treated cells (d3, d5, d7, d9 and d11 (left-to-right). Analysis of the data showed that 3 of the 4 compounds, Chelerythrine chloride, dephostatin, and SU 6656 increased PDX1 and NKX6.1 gene expression in Stages 2, 3 and 4 (foregut, posterior foregut & pancreatic endoderm, respectively) as compared to the Controls. See FIGS. 5 H & 5K, last 3 bars. The cultures treated with Tyrphostin AG 490 had reduced gene expression for at least PDX1 and NKX6.1, suggesting poor pancreatic endoderm differentiation. See FIGS. 5 H & 5L. Additionally, analysis of markers of non-pancreatic endoderm cell types (FIGS. 6A-6F) indicated that tyrphostin AG 490 and SU 6656 induced elevated gene expression of AFP and CDX2, respectively. See FIGS. 6E & 6F.

The screening paradigms described above outline an approach for the identification of compounds that display selective cytotoxicity toward and/or inhibit undifferentiated hESC growth and proliferation while at the same time having substantially little or no effect on differentiating hESCs and/or differentiated cells, including Stages 1, 2, 3 and 4 cells (definitive endoderm, foregut endoderm, posterior foregut endoderm, pancreatic progenitors or pancreatic endoderm, respectively).

Example 2

Figure 7A:
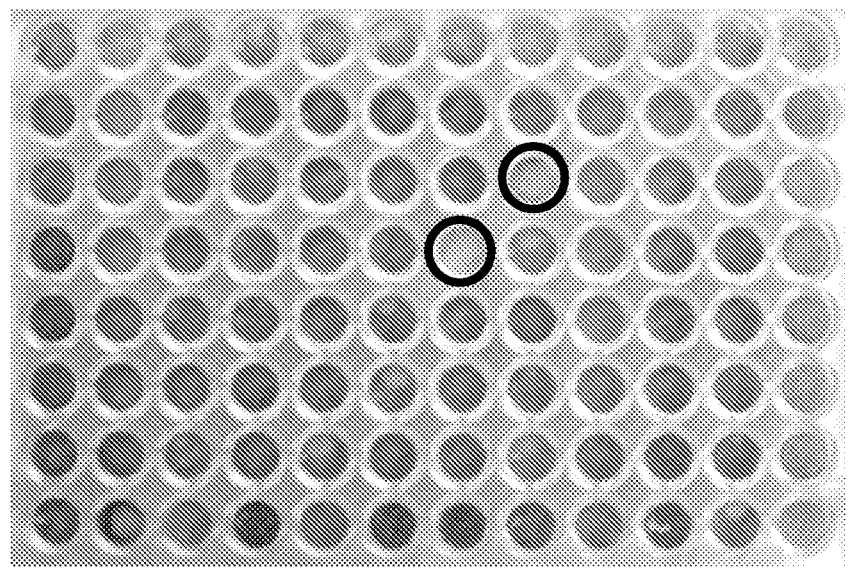
FIGS. 7A and 7B are photographs of 96-well plates containing hESCs and neural progenitors (NPC) derived from hESCs screened with the LOPAC1280™ library. Human ESCs were stained for alkaline phosphatase activity (FIG. 7A); and NPCs were stained with crystal violet (FIG. 7B). The left and right columns of the LOPAC plates are blank and served as untreated controls. Wells exhibiting cytotoxicity or inhibition of growth are circled.

Identification of Selective Cytotoxic/Inhibitory Compounds in the Complete LOPAC1280™ Collection To expand the number of potential candidate hESC cytotoxic and inhibitory compounds, the complete LOPAC1280™ collection (containing 1,280 compounds) was screened. In the primary screen, cytotoxicity was tested on undifferentiated hESCs (about $3 \times 10^4$ BG01 cells) in 16 standard 96-well trays, in DC-HAIF defined medium on growth factor-reduced MATRIGEL™ diluted 1:200, which were fed daily (FIG. 7A). 10 µM of each compound was added to the hESCs one day after plating, and the cells were cultured for an additional 2 days. Plates were then fixed and stained for alkaline phosphatase (AP) to identify relative decreases in proliferation or growth of hESCs (as reduced AP staining), indicative of lower proportions of hESCs. See the circled wells in FIG. 7A.

Figure 7B:
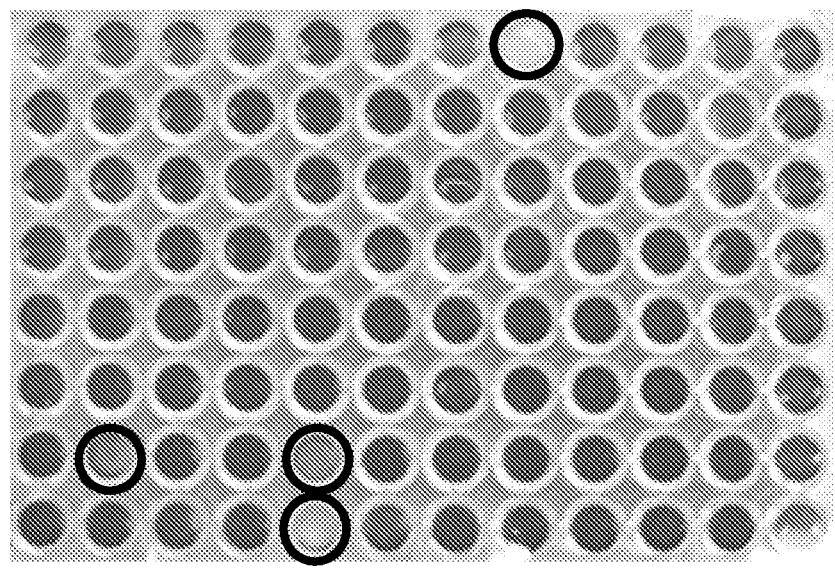

In addition, the complete LOPAC1280™ collection was also screened for effects on neural progenitor cells (NPCs) that were derived from the hESCs. Neural progenitors were plated in serum-free MedII conditioned medium at $6 \times 10^4$ cells/well and fed daily. Two days after plating, 10 µM of each compound was added and the cells were cultured for an additional 2 days. Plates were then fixed and stained with crystal violet, a general cell stain which is capable of revealing relative proliferation or growth activity. Reduced crystal violet staining was indicative of lower proportions of NPCs. See circled wells in FIG. 7B. The left and right columns of the LOPAC1280™ plates from which the compounds were dispensed were empty and served as untreated controls. Those hESC or NPC samples exhibiting cytotoxicity and/or inhibition of growth (i.e. reduced AP or crystal violet staining) were indentified. See the circled wells in FIGS. 7A & B. The primary screens identified forty-one (41) different compounds exhibiting some cytotoxic or inhibitory effect on at least two different cell types, hESCs and NPCs. See Table 6 below listing the name and class of activity of each candidate compound identified in this screen (except chelerythrine chloride, which is listed in Table 5). ChCl was not included in the subsequent round of screening. Therefore only 40 compounds were tested further.

Figure 8:
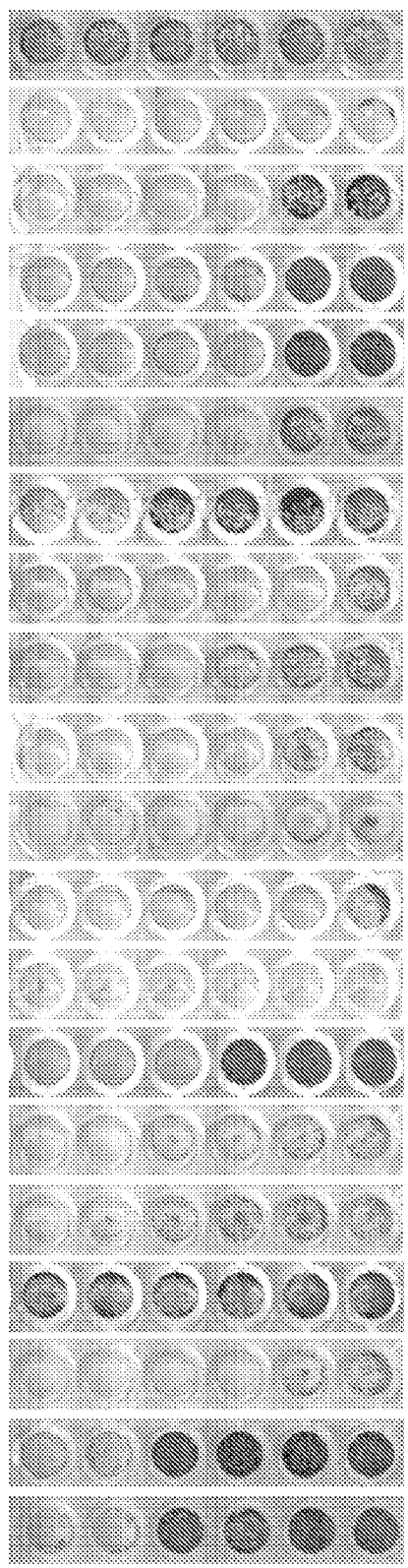
FIG. 8 is a photograph of secondary screening of the LOPAC 1280™ on hESCs of candidate compounds at varying concentrations and stained for alkaline phosphatase activity.
Figure 10A:
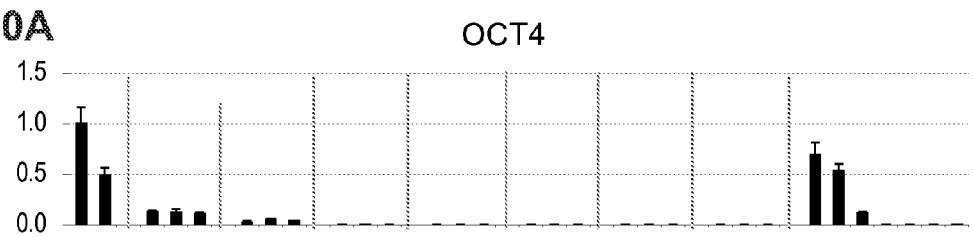
Figure 10B:
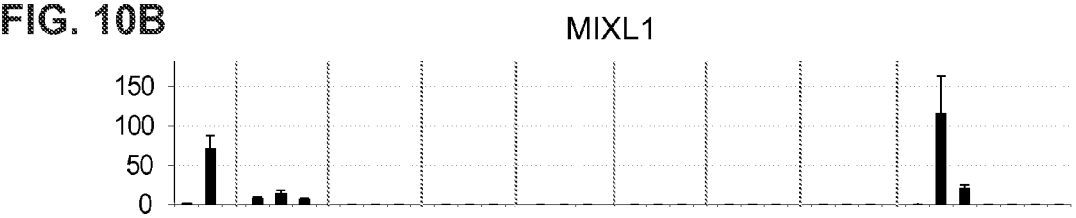
Figure 10C:
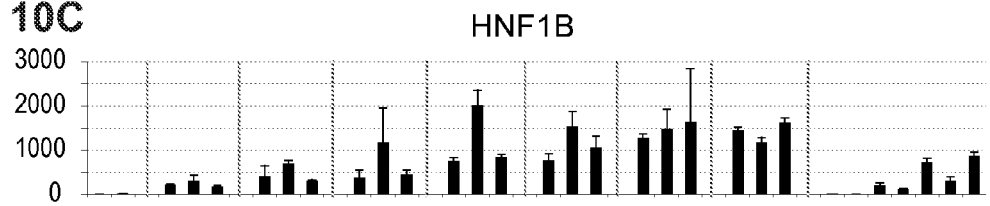
Figure 10D:
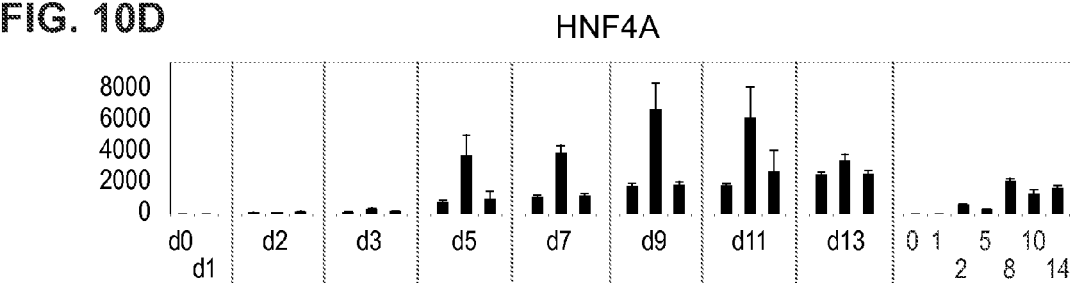

Using a range of different concentrations from 0.1 to 50 µM, the forty compounds in Table 6 were re-screened (secondary screen) using hESCS and NPCs. The effective dose (ED) was defined as the lowest concentration of a compound that elicited cytotoxicity during the secondary screen. FIG. 8 shows the results of staining the cell-containing wells with AP. The darker wells were indicative of the increased numbers or percentages of proliferating or growing pluripotent stem cells in the wells. In addition, these 40 compounds were screened on differentiating definitive endoderm (DE) cell cultures in 96-well plate impedance assays (described above) to determine which of these compounds were not cytotoxic to definitive endoderm cells at the lowest effective dose on either hESC or NPC. Compounds that did not appear to be cytotoxic toward differentiating DE cultures were marked as "viable", meaning that the compound did not affect the survival, growth, proliferation or differentiation of the differentiated cells. See "ACEA DE" column in Table 6. Twenty (20) compounds, including two (2) that were identified in the previous focused screen (see Example 1), were cytotoxic to hESCs but at the same time did not apparently affect survival, growth, proliferation or differentiation of definitive endoderm (DE) cells.

TABLE 6

Lowest Effective Dose of 40 Candidate LOPAC1280 ™ Compounds

| Cat. No. | MW | Name | Class | ED hESC (µM) | ED NPC (µM) | ACEA DE |
|---|---|---|---|---|---|---|
| L 6668 | 648.20564 | Lercanidipine hydrochloride | Calcium Channel | 10 | 10 | |
| A 9809 | 429.92885 | Amsacrine hydrochloride | DNA Repair | 1 | 0.1 | |
| B 7651 | 280.36728 | Brefeldin A from Penicillium | Cytoskeleton | <0.1 | <0.1 | |
| C 8221 | 284.31467 | Caffeic acid phenethyl ester | Cell Cycle | <0.1 | 5 | Viable |
| C 3930 | 687.71276 | Calmidazolium chloride | Intracellular | 5 | 5 | Viable |
| C 9510 | 110.11352 | Pyrocatechol | Cell Cycle | 5 | 5 | Viable |
| C 5982 | 256.69363 | 7-Chloro-4-hydroxy-2-phenyl-1,8-naphthyridine | Adenosine | 5 | 5 | Viable |
| C 7522 | 523.63474 | Calcimycin | Intracellular | 1 | <0.1 | |
| D 3768 | 527.5861 | Dequalinium chloride hydrate | K+ Channel | 5 | 5 | |
| D 0670 | 586.68277 | Dihydroouabain | Ion Pump | 1 | <0.1 | |
| D 2926 | 314.55496 | Diphenyleneiodonium chloride | Nitric Oxide | 0.1 | <0.1 | |
| C-191 | 376.90842 | Capsazepine | Vanilloid | 5 | 25 | Viable |
| D-122 | 425.92188 | Domperidone | Dopamine | 25 | 0.1 | Viable |
| E 2375 | 553.57509 | Emetine dihydrochloride hydrate | Apoptosis | <0.1 | 0.1 | |
| A9605 | 488.4375 | AC-93253 iodide | Hormone | 5 | <0.1 | |

TABLE 6-continued

Lowest Effective Dose of 40 Candidate LOPAC1280 ™ Compounds

| Cat. No. | MW | Name | Class | ED hESC (μM) | ED NPC (μM) | ACEA DE |
|---|---|---|---|---|---|---|
| H 7779 | 391.55841 | Retinoic acid p-hydroxyanilide | Cell Cycle | 1 | 5 | Viable |
| U 6881 | 466.66969 | U-73343 | G-protein | 10 | 5 | Viable |
| N 0287 | 564.5766 | NNC 55-0396 | Ca2+ Channel | 25 | 5 | |
| I-146 | 510.29433 | IB-MECA | Adenosine | 50 | >50 | |
| I 8898 | 875.11658 | Ivermectin | Cholinergic | 5 | >50 | Viable |
| L 2037 | 242.27703 | beta-Lapachone | Apoptosis | 5 | 5 | |
| M 6383 | 302.41727 | 2-methoxyestradiol | Hormone | 10 | 1 | |
| M 5441 | 568.56485 | Mibefradil dihydrochloride | Ca2+ Channel | 25 | 25 | |
| L-119 | 598.48582 | L-703,606 oxalate | Tachykinin | 25 | >50 | |
| M 3184 | 437.36781 | MG 624 | Cholinergic | 0.1 | 5 | Viable |
| N 5023 | 302.37364 | Nordihydroguaiaretic acid from Larrea | Leukotriene | 5 | 5 | Viable |
| P 0547 | 592.69217 | Pentamidine isethionate | Glutamate | 1 | 25 | Viable |
| P 4405 | 414.41584 | Podophyllotoxin | Cytoskeleton and | <0.1 | <0.1 | Viable |
| O 3125 | 584.66683 | Ouabain | Ion Pump | <0.1 | <0.1 | |
| Q 3251 | 472.88999 | Quinacrine dihydrochloride | Neurotransmission | 10 | 25 | Viable |
| P 8293 | 562.67448 | Protoporphyrin IX disodium | Cyclic Nucleotides | 10 | >50 | Viable |
| S 9692 | 371.46152 | SU 6656 | Phosphorylation | 25 | >50 | Viable |
| P 8765 | 164.29279 | Ammonium | Nitric Oxide | 10 | >50 | Viable |
| O 2139 | 417.63751 | N-Oleoyldopamine | Neurotransmission | 5 | 1 | Viable |
| S 7809 | 402.92509 | SKF 96365 | Ca2+ Channel | 25 | 5 | Viable |
| S-009 | 349.40249 | PAPP | Serotonin | 25 | >50 | |
| T 3434 | 294.31273 | Tyrphostin AG 490 | Phosphorylation | 25 | 10 | Viable |
| S-201 | 557.09781 | SB 224289 hydrochloride | Serotonin | 25 | 50 | |
| T 9652 | 471.68907 | Terfenadine | Histamine | 25 | 10 | |
| V 1377 | 909.0741 | Vinblastine sulfate salt | Cytoskeleton | <0.1 | <0.1 | |

The above twenty candidate compounds (Table 6: ACEA DE "viable") were then screened using differentiated hESCs in suspension aggregate culture. Human ESCs (CyT49 cells) were cultured and differentiated in suspension through Stage 1 (definitive endoderm) and Stage 2 (foregut endoderm). The lowest effective dose for each compound was determined as described above and shown in Table 6, and differentiating cell cultures were exposed to this concentration of compound from day 1 (d1) to day 2 (d2). The cultures were then further differentiated to the end of Stage 2 (about day 5, d5). RNA samples were collected at d2 and d5 for analysis of marker gene expression by Q-PCR. Compound-treated samples were compared to untreated control differentiating samples, and normalized to a d2 sample from a previously qualified definitive endoderm differentiation. See FIG. 9 Controls. Several compounds were eliminated from further consideration because treated differentiating aggregates deteriorated, were non-viable or could not be examined by Q-PCR. Several additional compounds were eliminated from further consideration because they appeared to induce off-target differentiation (non-endoderm lineage or non-pancreatic lineage) and increased expression of PAX6 or CDX2 (FIGS. 9G & 9H).

To further determine the effects of the above compounds (excluding those compounds that induced off-target differentiation), three selected compounds (chelerythrine chloride (FIGS. 5 & 6), caffeic acid and Ivermectin) were screened for effects on later stages of pancreatic differentiation, (such as Stages 2-5). Human ESCs were first differentiated through Stage 1 then to Stages 2 to 5 in suspension aggregate cultures similar to that above. Stage 1 cultures were treated with DMSO, caffeic acid or Ivermectin substantially as described above. Untreated control samples were collected at d0 (hESC) and d1 (FIG. 10, left panel), while treated samples were collected at days 2, 3, 5, 7, 9, 11 and 13 (FIG. 10 d2, d3, d5, d7, d9, d11 and d13 respectively). Gene expression levels in the collected samples were analyzed using Q-PCR and compared to the d0 (hESC) sample as well as qualified pancreatic endoderm (FIG. 10, right panel). The qualified pancreatic endoderm control consisted of about 50% pancreatic endoderm, about 46% endocrine cells and about 4% "other" cells as determined by flow cytometry. Neither caffeic acid nor Ivermectin affected survival, growth and/or proliferation of pancreatic endoderm differentiations. That is, the selected compounds inhibited or prevented hESC growth and proliferation or were cytotoxic to hESCs, while at the same time did not affect pancreatic endoderm viability. Typical gene expression levels for Stages 3, 4 and 5 cells were normal; for example, increased expression of NKX6.1 and PTF1A at Stage 4, pancreatic endoderm (FIGS. 10H and 10I), and of NGN3 and NKX2.2 at Stage 5, endocrine precursor and endocrine cells (FIGS. 10 F and 10G) was observed.

In summary, the final three (3) candidates identified from both the primary and secondary screens (EXAMPLE 1) and the full screen of the LOPAC1280™ collection (EXAMPLE 2) were Chelerythrine Chloride, Caffeic acid and Ivermectin. FIG. 11 lists the known or inferred mode(s) of action for these three compounds, as well as their structures. $EC_{50}$ values for the respective cytotoxic effects on undifferentiated hESCs growing in adherent culture were determined using real-time impedance assays.

Example 3

Selection Against Pluripotent Stem Cells in a Differentiated Cell Population

In order to track the presence and or the depletion of undifferentiated pluripotent stem cells in a cell culture (for example, a differentiating or differentiated cell culture population), an assay was developed to improve detection and therefore depletion of the pluripotent stem cells. Although changes in mRNA expression can be measured by Q-PCR, alone this method is not sufficiently dynamic to detect a decrease in the already low levels of undifferentiated pluripotent stem cells. Similarly, immunofluorescent detection (or immunohistochemistry) of OCT4 protein alone during Stage 1 (definitive endoderm differentiation) is not definitive, because cells in the process of differentiation may appear to still express low or sometimes intermediate levels of this protein, e.g., hES cells transitioning to definitive endoderm cells can be co-positive for OCT4$^+$/SOX17$^+$.

Human ES cell suspension aggregates were formed in rotational culture as described previously and differentiated through Stage 1 (definitive endoderm). About 20-30 aggregates were then plated per well in 4-well tissue culture dishes coated with MATRIGEL· diluted 1:200, and cultured for 24 hours in hESC medium (DMEM/F12, 10% XF-KSR, 10 ng/mL Activin A and 10 ng/mL Heregulin). This approach was intended to increase the contrast in OCT4 expression between undifferentiated hESCs and cells committed to differentiation. In the presence of Heregulin-ERBB2/3 and Insulin-InsulinR/IGF1R signaling, undifferentiated hESCs should exhibit strong OCT4 gene expression, while cells committed to differentiation should exhibit down regulation of OCT4 gene expression. Stated in another way, mixed population cell cultures in hESC medium would potentially support expansion/proliferation of residual undifferentiated (hESCs), thereby show increased OCT4 gene expression, as compared to cells committed to differentiation, which would have decreased of OCT4 gene expression. Plated aggregates were immunostained for OCT4 protein and counterstained with DAPI, a nuclear stain (FIG. 12). The cell aggregates that were plated had flattened and spread out within a 24-hour period; while the centers of the aggregates were still domed. The domes were visible, suggesting that they were on the order of only 20-40 micron high. Brightly staining OCT4-positive cells were easily identified and distinguishable from the majority of OCT4 negative cells. OCT4-positive cells were generally found in clusters and most often within the domed area of a plated aggregate. Typically, only a single OCT4-positive cluster was observed in the smallest plated aggregates, whereas larger aggregates had 2 or more clusters. See FIGS. 12 A & 12B as compared to FIGS. 12C-E. Analysis of the DAPI stained cell cultures suggested that the larger aggregates consisted of smaller aggregates because where multiple OCT4-positive clusters were identified, each appeared to be associated with a different smaller aggregate or sub-region within the larger aggregate. Smaller aggregates residing in a larger aggregate may occur as a result of the initial stages of rotational culture, or the aggregation process, during which small clusters (primary aggregates) form initially. Aggregation of two or more primary aggregates likely leads to the formation of larger secondary aggregates, which can be 100-150 µm in diameter. Thus, it is possible that any single clusters of OCT4-positive cells exist at the center of a primary aggregate and resist differentiation. Such clusters would remain substantially undifferentiated and stain OCT4-positive. One hypothesis is that primary aggregates are specified to differentiation relative to their positioning in primary and secondary aggregates. For example, FIGS. 12A through 12E show a representative series of images, from small (primary) (e.g. FIGS. 12A and 12B) and larger (secondary) (e.g. FIGS. 12C-12E) plated aggregates containing OCT4-positive clusters (dark circles). Hence, it is possible that altering the process and/or kinetics of aggregation could improve overall efficiency of differentiation but also have an influence on those cells apparently resistant to differentiation or not differentiating.

Depletion of OCT4-positive cells during Stage 1 differentiation was examined using the plating assay described above. Stage 1 differentiations of hES cells were treated from day 1 to 2 with the candidate compounds as described in Example 2 (chelerythrine chloride, caffeic acid and Ivermectin), at their $EC_{50}$ concentrations for hES cells. Plated untreated and DMSO-treated aggregates were indistinguishable, and both contained discrete clusters of OCT4-positive cells. See FIG. 13A top and bottom panels for a DMSO treated example. The intensity of OCT4-positive staining in differentiating aggregate cell cultures treated with DMSO (control) was equivalent to undifferentiated hES cells. However, aggregate cell cultures treated with 1.4 µM chelerythrine chloride (FIG. 13 B), 0.17 µM Ivermectin (FIG. 13 C), or 0.1 µM caffeic acid (FIG. 13E) exhibited significantly decreased intensity for OCT4 staining Clusters of cells that were OCT4-positive were observable, but at much lower levels as compared to the untreated or DMSO controls. Still, in another study, treatment with 0.1 µM caffeic acid caused an even more substantial decrease in the size of OCT4-positive clusters present 24 hours after plating in hESC medium. See FIG. 14.

Figure 16:
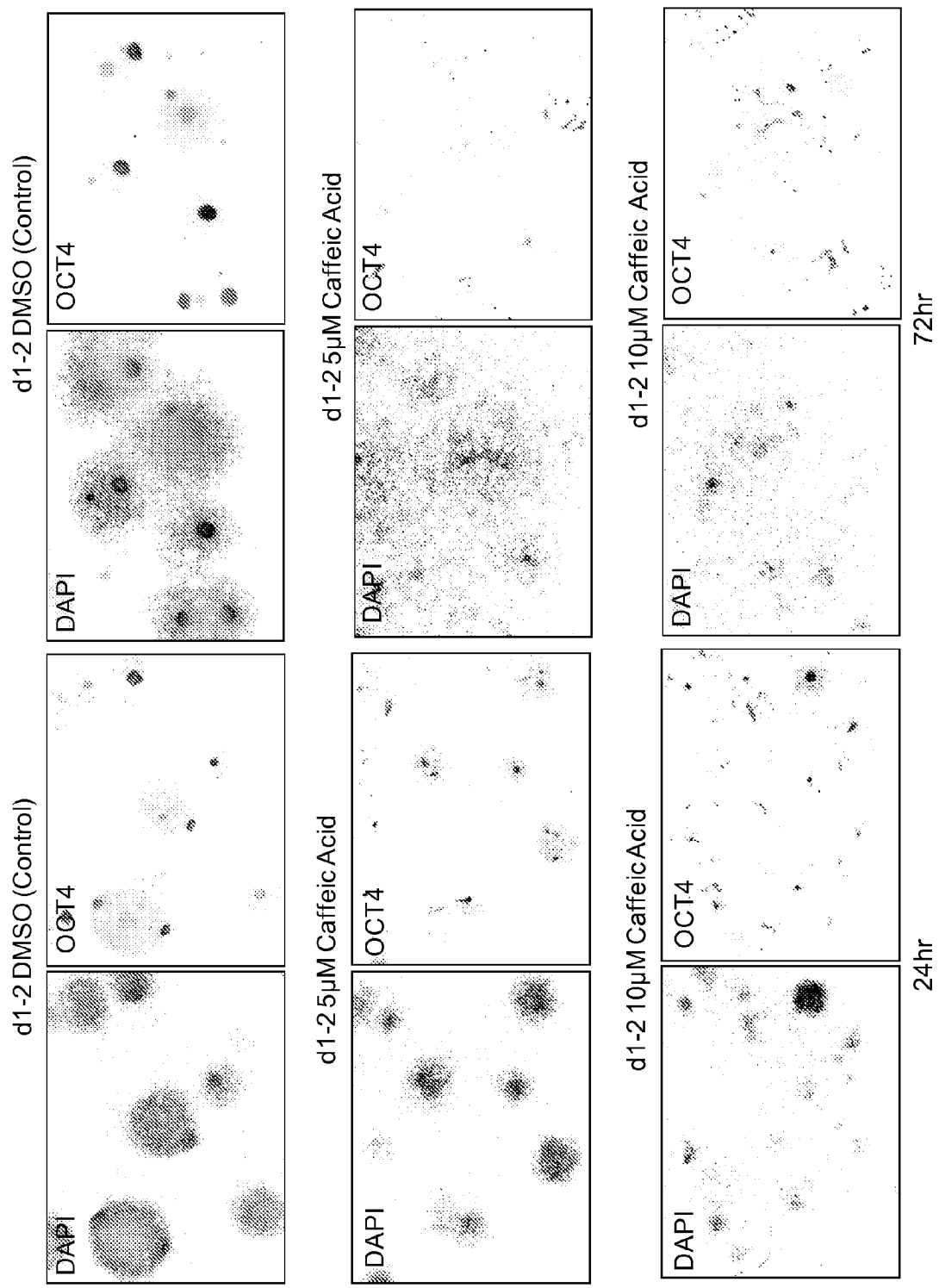
FIG. 16 is a collection of images showing the depletion of OCT4-positive cells in Stage 1 suspension aggregate cultures using caffeic acid from day 1 to 2 of Stage 1. Aggregates were plated in adherent culture in hESC medium for either 24 (left) or 72 hours (right) before staining.
Figure 17:
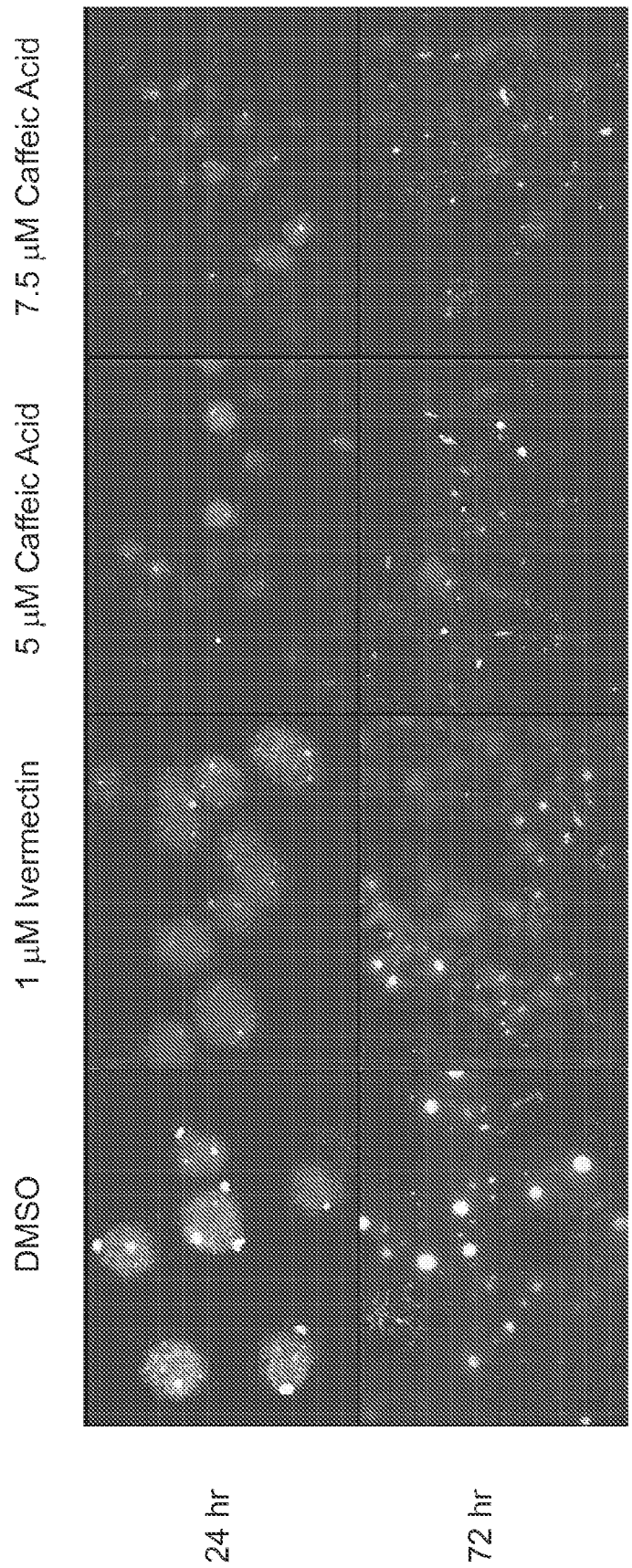
FIG. 17 is a collection of images showing the effects of Ivermectin or caffeic acid (concentrations indicated) on suspension aggregate cultures of differentiations of CyT49 hES cells, following plating on Day 2 in ES cell medium and culture for an additional 24 or 72 hours. Shown is the immunocytochemical staining for OCT4.

Additional experiments were performed using higher concentrations of compounds and extended effects of the compounds in cell culture plated aggregates in hESC medium for 24 or 72 hours before staining (FIGS. 15 and 16). The extended time of culture in hESC medium supported a general expansion in size of OCT4-positive clusters of DMSO-treated aggregates (FIG. 15A), strongly suggesting that the cells could proliferate to generate additional undifferentiated cells that were not committed to differentiation. Another group of Stage 1 differentiating cultures were processed in parallel, but treated with 10 µm chelerythrine chloride. The chelerythrine chloride resulted in a substantially fewer number of OCT4-positive cells 24 hours after plating. By about 72 hours, the OCT4 positive cells had appeared to have proliferated, but clearly below the extent observed for OCT4-positive cells in the control cultures. Similarly, in cell suspension aggregates treated with 5 or 10 µm caffeic acid (FIG. 16), clusters of OCT4-positive cells appeared smaller in size as compared to those in DMSO-treated (or untreated) controls at 24 hours, and did not expand substantially as compared to the DMSO treated control at 72 hours. See FIG. 16.

These data indicate that if maintained and exposed to hESC medium, undifferentiated pluripotent cells can persist through to the end of a 2-day Stage 1 differentiation, and are capable of proliferating and maintaining their undifferentiated or pluripotent status as indicated by the presence of OCT4 protein expression. Treatment with the candidate selective cytotoxic compounds including at least, chelerythrine chloride and caffeic acid, reduce the proportions (or numbers) of OCT4-positive cells as compared to the untreated or DMSO controls; as well as decreasing persistence of OCT4 positive cells in longer term cultures. Use of selective pluripotent cytotoxic compounds can therefore effectively reduce levels of undifferentiated or pluripotent cells, and potentially if implanted for cell therapy, ultimately reduce the frequencies of teratomas in vivo. Moreover, reduction of levels of undifferentiated or pluripotent cells can further reduce potential hyperproliferation of undesirable off-target (non-endoderm) lineages in cell-based therapies, such as those for treatment of type I and II diabetes.

Example 4

Identification of Additional Selective Cytotoxic/Inhibitory Compounds

It is also of interest to identify compounds that are selectively cytotoxic or inhibitory toward off-target or non-endoderm cell types, as well as compounds useful in the differentiation of hESC to other cell types. hESC cytotoxic and inhibitory compounds and/or additional candidate cytotoxic and inhibitory compounds, such as libraries of compounds, are screened for selective inhibitory or cytotoxic activity. In a primary screen, cytotoxicity is tested on hESC, endoderm-lineage (i.e. non-pancreatic or pancreatic endoderm-lineage cells), ectoderm-lineage or mesoderm-lineage cells. About $3 \times 10^4$ cells/well of standard 96-well trays, are grown in a suitable medium and fed daily. 10 µM of each candidate compound is added to the cells one day after plating, and the cells are cultured for an additional 1-2 days to about 2 weeks.

Plates are then fixed and stained with crystal violet, or another general cell stain capable of revealing relative proliferation or growth activity. Plates containing hESCs are stained for alkaline phosphatase. Reduced staining is indicative of lower numbers or proportions of cells in samples treated with candidate compounds. Samples exhibiting cytotoxicity and/or inhibition of growth are indentified. The primary screen identifies compounds exhibiting some cytotoxic or inhibitory effect toward the cell type analyzed.

Using a range of different concentrations from about 0.1 to about 50 µM, compounds identified in the primary screen are re-screened (secondary screen) against two or more cell types selected from hESCs, and non-target endoderm-lineage cells, ectoderm-lineage cells or mesoderm-lineage cells. The effective dose (ED) is determined as the lowest concentration of a compound that elicits cytotoxicity during the secondary screen. Compounds from the secondary screen are then screened on target differentiating cell cultures, such as definitive endoderm (DE). In certain experiments, a 96-well plate impedance assays (described above) is used to determine which of the candidate compounds from the secondary screen are not cytotoxic to the target differentiating cells (e.g. dedefinitive endoderm) at the lowest effective dose. Compounds that do not appear to be cytotoxic toward target differentiating cells are marked as "viable", meaning that the compound does not affect the survival, growth, proliferation or differentiation of the target differentiated cells.

The candidate compounds scored as "viable" are then screened using differentiated hESCs in suspension aggregate culture. Human ESCs are cultured and differentiated in suspension to the target differentiated cell type. The lowest effective dose is determined from the secondary screen (described above), and cell cultures differentiating along the target lineage are exposed to this concentration of compound at various times during the differentiation process. Optionally, the cultures are further differentiated to an endpoint along in the differentiation process. RNA samples are collected at various points in the treatment and differentiation process for analysis of gene expression of markers characteristic of target and off-target differentiation. Compound-treated samples are compared to untreated control differentiating samples, and normalized to samples from a previously qualified target differentiation. Compounds are eliminated from further consideration because differentiation of the target cell type is affected, or because the target differentiating cells deteriorate or become non-viable upon treatment. Additional compounds are eliminated from further consideration because they induce off-target differentiation.

To further determine the effects of the above thus-indentified compounds, selected compounds are screened for effects on later stages of target differentiation. Human ESCs are first differentiated to early to mid stages of target differentiation in suspension aggregate culture. Cultures are treated with DMSO or candidate compounds substantially as described above during an early to mid stage of differentiation. Untreated, DMSO-treated and candidate compound-treated samples are collected at d0 (hESC), d1, and at intervals during the differentiation process. Gene expression levels for markers of target and off-target differentiation in the collected samples are analyzed and compared to d0 (hESC) samples as well as to qualified target differentiations. In some experiments, the cell types present in samples collected as above are also determined by flow cytometry, direct observation or immunohistochemistry. When the percentage or number of hESCs or off-target differentiation is small, cell samples can be expanded under non-differentiating conditions (e.g. in an ES cell medium), prior to analysis. Candidate compounds that do not affect survival, growth and/or proliferation of target differentiation, but prevent growth and proliferation of, or are cytotoxic to hESCs and/or off-target differentiated cells types are selected for further study.

Accordingly, it will be apparent to one skilled in the art that varying substitutions, modifications or optimization, or combinations may be made to the embodiments disclosed herein without departing from the scope and spirit of the invention.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

What is claimed is:

1. An in vitro composition comprising a combination of:
   a) at least one human pluripotent stem cell wherein the pluripotent stem cell has the ability to differentiate into cells of all three germ layers;
   b) at least one differentiating or differentiated derivative from the human pluripotent stem cell; and
   c) an effective amount of a pluripotent stem cell-selective inhibitor or cytotoxic agent selected from the group consisting of: caffeic acid, ivermectin, chelerythrine chloride and mixtures thereof, wherein the effective amount inhibits pluripotent cell growth in the composition as compared to pluripotent cell growth in a composition that does not comprise the effective amount of the inhibitor or cytotoxic agent.

2. The composition of claim 1, wherein the human pluripotent stem cell is a human ES cells or a human iPS cell.

3. The composition of claim 1, wherein effective amount has no effect on the proliferation or viability of the differentiating or differentiated cells.

4. The composition of claim 1, wherein the effective amount does not inhibit the differentiation or differentiation potential of the differentiating or differentiated cells in the population.

5. The composition of claim 1, wherein effective amount is selected from the group consisting of at least about 1 μM caffeic acid, at least about 1 μM ivermectin or at least about 5 μM chelerythrine chloride.

6. The composition of claim 1, wherein the differentiating derivative or differentiated derivative comprises at least one cell type selected from: definitive endoderm cells, PDX1-negative foregut endoderm cells, PDX1-positive foregut endoderm cells, PDX1-positive pancreatic endoderm cells, endocrine progenitor cells and endocrine precursor cells.

7. An in vitro composition comprising a combination of:
   a) at least one human pluripotent stem cell wherein the pluripotent cell has the ability to differentiate into cells of all three germ layers;
   b) at least one differentiating or differentiated derivative from the human pluripotent stem cell; and
   c) an effective amount of ivermectin, wherein the effective amount of ivermectin inhibits pluripotent cell growth in the composition as compared to pluripotent cell growth in a composition that does not comprise the effective amount of the inhibitor or cytotoxic agent.

8. The composition of claim 7, wherein the human pluripotent stem cell is a human ES cells or a human iPS cell.

9. The composition of claim 7, wherein the-effective amount of ivermectin has no effect on the proliferation or viability of the differentiating or differentiated cells.

10. The composition of claim 7, wherein the effective amount of ivermectin does not inhibit the differentiation or differentiation potential of the differentiating or differentiated cells in the population.

11. The composition of claim 7, wherein the effective amount of ivermectin is at least about 1 μM Ivermectin.

12. The composition of claim 7, wherein the differentiating derivative or differentiated derivative comprises at least one cell type selected from: definitive endoderm cells, PDX1-negative foregut endoderm cells, PDX1-positive foregut endoderm cells, PDX1-positive pancreatic endoderm cells, endocrine progenitor cells and endocrine precursor cells.

13. A method for inhibiting human pluripotent cell growth in a population of cells, comprising:
   preparing the in vitro composition of claim 1, thereby inhibiting human pluripotent cell growth in the population of cells.

14. The method of claim 13, wherein the human pluripotent stem cell is a human ES cell or a human iPS cell.

15. The method of claim 13, wherein the effective amount comprises at least about 1 μM caffeic acid, at least about 1 μM ivermectin or at least about 5 μM chelerythrine chloride.

16. The method of claim 13, wherein the effective amount has no effect on the viability or proliferation of the differentiating or differentiated cells.

17. The method of claim 13, wherein the effective amount does not inhibit the differentiation or differentiation potential of the differentiating or differentiated cells.

18. The method of claim 13, wherein the at least one differentiating or differentiated derivative comprises at least one cell type selected from: definitive endoderm cells, PDX1-negative foregut endoderm cells, PDX1-positive foregut endoderm cells, PDX1-positive pancreatic endoderm cells, endocrine progenitor cells and endocrine precursor cells.

19. The method of claim 13, further comprising confirming a reduction in the number or percentage of human pluripotent stem cells in the population of cells.

* * * * *